US011149094B2

(12) United States Patent
Chiu et al.

(10) Patent No.: US 11,149,094 B2
(45) Date of Patent: Oct. 19, 2021

(54) ENGINEERED MULTISPECIFIC ANTIBODIES AND OTHER MULTIMERIC PROTEINS WITH ASYMMETRICAL CH2-CH3 REGION MUTATIONS

(71) Applicant: Janssen Biotech, Inc., Horsham, PA (US)

(72) Inventors: Mark Chiu, Paoli, PA (US); Adam Zwolak, Bala Cynwyd, PA (US)

(73) Assignee: Janssen Biotech, Inc., Horsham, PA (US)

( * ) Notice: Subject to any disclaimer, the term of this patent is extended or adjusted under 35 U.S.C. 154(b) by 39 days.

(21) Appl. No.: 15/997,222

(22) Filed: Jun. 4, 2018

(65) Prior Publication Data

US 2018/0346605 A1 Dec. 6, 2018

Related U.S. Application Data

(60) Provisional application No. 62/515,316, filed on Jun. 5, 2017.

(51) Int. Cl.
*C07K 16/46* (2006.01)
*C07K 16/24* (2006.01)
*C07K 16/10* (2006.01)
*C07K 16/28* (2006.01)

(52) U.S. Cl.
CPC ........ *C07K 16/468* (2013.01); *C07K 16/1027* (2013.01); *C07K 16/1063* (2013.01); *C07K 16/241* (2013.01); *C07K 16/2809* (2013.01); *C07K 16/46* (2013.01); *C07K 2317/31* (2013.01); *C07K 2317/515* (2013.01); *C07K 2317/524* (2013.01); *C07K 2317/526* (2013.01); *C07K 2317/70* (2013.01); *C07K 2317/72* (2013.01); *C07K 2317/94* (2013.01)

(58) Field of Classification Search
CPC .. C07K 16/468; C07K 16/46; C07K 2317/31; C07K 2317/515; C07K 2317/524; C07K 2317/94
USPC .................... 530/387.3; 424/133.1
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,427,908 A | 6/1995 | Dower et al. | |
| 5,571,698 A | 11/1996 | Ladner et al. | |
| 5,580,717 A | 12/1996 | Dower et al. | |
| 5,885,793 A | 3/1999 | Griffiths et al. | |
| 5,969,108 A | 10/1999 | McCafferty et al. | |
| 6,150,584 A | 11/2000 | Kucherlapati et al. | |
| 6,172,197 B1 | 1/2001 | McCafferty et al. | |
| 6,521,404 B1 | 2/2003 | Griffiths et al. | |
| 6,544,731 B1 | 4/2003 | Griffiths et al. | |
| 6,555,313 B1 | 4/2003 | Griffiths et al. | |
| 6,582,915 B1 | 6/2003 | Griffiths et al. | |
| 6,593,081 B1 | 7/2003 | Griffiths et al. | |
| 7,951,917 B1 | 5/2011 | Arathoon et al. | |
| 9,969,800 B2 * | 5/2018 | Igawa | C07K 16/244 |
| 10,519,229 B2 * | 12/2019 | Igawa | G01N 33/6854 |
| 2007/0148164 A1 * | 6/2007 | Farrington | C07K 16/00 424/133.1 |
| 2009/0182127 A1 | 7/2009 | Kjaergaard et al. | |
| 2010/0015133 A1 | 1/2010 | Igawa et al. | |
| 2010/0028637 A1 | 2/2010 | Tavsanli et al. | |
| 2011/0123440 A1 * | 5/2011 | Hansen | C07K 14/70535 424/1.49 |
| 2011/0123532 A1 | 5/2011 | Gurney et al. | |
| 2012/0116057 A1 | 5/2012 | Kannan et al. | |
| 2012/0149876 A1 | 6/2012 | Kreudenstein et al. | |
| 2013/0131319 A1 * | 5/2013 | Igawa | C07K 16/283 530/387.2 |
| 2013/0195849 A1 | 8/2013 | Kreudenstein et al. | |
| 2014/0105889 A1 * | 4/2014 | Igawa | C07K 16/2866 424/133.1 |
| 2014/0234340 A1 * | 8/2014 | Igawa | C07K 16/248 424/172.1 |
| 2014/0271617 A1 * | 9/2014 | Igawa | C07K 16/005 424/130.1 |
| 2014/0273092 A1 | 9/2014 | Flikweert et al. | |
| 2015/0050269 A1 * | 2/2015 | Igawa | C07K 16/18 424/133.1 |
| 2015/0056182 A1 * | 2/2015 | Igawa | C07K 16/248 424/131.1 |
| 2015/0166654 A1 * | 6/2015 | Igawa | C07K 16/005 530/387.3 |
| 2015/0353630 A1 * | 12/2015 | Igawa | C07K 16/00 424/172.1 |
| 2016/0229908 A1 * | 8/2016 | Igawa | C07K 16/4291 |
| 2017/0022270 A1 * | 1/2017 | Igawa | C07K 16/18 |

(Continued)

FOREIGN PATENT DOCUMENTS

WO    WO 1988/01649 A1    3/1988
WO    WO 90/04036 A1    4/1990

(Continued)

OTHER PUBLICATIONS

Zwolak et al. (MAbs. Nov./Dec. 2017;9(8):1306-1316; Epub Sep. 22, 2017).*

(Continued)

*Primary Examiner* — Lynn A Bristol

(74) *Attorney, Agent, or Firm* — Kirk Baumeister

(57) ABSTRACT

The present invention relates to engineered multispecific antibodies and other multimeric proteins with asymmetrical CH2-CH3 region mutations and methods of making and using them.

41 Claims, 25 Drawing Sheets

Specification includes a Sequence Listing.

(56) References Cited

U.S. PATENT DOCUMENTS

| | | | |
|---|---|---|---|
| 2017/0226206 A1* | 8/2017 | Igawa | C07K 14/70535 |
| 2018/0169255 A1* | 6/2018 | Gao | A61K 47/68 |
| 2018/0258161 A1* | 9/2018 | Igawa | C07K 16/2866 |
| 2018/0258163 A1* | 9/2018 | Igawa | C07K 16/40 |
| 2019/0041396 A1* | 2/2019 | Igawa | G01N 33/6845 |
| 2019/0185557 A1* | 6/2019 | Igawa | C07K 16/18 |
| 2019/0218309 A1* | 7/2019 | Igawa | C07K 16/248 |
| 2019/0359704 A1* | 11/2019 | Igawa | C07K 16/248 |

FOREIGN PATENT DOCUMENTS

| | | |
|---|---|---|
| WO | WO 1992/01047 A1 | 1/1992 |
| WO | WO 1994/13804 A1 | 6/1994 |
| WO | WO 1998/44001 A1 | 10/1998 |
| WO | WO 99/45962 A1 | 9/1999 |
| WO | WO 02/043478 A1 | 6/2002 |
| WO | WO 02/066630 A1 | 8/2002 |
| WO | WO 2006/020114 A2 | 2/2006 |
| WO | WO 2006/053301 A2 | 5/2006 |
| WO | WO 2007/143098 A2 | 12/2007 |
| WO | WO 2009/058492 A2 | 5/2009 |
| WO | WO 2009/085462 A1 | 7/2009 |
| WO | WO 2015/158867 A1 | 10/2015 |
| WO | WO 2016/098357 A1 | 6/2016 |
| WO | WO 2017/011342 A9 | 1/2017 |
| WO | WO 2017/034770 A1 | 3/2017 |
| WO | WO 2017/036905 A1 | 3/2017 |

OTHER PUBLICATIONS

Zwolak et al. (Sci Rep. Nov. 14, 2017;7(1):15521; Epub Nov. 14, 2017).*
Baert, et al., "Influence of Immunogenicity on the Long-Term Efficacy of Infliximab in Crohn's Disease," The New England Journal of Medicine, 348: 601-608 (2003).
Bork, et al., "Proposed acquisition of an animal protein domain by bacteria," Proceedings of the National Academy of Science USA, 89:8990-8994 (1992).
Bruggemann, et al. "Production of human antibody repertoires in transgenic mice." Current Opinions inBiotechnolgoy, 8(4): 455-458 (1997).
Bruggemann, et al. "Human antibody production in transgenic mice: expression from 100 kb of the human IgH locus." European Journal of Immunology, 21(5): 1323-1326 (1991).
Chothia, et al. "Canonical structures for the hypervariable regions of immunoglobulins." Journal of Molecular Biology, 196(4): 901-917 (1987).
Dall' Acqua, et al., "Increasing the Affinity of a Human IgF1 for The Neonatal Fc Receptor: Biological Consequences," Journal of Immunology, 169: 5171-5180 (2002).
Fishwild, et al., "High-avidity human IgGK monoclonal antibodies from a novel strain of minilocus transgenic mice," Nature Biotechnology, 14: 845-851 (1996).
Fujiyama, et al., "Homo sapiens mRNA for IgF H chain, Complete cds, clone: 231H5A11H," National Center for Biotechnology Information, Genbank AB776838.
Green, et al., "Antigen-specific human monoclonal antibodies from mice engineered with human Ig heavy and light chain YACs," Nature Genetics, 7: 13-21 (1994).
Green, et al. "Regulation of B cell development by variable gene complexity in mice reconstituted with human immunoglobulin yeast artificial chromosomes." Journal of Experimental Medicine, 188(3): 483-495 (1998).
Green, L. L. "Antibody engineering via genetic engineering of the mouse: XenoMouse strains are a vehicle for the facile generation of therapeutic human monoclonal antibodies." Journal of Immunological Methods, 231(1-2): 11-23 (1999).
Hinton, et al., "Engineered Human IgG Antibodies with Longer Serum Half-lives in Primates," The Journal of Biological Chemistry, 279(8): 6213-6216 (2004).

Hinton, et al., "An Engineered Human IgG1 Antibody with Longer Serum Half-Life," The Journal of Immunology, 176: 346-356 (2006).
Honegger, et al., "Yet Another Numbering Scheme for Immunoglobulin Variable Domains: An Automatic Modeling and Analysis Tool," Journal of Molecular Biology, 309: 657-670 (2001).
Jachimowicz, et al., "Multi-specific Antibodies for Cancer Immunotherapy," BioDrugs, 28: 331-343 (2014).
Knappik, et al., "Fully Synthetic Human Combinatorial Antibody Libraries (HuCAL) Based on Modular Consensus Frameworks and CDSs Randomized with Trinucleotides," The Journal of Molecular Biology, 296: 57-86 (2000).
Kohler and Milstein, "Continuous cultures of fused cells secreting antibody of predefined specificity," Nature 256:495-497 (1975).
Labrijn, et al., "Efficient generation of stable bispecific IgG1 by controlled Fab-arm exchange," Proceedings of the National Academy of Science, 110(13): 5145-5150 (2013).
Lefranc, et al., "IMGT unique numbering for immunoglobulin and T cell receptor variable domains and Ig superfamily V-like domains," Developmental & Comparative Immunology, 27: 55-77 (2003).
Lewis, et al., "Generation of bispecific IgG antibodies by structure-based design of an orthogonal Fab interface," Nature Biotechnology, 32(2): 191-202 (2014).
Lonberg, et al. "Human antibodies from transgenic mice." International Review of Immunology, 13(1): 65-93 (1995).
Lonberg, et al., "Antigen-specific human antibodies from mice comprising four distinct genetic modifications," Nature, 368: 856-859 (1994).
Majumdar, et al., "Correlations between changes in conformational dynamics and physical stability in a mutant IgG1 mAb engineered for extended serum half-life," mAbs, 7(1): 84-95 (2015).
Meinke, et al., "Cellulose-Binding Polypeptides from Cellulomonas fimi: Endoglucanase D (CenD), A Family A l3-1,4-Glucanase," Journal of Bacteriology, 175(7): 1910-1918, 1993.
Mendez, et al., "Functional transplant of megabase human immunoglobulin loci recapitulates human antibody response in mice," Nature Genetics, 15: 146-156 (1997).
Niranjana, et al., "FC IgG1 heavy chain constant region, partial (Homo sapiens)," National Center for Biotechnology Information, Genbank Entry, 359385966.
Petkova, et al., "Enhanced half-life of genetically engineered human IgG1 antibodies in a humanized FcRn mouse model: potential application in humorally mediated autoimmune disease," International Immunology, 18(12): 1759-1769 (2006).
Romagnani, et al., "Demonstration on protein A of two distinct immunoglobulin-binding sites and their role in the mitogenic activity of Staphylococcus aureus Cowan I on human B cells," The Journal of Immunology, 129: 596-602 (1982).
Roopenian, et al., "FcRn: the neonatal Fc receptor comes of age," Nature Review Immunology, 7: 715-725 (2007).
Sasso, et al., "Human IgA and IgG F(ab')2 that bind to staphylococcal protein A belong to the VHIII subgroup," Journal of Immunology, 147(6): 1877-1883 (1991).
Schaefer, et al., "Immunoglobulin domain crossover as a generic approach for the production of bispecific IgG antibodies," Proceedings of the National Academy of Science, 108(27): 11187-11192 (2011).
Shi, et al. "De novo selection of high-affinity antibodies from synthetic fab libraries displayed on phage as pIX fusion proteins." Journal of Molecular Biology, 397(2): 385-396 (2010).
Stapleton, et al., "Competition for FcRn-mediated transport gives rise to short half-life of human IgG3 and offers therapeutic potential," Nature Communications, 2(599): 1-9 (2011).
Stickler, et al., "The human G1m1 allotype associates with CD4+ T-cell responsiveness to a highly conserved IgG1 constant region peptide and confers an asparaginyl endopeptidase cleavage site," Genes and Immunity, 12: 213-221 (2011).
Vaccaro, et al., "Engineering the Fc region of immunoglobulin G to modulate in vivo antibody levels," Nature Biotechnology, 23(10): 1283-1288 (2005).
Vafa, et al., "An engineered Fc variant of an IgG eliminates all immune effector functions via structural perturbations," Methods, 65: 114-126 (2014).

(56) References Cited

OTHER PUBLICATIONS

Watanabe, et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, 265(26): 15659-15665 (1990).
Worn, et al., "Stability Engineering of Antibody Single-chain Fv Fragments," Journal of Molecular Biology, 305: 969-1010 (2001).
Wu, et al., "An Analysis of the Sequence of the Variable Regions of Bence Jones Proteins and Myeloma Light Chains and Their Implications for Antibody Complementarity," Journal of Experimental Medicine, 132(2): 211-250 (1970).
Yang, et al., "Eradication of Established Tumors by a Fully Human Monoclonal Antibody to the Epidermal Growth Factor Receptor without Concomitant Chemotherapy," Cancer Research, 59: 1236-1243 (1999).
Yeung, et al., "Engineering Human IgG1 Affinity to Human Neonatal Fc Receptor: Impact of Affinity Improvement on Pharmacokinetics in Primates," The Journal of Immunology, 182: 7663-7671 (2009).
Zwolak, et al., "Rapid Purification of Human Bispecific Antibodies via Selective Modulation of Protein A Binding," Scientific Reports, 7(1): 1-11 (2017).
PCT International Search Report dated Dec. 11, 2018.
Supplementary European Search Report dated Feb. 3, 2021.

\* cited by examiner

Figure 1A.

```
Human IgG1 CH2     VLTVLHQDWLN    (SEQ ID NO: 104)

Mouse IgG2a CH2    ALPIQHQDWMS    (SEQ ID NO: 105)
```

Figure 3C.

RSV-L
RSV-L[Q311R]
RSV-L[TLQ]
bsRSV-L[Q311R]
bsRSV-L[TLQ]

— bsRSV-L[Q311R] pH 4.6 Elution
--- gp120-R
.... bsRSV-L[Q311R]
~~~ RSV-L[Q311R]

Figure 6D.

— bsRSV-L[Q311R] pH 3.4 Elution
--- gp120-R
···· bsRSV-L[Q311R]
--- RSV-L[Q311R]

Figure 8.

SEQUENCE LISTING

```
<160> NUMBER OF SEQ ID NOS: 105

<210> SEQ ID NO 1
<211> LENGTH: 58
<212> TYPE: PRT
<213> ORGANISM: Artificial sequence
<220> FEATURE:
<223> OTHER INFORMATION: Z domain

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 216
<212> TYPE: PRT
<213> ORGANISM: Artificial sequence
<220> FEATURE:
<223> OTHER INFORMATION: IgG1 HC2-HC3 Q311K

<400> SEQUENCE: 2

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Lys
65                  70                  75                  80

Asp Trp Leu Asn Gly Lys Glu Tyr Lys Cys Lys Val Ser Asn Lys Ala
                85                  90                  95
```

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
            130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
            210                 215

<210> SEQ ID NO 3
<211> LENGTH: 216
<212> TYPE: PRT
<213> ORGANISM: Artificial sequence
<220> FEATURE:
<223> OTHER INFORMATION: IgG1 HC2-HC3 Q311R

<400> SEQUENCE: 3

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
            130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
            210                 215

<210> SEQ ID NO 4

<211> LENGTH: 216
<212> TYPE: PRT
<213> ORGANISM: Artificial sequence
<220> FEATURE:
<223> OTHER INFORMATION: IIgG1 HC2-HC3 T307P/L309Q

<400> SEQUENCE: 4

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 5
<211> LENGTH: 216
<212> TYPE: PRT
<213> ORGANISM: Artificial sequence
<220> FEATURE:
<223> OTHER INFORMATION: IgG1 HC2-HC3 T307P/L309Q/Q311R

<400> SEQUENCE: 5

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
```

```
                    100                 105                 110
Arg Glu Pro Gln Val Tyr Thr Leu Pro Pro Ser Arg Glu Met Thr
                115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 6
<211> LENGTH: 216
<212> TYPE: PRT
<213> ORGANISM: Artificial sequence
<220> FEATURE:
<223> OTHER INFORMATION: IgG1 HC2-HC3 Q311K/F405L

<400> SEQUENCE: 6

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Lys Phe Asn Trp Tyr Val
            35                  40                  45

Asp Gly Val Glu Val His Asn Ala Lys Thr Lys Pro Arg Glu Glu Gln
        50                  55                  60

Tyr Asn Ser Thr Tyr Arg Val Val Ser Val Leu Thr Val Leu His Lys
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
                100                 105                 110

Arg Glu Pro Gln Val Tyr Thr Leu Pro Pro Ser Arg Asp Glu Leu Thr
                115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Leu Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 7
<211> LENGTH: 216
<212> TYPE: PRT
```

<213> ORGANISM: Artificial sequence
<220> FEATURE:
<223> OTHER INFORMATION: IgG1 HC2-HC3 Q311R/F405L

<400> SEQUENCE: 7

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Leu Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 8
<211> LENGTH: 216
<212> TYPE: PRT
<213> ORGANISM: Artificial sequence
<220> FEATURE:
<223> OTHER INFORMATION: IgG1 HC2-HC3 T307P/L309Q/F405L

<400> SEQUENCE: 8

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110
```

Arg Glu Pro Gln Val Tyr Thr Leu Pro Pro Ser Arg Asp Glu Leu Thr
            115                 120                 125

Lys Asn Gln Val Ser Leu Thr Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Leu Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 9
<211> LENGTH: 216
<212> TYPE: PRT
<213> ORGANISM: Artificial sequence
<220> FEATURE:
<223> OTHER INFORMATION: IgG1 HC2-HC3 T307P/L309Q/Q311R/F405L

<400> SEQUENCE: 9

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Leu Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 10
<211> LENGTH: 216
<212> TYPE: PRT
<213> ORGANISM: Artificial sequence
<220> FEATURE:

<223> OTHER INFORMATION: IgG1 HC2-HC3 Q311K/K409R

<400> SEQUENCE: 10

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Lys
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 11
<211> LENGTH: 216
<212> TYPE: PRT
<213> ORGANISM: Artificial sequence
<220> FEATURE:
<223> OTHER INFORMATION: IgG1 HC2-HC3 Q311R/K409R

<400> SEQUENCE: 11

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125
```

```
Lys Asn Gln Val Ser Leu Thr Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 12
<211> LENGTH: 216
<212> TYPE: PRT
<213> ORGANISM: Artificial sequence
<220> FEATURE:
<223> OTHER INFORMATION: IgG1 HC2-HC3 T307P/L309Q/K409R

<400> SEQUENCE: 12

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 13
<211> LENGTH: 216
<212> TYPE: PRT
<213> ORGANISM: Artificial sequence
<220> FEATURE:
<223> OTHER INFORMATION: IgG1 HC2-HC3 T307P/L309Q/Q311R/K409R
```

<400> SEQUENCE: 13

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 14
<211> LENGTH: 216
<212> TYPE: PRT
<213> ORGANISM: Artificial sequence
<220> FEATURE:
<223> OTHER INFORMATION: IgG1 HC2-HC3 Q311K/ T366W

<400> SEQUENCE: 14

```
Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Lys
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Trp Cys Leu Val Lys Gly Phe Tyr Pro Ser
```

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 15
<211> LENGTH: 216
<212> TYPE: PRT
<213> ORGANISM: Artificial sequence
<220> FEATURE:
<223> OTHER INFORMATION: IgG1 HC2-HC3 Q311R/T366W

<400> SEQUENCE: 15

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Trp Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 16
<211> LENGTH: 216
<212> TYPE: PRT
<213> ORGANISM: Artificial sequence
<220> FEATURE:
<223> OTHER INFORMATION: IgG1 HC2-HC3 T307P/L309Q/ T366W

<400> SEQUENCE: 16

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
            35                  40                  45

Asp Gly Val Glu Val His Asn Ala Lys Thr Lys Pro Arg Glu Glu Gln
        50                  55                  60

Tyr Asn Ser Thr Tyr Arg Val Val Ser Val Leu Pro Val Gln His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Trp Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 17
<211> LENGTH: 216
<212> TYPE: PRT
<213> ORGANISM: Artificial sequence
<220> FEATURE:
<223> OTHER INFORMATION: IgG1 HC2-HC3 T307P/L309Q/Q311R/ T366W

<400> SEQUENCE: 17

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
            35                  40                  45

Asp Gly Val Glu Val His Asn Ala Lys Thr Lys Pro Arg Glu Glu Gln
        50                  55                  60

Tyr Asn Ser Thr Tyr Arg Val Val Ser Val Leu Pro Val Gln His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Trp Cys Leu Val Lys Gly Phe Tyr Pro Ser
        130                 135                 140

```
Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 18
<211> LENGTH: 216
<212> TYPE: PRT
<213> ORGANISM: Artificial sequence
<220> FEATURE:
<223> OTHER INFORMATION: IgG1 HC2-HC3 Q311K/T366S/L368A/Y407V

<400> SEQUENCE: 18

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Lys
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Ser Cys Ala Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Val
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 19
<211> LENGTH: 216
<212> TYPE: PRT
<213> ORGANISM: Artificial sequence
<220> FEATURE:
<223> OTHER INFORMATION: IgG1 HC2-HC3 Q311R/T366S/L368A/Y407V

<400> SEQUENCE: 19

Pro Glu Leu Leu Gly Gly Pro Ser Val Phe Leu Phe Pro Pro Lys Pro
1               5                   10                  15
```

```
Lys Asp Thr Leu Met Ile Ser Arg Thr Pro Glu Val Thr Cys Val Val
         20                  25                  30

Val Asp Val Ser His Glu Asp Pro Glu Val Lys Phe Asn Trp Tyr Val
             35                  40                  45

Asp Gly Val Glu Val His Asn Ala Lys Thr Lys Pro Arg Glu Glu Gln
 50                  55                  60

Tyr Asn Ser Thr Tyr Arg Val Val Ser Val Leu Thr Val Leu His Arg
 65                  70                  75                  80

Asp Trp Leu Asn Gly Lys Glu Tyr Lys Cys Lys Val Ser Asn Lys Ala
                 85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Ser Cys Ala Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Val
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 20
<211> LENGTH: 216
<212> TYPE: PRT
<213> ORGANISM: Artificial sequence
<220> FEATURE:
<223> OTHER INFORMATION: IgG1 HC2-HC3 T307P/L309Q/ T366S/L368A/Y407V

<400> SEQUENCE: 20

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
 50                  55                  60

Tyr Asn Ser Thr Tyr Arg Val Val Ser Val Leu Pro Val Gln His Gln
 65                  70                  75                  80

Asp Trp Leu Asn Gly Lys Glu Tyr Lys Cys Lys Val Ser Asn Lys Ala
                 85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Ser Cys Ala Val Lys Gly Phe Tyr Pro Ser
130                 135                 140

Asp Ile Ala Val Glu Trp Glu Ser Asn Gly Gln Pro Glu Asn Asn Tyr
145                 150                 155                 160
```

Lys Thr Thr Pro Pro Val Leu Asp Ser Asp Gly Ser Phe Phe Leu Val
            165                 170                 175

Ser Lys Leu Thr Val Asp Lys Ser Arg Trp Gln Gln Gly Asn Val Phe
        180                 185                 190

Ser Cys Ser Val Met His Glu Ala Leu His Asn His Tyr Thr Gln Lys
    195                 200                 205

Ser Leu Ser Leu Ser Pro Gly Lys
    210                 215

<210> SEQ ID NO 21
<211> LENGTH: 216
<212> TYPE: PRT
<213> ORGANISM: Artificial sequence
<220> FEATURE:
<223> OTHER INFORMATION: IgG1 HC2-HC3 T307P/L309Q/Q311R/
      T366S/L368A/Y407V

<400> SEQUENCE: 21

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Pro Val Gln His Arg
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Ser Cys Ala Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Val
            165                 170                 175

Ser Lys Leu Thr Val Asp Lys Ser Arg Trp Gln Gln Gly Asn Val Phe
        180                 185                 190

Ser Cys Ser Val Met His Glu Ala Leu His Asn His Tyr Thr Gln Lys
    195                 200                 205

Ser Leu Ser Leu Ser Pro Gly Lys
    210                 215

<210> SEQ ID NO 22
<211> LENGTH: 216
<212> TYPE: PRT
<213> ORGANISM: Homo sapiens

<400> SEQUENCE: 22

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

```
Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
 50                  55                  60

Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Ala
                 85                  90                  95

Leu Pro Ala Pro Ile Glu Lys Thr Ile Ser Lys Ala Lys Gly Gln Pro
             100                 105                 110

Arg Glu Pro Gln Val Tyr Thr Leu Pro Pro Ser Arg Glu Glu Met Thr
         115                 120                 125

Lys Asn Gln Val Ser Leu Thr Cys Leu Val Lys Gly Phe Tyr Pro Ser
 130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                 165                 170                 175

Ser Lys Leu Thr Val Asp Lys Ser Arg Trp Gln Gln Gly Asn Val Phe
             180                 185                 190

Ser Cys Ser Val Met His Glu Ala Leu His Asn His Tyr Thr Gln Lys
         195                 200                 205

Ser Leu Ser Leu Ser Pro Gly Lys
 210                 215

<210> SEQ ID NO 23
<211> LENGTH: 216
<212> TYPE: PRT
<213> ORGANISM: Artificial Sequence
<220> FEATURE:
<223> OTHER INFORMATION: IgG1 CH2-CH3 K409R

<400> SEQUENCE: 23

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
             20                  25                  30

Val Asp Val Ser His Glu Asp Pro Glu Val Lys Phe Asn Trp Tyr Val
         35                  40                  45

Asp Gly Val Glu Val His Asn Ala Lys Thr Lys Pro Arg Glu Glu Gln
 50                  55                  60

Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Ala
                 85                  90                  95

Leu Pro Ala Pro Ile Glu Lys Thr Ile Ser Lys Ala Lys Gly Gln Pro
             100                 105                 110

Arg Glu Pro Gln Val Tyr Thr Leu Pro Pro Ser Arg Glu Glu Met Thr
         115                 120                 125

Lys Asn Gln Val Ser Leu Thr Cys Leu Val Lys Gly Phe Tyr Pro Ser
 130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                 165                 170                 175
```

Ser Arg Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 24
<211> LENGTH: 216
<212> TYPE: PRT
<213> ORGANISM: Artificial Sequence
<220> FEATURE:
<223> OTHER INFORMATION: IgG1 CH2-CH3 F405L

<400> SEQUENCE: 24

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Leu Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 25
<211> LENGTH: 216
<212> TYPE: PRT
<213> ORGANISM: Artificial Sequence
<220> FEATURE:
<223> OTHER INFORMATION: IgG1 CH2-CH3 T366S/L368A/Y407V

<400> SEQUENCE: 25

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val

```
            35                  40                  45
Asp Gly Val Glu Val His Asn Ala Lys Thr Lys Pro Arg Glu Glu Gln
 50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Ser Cys Ala Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Val
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 26
<211> LENGTH: 216
<212> TYPE: PRT
<213> ORGANISM: Artificial Sequence
<220> FEATURE:
<223> OTHER INFORMATION: IgG1 CH2-CH3 T366W

<400> SEQUENCE: 26

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
 50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Trp Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
```

180                 185                 190
Ser Cys Ser Val Met His Glu Ala Leu His Asn His Tyr Thr Gln Lys
        195                 200                 205

Ser Leu Ser Leu Ser Pro Gly Lys
        210                 215

<210> SEQ ID NO 27
<211> LENGTH: 648
<212> TYPE: DNA
<213> ORGANISM: Artificial sequence
<220> FEATURE:
<223> OTHER INFORMATION: IgG1 CH2-CH3 Q311K

<400> SEQUENCE: 27
cctgaactgc tggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcacaag     240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa                648

<210> SEQ ID NO 28
<211> LENGTH: 648
<212> TYPE: DNA
<213> ORGANISM: Artificial sequence
<220> FEATURE:
<223> OTHER INFORMATION: IgG1 CH2-CH3 Q311R

<400> SEQUENCE: 28
cctgaactgc tggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcaccgg     240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa                648

<210> SEQ ID NO 29
<211> LENGTH: 648
<212> TYPE: DNA
<213> ORGANISM: Artificial sequence
<220> FEATURE:
<223> OTHER INFORMATION: IgG1 CH2-CH3 T307P/L309Q

<400> SEQUENCE: 29

```
cctgaactgc tgggggacc gtcagtcttc ctcttccccc caaaacccaa ggacaccctc      60
atgatctccc ggaccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcccgt ccagcaccag      240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa                 648
```

<210> SEQ ID NO 30
<211> LENGTH: 648
<212> TYPE: DNA
<213> ORGANISM: Artificial sequence
<220> FEATURE:
<223> OTHER INFORMATION: IgG1 CH2-CH3 T307P/L309Q/Q311R

<400> SEQUENCE: 30

```
cctgaactgc tgggggacc gtcagtcttc ctcttccccc caaaacccaa ggacaccctc      60
atgatctccc ggaccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcccgt ccagcaccgg      240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa                 648
```

<210> SEQ ID NO 31
<211> LENGTH: 648
<212> TYPE: DNA
<213> ORGANISM: Artificial sequence
<220> FEATURE:
<223> OTHER INFORMATION: IgG1 CH2-CH3 Q311K/F405L

<400> SEQUENCE: 31

```
cctgaactgc tgggggacc gtcagtcttc ctcttccccc caaaacccaa ggacaccctc      60
atgatctccc ggaccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcacaag     240
gactggctga atggcaagga gtacaagtgc aaggtctcca acaaagccct cccagccccc     300
atcgagaaaa ccatctccaa agccaaaggg cagccccgag aaccacaggt gtacaccctg     360
```

```
cccccatccc gggatgagct gaccaagaac caggtcagcc tgacctgcct ggtcaaaggc    420
ttctatccca gcgacatcgc cgtggagtgg gagagcaatg ggcagccgga gaacaactac    480
aagaccacgc ctcccgtgct ggactccgac ggctccttcc tgctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaa               648
```

<210> SEQ ID NO 32
<211> LENGTH: 648
<212> TYPE: DNA
<213> ORGANISM: Artificial sequence
<220> FEATURE:
<223> OTHER INFORMATION: IgG1 CH2-CH3 Q311R/F405L

<400> SEQUENCE: 32

```
cctgaactgc tgggggggacc gtcagtcttc ctcttccccc caaaacccaa ggacaccctc    60
atgatctccc ggacccctga ggtcacatgc gtggtggtgg acgtgagcca cgaagaccct    120
gaggtcaagt tcaactggta cgtggacggc gtggaggtgc ataatgccaa gacaaagccg    180
cgggaggagc agtacaacag cacgtaccgt gtggtcagcg tcctcaccgt cctgcaccgg    240
gactggctga atggcaagga gtacaagtgc aaggtctcca acaaagccct cccagccccc    300
atcgagaaaa ccatctccaa agccaaaggg cagccccgag aaccacaggt gtacaccctg    360
cccccatccc gggatgagct gaccaagaac caggtcagcc tgacctgcct ggtcaaaggc    420
ttctatccca gcgacatcgc cgtggagtgg gagagcaatg ggcagccgga gaacaactac    480
aagaccacgc ctcccgtgct ggactccgac ggctccttcc tgctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaa               648
```

<210> SEQ ID NO 33
<211> LENGTH: 648
<212> TYPE: DNA
<213> ORGANISM: Artificial sequence
<220> FEATURE:
<223> OTHER INFORMATION: IgG1 CH2-CH3 T307P/L309Q/F405L

<400> SEQUENCE: 33

```
cctgaactgc tgggggggacc gtcagtcttc ctcttccccc caaaacccaa ggacaccctc    60
atgatctccc ggacccctga ggtcacatgc gtggtggtgg acgtgagcca cgaagaccct    120
gaggtcaagt tcaactggta cgtggacggc gtggaggtgc ataatgccaa gacaaagccg    180
cgggaggagc agtacaacag cacgtaccgt gtggtcagcg tcctcccgt ccagcaccag    240 gactggctga atggcaagga gtacaagtgc aaggtctcca acaaagccct cccagccccc    300
atcgagaaaa ccatctccaa agccaaaggg cagccccgag aaccacaggt gtacaccctg    360
cccccatccc gggatgagct gaccaagaac caggtcagcc tgacctgcct ggtcaaaggc    420
ttctatccca gcgacatcgc cgtggagtgg gagagcaatg ggcagccgga gaacaactac    480
aagaccacgc ctcccgtgct ggactccgac ggctccttcc tgctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaa               648
```

<210> SEQ ID NO 34
<211> LENGTH: 648
<212> TYPE: DNA
<213> ORGANISM: Artificial sequence
<220> FEATURE:
<223> OTHER INFORMATION: IgG1 CH2-CH3 T307P/L309Q/Q311R/F405L

<400> SEQUENCE: 34

```
cctgaactgc tggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcccgt ccagcaccgg      240
gactggctga atggcaagga gtacaagtgc aaggtctcca acaaagccct cccagccccc     300
atcgagaaaa ccatctccaa agccaaaggg cagccccgag aaccacaggt gtacaccctg     360
ccccatccc gggatgagct gaccaagaac caggtcagcc tgacctgcct ggtcaaaggc      420
ttctatccca gcgacatcgc cgtggagtgg gagagcaatg ggcagccgga gaacaactac     480
aagaccacgc ctcccgtgct ggactccgac ggctccttcc tgctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa              648
```

<210> SEQ ID NO 35
<211> LENGTH: 648
<212> TYPE: DNA
<213> ORGANISM: Artificial sequence
<220> FEATURE:
<223> OTHER INFORMATION: IgG1 CH2-CH3 Q311K/K409R

<400> SEQUENCE: 35

```
cctgaactgc tggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcacaag     240
gactggctga atggcaagga gtacaagtgc aaggtctcca acaaagccct cccagccccc     300
atcgagaaaa ccatctccaa agccaaaggg cagccccgag aaccacaggt gtacaccctg     360
ccccatccc gggatgagct gaccaagaac caggtcagcc tgacctgcct ggtcaaaggc      420
ttctatccca gcgacatcgc cgtggagtgg gagagcaatg ggcagccgga gaacaactac     480
aagaccacgc ctcccgtgct ggactccgac ggctccttct tcctctacag ccggctcacc     540
gtggacaaga gcaggtggca gcaggggaac gtcttctcat gctccgtgat gcatgaggct     600
ctgcacaacc actacacgca gaagagcctc tccctgtctc cgggtaaa              648
```

<210> SEQ ID NO 36
<211> LENGTH: 648
<212> TYPE: DNA
<213> ORGANISM: Artificial sequence
<220> FEATURE:
<223> OTHER INFORMATION: IgG1 CH2-CH3 Q311R/K409R

<400> SEQUENCE: 36

```
cctgaactgc tggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcaccgg     240
gactggctga atggcaagga gtacaagtgc aaggtctcca acaaagccct cccagccccc     300
```

-continued

| | |
|---|---|
| atcgagaaaa ccatctccaa agccaaaggg cagccccgag aaccacaggt gtacaccctg | 360 |
| cccccatccc gggatgagct gaccaagaac caggtcagcc tgacctgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct tcctctacag ccggctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 37
<211> LENGTH: 648
<212> TYPE: DNA
<213> ORGANISM: Artificial sequence
<220> FEATURE:
<223> OTHER INFORMATION: IgG1 CH2-CH3 T307P/L309Q/K409R

<400> SEQUENCE: 37

| | |
|---|---|
| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcccgt ccagcaccag | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgacctgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct tcctctacag ccggctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 38
<211> LENGTH: 648
<212> TYPE: DNA
<213> ORGANISM: Artificial sequence
<220> FEATURE:
<223> OTHER INFORMATION: IgG1 CH2-CH3 T307P/L309Q/Q311R/K409R

<400> SEQUENCE: 38

| | |
|---|---|
| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcccgt ccagcaccgg | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgacctgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct tcctctacag ccggctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 39
<211> LENGTH: 648

<212> TYPE: DNA
<213> ORGANISM: Artificial sequence
<220> FEATURE:
<223> OTHER INFORMATION: IgG1 CH2-CH3 Q311K/ T366W

<400> SEQUENCE: 39

| | | |
|---|---|---|
| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcaccgt cctgcacaag | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgtggtgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct tcctctacag caagctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 40
<211> LENGTH: 648
<212> TYPE: DNA
<213> ORGANISM: Artificial sequence
<220> FEATURE:
<223> OTHER INFORMATION: IgG1 CH2-CH3 Q311R/T366W

<400> SEQUENCE: 40

| | | |
|---|---|---|
| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcaccgt cctgcaccgg | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgtggtgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct tcctctacag caagctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 41
<211> LENGTH: 648
<212> TYPE: DNA
<213> ORGANISM: Artificial sequence
<220> FEATURE:
<223> OTHER INFORMATION: IgG1 CH2-CH3 T307P/L309Q/ T366W

<400> SEQUENCE: 41

| | | |
|---|---|---|
| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcccgt ccagcaccag | 240 |

```
gactggctga atggcaagga gtacaagtgc aaggtctcca acaaagccct cccagccccc    300
atcgagaaaa ccatctccaa agccaaaggg cagccccgag aaccacaggt gtacaccctg    360 ccccatccc gggatgagct gaccaagaac caggtcagcc tgtggtgcct ggtcaaaggc    420
ttctatccca gcgacatcgc cgtggagtgg gagagcaatg ggcagccgga gaacaactac    480
aagaccacgc ctcccgtgct ggactccgac ggctccttct tcctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaa             648
```

```
<210> SEQ ID NO 42
<211> LENGTH: 648
<212> TYPE: DNA
<213> ORGANISM: Artificial sequence
<220> FEATURE:
<223> OTHER INFORMATION: IgG1 CH2-CH3 T307P/L309Q/Q311R/ T366W

<400> SEQUENCE: 42
cctgaactgc tgggggggacc gtcagtcttc ctcttccccc caaaacccaa ggacaccctc     60
atgatctccc ggaccctga ggtcacatgc gtggtggtgg acgtgagcca cgaagaccct    120
gaggtcaagt tcaactggta cgtggacggc gtggaggtgc ataatgccaa gacaaagccg    180
cgggaggagc agtacaacag cacgtaccgt gtggtcagcg tcctcccgt ccagcaccgg    240 gactggctga atggcaagga gtacaagtgc aaggtctcca acaaagccct cccagccccc    300
atcgagaaaa ccatctccaa agccaaaggg cagccccgag aaccacaggt gtacaccctg    360 ccccatccc gggatgagct gaccaagaac caggtcagcc tgtggtgcct ggtcaaaggc    420
ttctatccca gcgacatcgc cgtggagtgg gagagcaatg ggcagccgga gaacaactac    480
aagaccacgc ctcccgtgct ggactccgac ggctccttct tcctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaa             648
```

```
<210> SEQ ID NO 43
<211> LENGTH: 648
<212> TYPE: DNA
<213> ORGANISM: Artificial sequence
<220> FEATURE:
<223> OTHER INFORMATION: IgG1 CH2-CH3 Q311K/T366S/L368A/Y407V

<400> SEQUENCE: 43
cctgaactgc tgggggggacc gtcagtcttc ctcttccccc caaaacccaa ggacaccctc     60
atgatctccc ggaccctga ggtcacatgc gtggtggtgg acgtgagcca cgaagaccct    120
gaggtcaagt tcaactggta cgtggacggc gtggaggtgc ataatgccaa gacaaagccg    180
cgggaggagc agtacaacag cacgtaccgt gtggtcagcg tcctcaccgt cctgcacaag    240
gactggctga atggcaagga gtacaagtgc aaggtctcca acaaagccct cccagccccc    300
atcgagaaaa ccatctccaa agccaaaggg cagccccgag aaccacaggt gtacaccctg    360 ccccatccc gggatgagct gaccaagaac caggtcagcc tgagctgcgc cgtcaaaggc    420
ttctatccca gcgacatcgc cgtggagtgg gagagcaatg ggcagccgga gaacaactac    480
aagaccacgc ctcccgtgct ggactccgac ggctccttct tcctcgtgag caagctcacc    540
gtggacaaga gcaggtggca gcaggggaac gtcttctcat gctccgtgat gcatgaggct    600
ctgcacaacc actacacgca gaagagcctc tccctgtctc cgggtaaa             648
```

<210> SEQ ID NO 44
<211> LENGTH: 648
<212> TYPE: DNA
<213> ORGANISM: Artificial sequence
<220> FEATURE:
<223> OTHER INFORMATION: IgG1 CH2-CH3 Q311R/T366S/L368A/Y407V

<400> SEQUENCE: 44

```
cctgaactgc tgggggggacc gtcagtcttc ctcttccccc caaaacccaa ggacaccctc    60
atgatctccc ggaccctga ggtcacatgc gtggtggtgg acgtgagcca cgaagaccct   120
gaggtcaagt tcaactggta cgtggacggc gtggaggtgc ataatgccaa gacaaagccg   180
cgggaggagc agtacaacag cacgtaccgt gtggtcagcg tcctcaccgt cctgcaccgg   240
gactggctga atggcaagga gtacaagtgc aaggtctcca acaaagccct cccagccccc   300
atcgagaaaa ccatctccaa agccaaaggg cagccccgag aaccacaggt gtacaccctg   360
cccccatccc gggatgagct gaccaagaac caggtcagcc tgagctgcgc cgtcaaaggc   420
ttctatccca gcgacatcgc cgtggagtgg gagagcaatg ggcagccgga gaacaactac   480
aagaccacgc ctcccgtgct ggactccgac ggctccttct tcctcgtgag caagctcacc   540
gtggacaaga gcaggtggca gcaggggaac gtcttctcat gctccgtgat gcatgaggct   600
ctgcacaacc actacacgca gaagagcctc tccctgtctc cgggtaaa               648
```

<210> SEQ ID NO 45
<211> LENGTH: 648
<212> TYPE: DNA
<213> ORGANISM: Artificial sequence
<220> FEATURE:
<223> OTHER INFORMATION: IgG1 CH2-CH3 T307P/L309Q/ T366S/L368A/Y407V

<400> SEQUENCE: 45

```
cctgaactgc tgggggggacc gtcagtcttc ctcttccccc caaaacccaa ggacaccctc    60
atgatctccc ggaccctga ggtcacatgc gtggtggtgg acgtgagcca cgaagaccct   120
gaggtcaagt tcaactggta cgtggacggc gtggaggtgc ataatgccaa gacaaagccg   180
cgggaggagc agtacaacag cacgtaccgt gtggtcagcg tcctcccgt ccagcaccag   240
gactggctga atggcaagga gtacaagtgc aaggtctcca acaaagccct cccagccccc   300
atcgagaaaa ccatctccaa agccaaaggg cagccccgag aaccacaggt gtacaccctg   360
cccccatccc gggatgagct gaccaagaac caggtcagcc tgagctgcgc cgtcaaaggc   420
ttctatccca gcgacatcgc cgtggagtgg gagagcaatg ggcagccgga gaacaactac   480
aagaccacgc ctcccgtgct ggactccgac ggctccttct tcctcgtgag caagctcacc   540
gtggacaaga gcaggtggca gcaggggaac gtcttctcat gctccgtgat gcatgaggct   600
ctgcacaacc actacacgca gaagagcctc tccctgtctc cgggtaaa               648
```

<210> SEQ ID NO 46
<211> LENGTH: 648
<212> TYPE: DNA
<213> ORGANISM: Artificial sequence
<220> FEATURE:
<223> OTHER INFORMATION: IgG1 CH2-CH3 T307P/L309Q/Q311R/
     T366S/L368A/Y407V

<400> SEQUENCE: 46

```
cctgaactgc tgggggggacc gtcagtcttc ctcttccccc caaaacccaa ggacaccctc    60
atgatctccc ggaccctga ggtcacatgc gtggtggtgg acgtgagcca cgaagaccct   120
gaggtcaagt tcaactggta cgtggacggc gtggaggtgc ataatgccaa gacaaagccg   180
```

```
cgggaggagc agtacaacag cacgtaccgt gtggtcagcg tcctccccgt ccagcaccgg      240
gactggctga atggcaagga gtacaagtgc aaggtctcca acaaagccct cccagccccc      300
atcgagaaaa ccatctccaa agccaaaggg cagccccgag aaccacaggt gtacaccctg      360
cccccatccc gggatgagct gaccaagaac caggtcagcc tgagctgcgc cgtcaaaggc      420
ttctatccca gcgacatcgc cgtggagtgg gagagcaatg ggcagccgga gaacaactac      480
aagaccacgc ctcccgtgct ggactccgac ggctccttct tcctcgtgag caagctcacc      540
gtggacaaga gcaggtggca gcaggggaac gtcttctcat gctccgtgat gcatgaggct      600
ctgcacaacc actacacgca gaagagcctc tccctgtctc cgggtaaa                  648
```

<210> SEQ ID NO 47
<211> LENGTH: 648
<212> TYPE: DNA
<213> ORGANISM: Homo sapiens

<400> SEQUENCE: 47

```
cctgaactgc tgggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcaccag     240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag caagctcacc     540
gtggacaaga gcaggtggca gcaggggaac gtcttctcat gctccgtgat gcatgaggct     600
ctgcacaacc actacacgca gaagagcctc tccctgtctc cgggtaaa                  648
```

<210> SEQ ID NO 48
<211> LENGTH: 648
<212> TYPE: DNA
<213> ORGANISM: Artificial sequence
<220> FEATURE:
<223> OTHER INFORMATION: IgG1 CH2-CH3 K409R

<400> SEQUENCE: 48

```
cctgaactgc tgggggggacc gtcagtcttc ctcttccccc caaaacccaa ggacaccctc      60
atgatctccc ggacccctga ggtcacatgc gtggtggtgg acgtgagcca cgaagaccct     120
gaggtcaagt tcaactggta cgtggacggc gtggaggtgc ataatgccaa gacaaagccg     180
cgggaggagc agtacaacag cacgtaccgt gtggtcagcg tcctcaccgt cctgcaccag     240
gactggctga atggcaagga gtacaagtgc aaggtctcca acaaagccct cccagccccc     300
atcgagaaaa ccatctccaa agccaaaggg cagccccgag aaccacaggt gtacaccctg     360
cccccatccc gggatgagct gaccaagaac caggtcagcc tgacctgcct ggtcaaaggc     420
ttctatccca gcgacatcgc cgtggagtgg gagagcaatg ggcagccgga gaacaactac     480
aagaccacgc ctcccgtgct ggactccgac ggctccttct tcctctacag ccggctcacc     540
gtggacaaga gcaggtggca gcaggggaac gtcttctcat gctccgtgat gcatgaggct     600
ctgcacaacc actacacgca gaagagcctc tccctgtctc cgggtaaa                  648
```

<210> SEQ ID NO 49
<211> LENGTH: 648
<212> TYPE: DNA
<213> ORGANISM: Artificial sequence
<220> FEATURE:
<223> OTHER INFORMATION: IgG1 CH2-CH3 F405L

<400> SEQUENCE: 49

| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcaccgt cctgcaccag | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgacctgcct ggtcaaaggc | 420 |
| ttctatccca gcgacatcgc cgtggagtgg gagagcaatg ggcagccgga gaacaactac | 480 |
| aagaccacgc ctcccgtgct ggactccgac ggctccttcc tgctctacag caagctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 50
<211> LENGTH: 648
<212> TYPE: DNA
<213> ORGANISM: Artificial sequence
<220> FEATURE:
<223> OTHER INFORMATION: IgG1 CH2-CH3 T366S/L368A/Y407V

<400> SEQUENCE: 50

| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |
| cgggaggagc agtacaacag cacgtaccgt gtggtcagcg tcctcaccgt cctgcaccag | 240 |
| gactggctga atggcaagga gtacaagtgc aaggtctcca acaaagccct cccagccccc | 300 |
| atcgagaaaa ccatctccaa agccaaaggg cagccccgag aaccacaggt gtacaccctg | 360 |
| cccccatccc gggatgagct gaccaagaac caggtcagcc tgagctgcgc cgtcaaaggc | 420 |
| ttctatccca gcgacatcgc cgtggagtgg gagagcaatg ggcagccgga gaacaactac | 480 |
| aagaccacgc ctcccgtgct ggactccgac ggctccttct cctcgtgag caagctcacc | 540 |
| gtggacaaga gcaggtggca gcaggggaac gtcttctcat gctccgtgat gcatgaggct | 600 |
| ctgcacaacc actacacgca gaagagcctc tccctgtctc cgggtaaa | 648 |

<210> SEQ ID NO 51
<211> LENGTH: 648
<212> TYPE: DNA
<213> ORGANISM: Artificial sequence
<220> FEATURE:
<223> OTHER INFORMATION: IgG1 CH2-CH3 T366W

<400> SEQUENCE: 51

| cctgaactgc tggggggacc gtcagtcttc ctcttccccc caaaacccaa ggacaccctc | 60 |
| atgatctccc ggacccctga ggtcacatgc gtggtggtgg acgtgagcca cgaagaccct | 120 |
| gaggtcaagt tcaactggta cgtggacggc gtggaggtgc ataatgccaa gacaaagccg | 180 |

```
cgggaggagc agtacaacag cacgtaccgt gtggtcagcg tcctcaccgt cctgcaccag    240
gactggctga atggcaagga gtacaagtgc aaggtctcca acaaagccct cccagccccc    300
atcgagaaaa ccatctccaa agccaagggg cagccccgag aaccacaggt gtacaccctg    360
cccccatccc gggatgagct gaccaagaac caggtcagcc tgtggtgcct ggtcaaaggc    420
ttctatccca gcgacatcgc cgtggagtgg gagagcaatg ggcagccgga gaacaactac    480
aagaccacgc ctcccgtgct ggactccgac ggctccttct cctctacag caagctcacc    540 gtggacaaga gcaggtggca gcaggggaac gtcttctcat gctccgtgat gcatgaggct    600
ctgcacaacc actacacgca gaagagcctc tccctgtctc cgggtaaa               648
```

```
<210> SEQ ID NO 52
<211> LENGTH: 215
<212> TYPE: PRT
<213> ORGANISM: Artificial sequence
<220> FEATURE:
<223> OTHER INFORMATION: IgG2 CH2-CH3 Q311R

<400> SEQUENCE: 52
```

Pro Pro Val Ala Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Phe Arg Val Val Ser Val Leu Thr Val Val His Arg Asp
65                  70                  75                  80

Trp Leu Asn Gly Lys Glu Tyr Lys Cys Lys Val Ser Asn Lys Gly Leu
                85                  90                  95

Pro Ala Pro Ile Glu Lys Thr Ile Ser Lys Thr Lys Gly Gln Pro Arg
            100                 105                 110

Glu Pro Gln Val Tyr Thr Leu Pro Pro Ser Arg Glu Glu Met Thr Lys
        115                 120                 125

Asn Gln Val Ser Leu Thr Cys Leu Val Lys Gly Phe Tyr Pro Ser Asp
    130                 135                 140

Ile Ser Val Glu Trp Glu Ser Asn Gly Gln Pro Glu Asn Asn Tyr Lys
145                 150                 155                 160

Thr Thr Pro Pro Met Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
    210                 215

```
<210> SEQ ID NO 53
<211> LENGTH: 215
<212> TYPE: PRT
<213> ORGANISM: Artificial sequence
<220> FEATURE:
<223> OTHER INFORMATION: IgG2 CH2-CH3 T307P/V309Q/Q311R

<400> SEQUENCE: 53
```

```
Pro Pro Val Ala Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Gln Phe Asn Trp Tyr Val Asp
            35                  40                  45

Gly Val Glu Val His Asn Ala Lys Thr Lys Pro Arg Glu Glu Gln Phe
        50                  55                  60

Asn Ser Thr Phe Arg Val Val Ser Val Leu Pro Val Gln His Arg Asp
65                  70                  75                  80

Trp Leu Asn Gly Lys Glu Tyr Lys Cys Lys Val Ser Asn Lys Gly Leu
                85                  90                  95

Pro Ala Pro Ile Glu Lys Thr Ile Ser Lys Thr Lys Gly Gln Pro Arg
            100                 105                 110

Glu Pro Gln Val Tyr Thr Leu Pro Pro Ser Arg Glu Glu Met Thr Lys
            115                 120                 125

Asn Gln Val Ser Leu Thr Cys Leu Val Lys Gly Phe Tyr Pro Ser Asp
        130                 135                 140

Ile Ser Val Glu Trp Glu Ser Asn Gly Gln Pro Glu Asn Asn Tyr Lys
145                 150                 155                 160

Thr Thr Pro Pro Met Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
            195                 200                 205

Leu Ser Leu Ser Pro Gly Lys
        210                 215

<210> SEQ ID NO 54
<211> LENGTH: 215
<212> TYPE: PRT
<213> ORGANISM: Homo sapiens

<400> SEQUENCE: 54

Pro Pro Val Ala Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Gln Phe Asn Trp Tyr Val Asp
            35                  40                  45

Gly Val Glu Val His Asn Ala Lys Thr Lys Pro Arg Glu Glu Gln Phe
        50                  55                  60

Asn Ser Thr Phe Arg Val Val Ser Val Leu Thr Val Val His Gln Asp
65                  70                  75                  80

Trp Leu Asn Gly Lys Glu Tyr Lys Cys Lys Val Ser Asn Lys Gly Leu
                85                  90                  95

Pro Ala Pro Ile Glu Lys Thr Ile Ser Lys Thr Lys Gly Gln Pro Arg
            100                 105                 110

Glu Pro Gln Val Tyr Thr Leu Pro Pro Ser Arg Glu Glu Met Thr Lys
            115                 120                 125

Asn Gln Val Ser Leu Thr Cys Leu Val Lys Gly Phe Tyr Pro Ser Asp
        130                 135                 140

Ile Ser Val Glu Trp Glu Ser Asn Gly Gln Pro Glu Asn Asn Tyr Lys
145                 150                 155                 160
```

```
Thr Thr Pro Pro Met Leu Asp Ser Asp Gly Ser Phe Phe Leu Tyr Ser
            165                 170                 175

Lys Leu Thr Val Asp Lys Ser Arg Trp Gln Gln Gly Asn Val Phe Ser
        180                 185                 190

Cys Ser Val Met His Glu Ala Leu His Asn His Tyr Thr Gln Lys Ser
    195                 200                 205

Leu Ser Leu Ser Pro Gly Lys
    210             215

<210> SEQ ID NO 55
<211> LENGTH: 215
<212> TYPE: PRT
<213> ORGANISM: Artificial sequence
<220> FEATURE:
<223> OTHER INFORMATION: IgG2 F405L/K409R

<400> SEQUENCE: 55

Pro Pro Val Ala Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Phe Arg Val Val Ser Val Leu Thr Val Val His Gln Asp
65                  70                  75                  80

Trp Leu Asn Gly Lys Glu Tyr Lys Cys Lys Val Ser Asn Lys Gly Leu
                85                  90                  95

Pro Ala Pro Ile Glu Lys Thr Ile Ser Lys Thr Lys Gly Gln Pro Arg
            100                 105                 110

Glu Pro Gln Val Tyr Thr Leu Pro Pro Ser Arg Glu Glu Met Thr Lys
        115                 120                 125

Asn Gln Val Ser Leu Thr Cys Leu Val Lys Gly Phe Tyr Pro Ser Asp
    130                 135                 140

Ile Ser Val Glu Trp Glu Ser Asn Gly Gln Pro Glu Asn Asn Tyr Lys
145                 150                 155                 160

Thr Thr Pro Pro Met Leu Asp Ser Asp Gly Ser Phe Leu Leu Tyr Ser
            165                 170                 175

Arg Leu Thr Val Asp Lys Ser Arg Trp Gln Gln Gly Asn Val Phe Ser
        180                 185                 190

Cys Ser Val Met His Glu Ala Leu His Asn His Tyr Thr Gln Lys Ser
    195                 200                 205

Leu Ser Leu Ser Pro Gly Lys
    210             215

<210> SEQ ID NO 56
<211> LENGTH: 216
<212> TYPE: PRT
<213> ORGANISM: Artificial Sequence
<220> FEATURE:
<223> OTHER INFORMATION: IgG4 CH2-CH3 T307P/V309Q

<400> SEQUENCE: 56

Pro Glu Phe Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
```

```
                    20                  25                  30

Val Asp Val Ser Gln Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys Gly Gln Pro
            100                 105                 110

Arg Glu Pro Gln Val Tyr Thr Leu Pro Pro Ser Gln Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Glu Gly Asn Val Phe
            180                 185                 190

Ser Cys Ser Val Met His Glu Ala Leu His Asn His Tyr Thr Gln Lys
        195                 200                 205

Ser Leu Ser Leu Ser Leu Gly Lys
    210                 215

<210> SEQ ID NO 57
<211> LENGTH: 38
<212> TYPE: PRT
<213> ORGANISM: Artificial sequence
<220> FEATURE:
<223> OTHER INFORMATION: 1FU1 linker

<400> SEQUENCE: 57

Ala Ser Leu Asp Thr Thr Ala Glu Asn Gln Ala Lys Asn Glu His Leu
1               5                   10                  15

Gln Lys Glu Asn Glu Arg Leu Leu Arg Asp Trp Asn Asp Val Gln Gly
            20                  25                  30

Arg Phe Glu Lys Gly Ser
        35

<210> SEQ ID NO 58
<211> LENGTH: 30
<212> TYPE: PRT
<213> ORGANISM: Artificial sequence
<220> FEATURE:
<223> OTHER INFORMATION: 1DC1(13AA)2 linker

<400> SEQUENCE: 58

Ala Ser Glu Lys Asn Lys Arg Ser Thr Pro Tyr Ile Glu Arg Ala Glu
1               5                   10                  15

Lys Asn Lys Arg Ser Thr Pro Tyr Ile Glu Arg Ala Gly Ser
            20                  25                  30

<210> SEQ ID NO 59
<211> LENGTH: 43
<212> TYPE: PRT
<213> ORGANISM: Artificial sequence
<220> FEATURE:
```

-continued

<223> OTHER INFORMATION: 1DC1(13AA)3 linker

<400> SEQUENCE: 59

Ala Ser Glu Lys Asn Lys Arg Ser Thr Pro Tyr Ile Glu Arg Ala Glu
1               5                   10                  15

Lys Asn Lys Arg Ser Thr Pro Tyr Ile Glu Arg Ala Glu Lys Asn Lys
            20                  25                  30

Arg Ser Thr Pro Tyr Ile Glu Arg Ala Gly Ser
        35                  40

<210> SEQ ID NO 60
<211> LENGTH: 24
<212> TYPE: PRT
<213> ORGANISM: Artificial sequence
<220> FEATURE:
<223> OTHER INFORMATION: AS(AP)10GS  linker

<400> SEQUENCE: 60

Ala Ser Ala Pro Ala Pro Ala Pro Ala Pro Ala Pro Ala Pro Ala Pro
1               5                   10                  15

Ala Pro Ala Pro Ala Pro Gly Ser
            20

<210> SEQ ID NO 61
<211> LENGTH: 44
<212> TYPE: PRT
<213> ORGANISM: Artificial sequence
<220> FEATURE:
<223> OTHER INFORMATION: AS(AP)20GS  linker

<400> SEQUENCE: 61

Ala Ser Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Gly Ser
        35                  40

<210> SEQ ID NO 62
<211> LENGTH: 26
<212> TYPE: PRT
<213> ORGANISM: Artificial sequence
<220> FEATURE:
<223> OTHER INFORMATION: (EAAAK)4 linker

<400> SEQUENCE: 62

Ala Ser Ala Glu Ala Ala Ala Lys Glu Ala Ala Ala Lys Glu Ala Ala
1               5                   10                  15

Ala Lys Glu Ala Ala Ala Lys Ala Gly Ser
            20                  25

<210> SEQ ID NO 63
<211> LENGTH: 46
<212> TYPE: PRT
<213> ORGANISM: Artificial sequence
<220> FEATURE:
<223> OTHER INFORMATION: (EAAAK)8 linker

<400> SEQUENCE: 63

Ala Ser Ala Glu Ala Ala Ala Lys Glu Ala Ala Ala Lys Glu Ala Ala
1               5                   10                  15

Ala Lys Glu Ala Ala Ala Lys Glu Ala Ala Ala Lys Glu Ala Ala Ala
            20                  25                  30

Lys Glu Ala Ala Ala Lys Glu Ala Ala Ala Lys Ala Gly Ser
            35                  40                  45

<210> SEQ ID NO 64
<211> LENGTH: 22
<212> TYPE: PRT
<213> ORGANISM: Artificial sequence
<220> FEATURE:
<223> OTHER INFORMATION: GS(G4S)4 linker

<400> SEQUENCE: 64

Gly Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 65
<211> LENGTH: 42
<212> TYPE: PRT
<213> ORGANISM: Artificial sequence
<220> FEATURE:
<223> OTHER INFORMATION: GS(G4S)8 linker

<400> SEQUENCE: 65

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
            35                  40

<210> SEQ ID NO 66
<211> LENGTH: 62
<212> TYPE: PRT
<213> ORGANISM: Artificial sequence
<220> FEATURE:
<223> OTHER INFORMATION: GS12X(G4S) linker

<400> SEQUENCE: 66

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
            35                  40                  45

Gly Gly Gly Ser Gly Gly Gly Gly Ser Gly Gly Gly Gly Ser
        50                  55                  60

<210> SEQ ID NO 67
<211> LENGTH: 82
<212> TYPE: PRT
<213> ORGANISM: Artificial sequence
<220> FEATURE:
<223> OTHER INFORMATION: GS16X(G4S) linker

<400> SEQUENCE: 67

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
            35                  40                  45

-continued

```
Gly Gly Gly Ser Gly Gly Gly Ser Gly Gly Gly Ser Gly Gly
        50                  55                  60

Gly Gly Ser Gly Gly Gly Ser Gly Gly Gly Ser Gly Gly Gly
 65                  70                  75                  80

Gly Ser

<210> SEQ ID NO 68
<211> LENGTH: 457
<212> TYPE: PRT
<213> ORGANISM: Artificial sequence
<220> FEATURE:
<223> OTHER INFORMATION: gp120-R HC (K409R)

<400> SEQUENCE: 68

Gln Val Gln Leu Val Gln Ser Gly Ala Glu Val Lys Lys Pro Gly Ala
 1               5                  10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320
```

```
Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 69
<211> LENGTH: 215
<212> TYPE: PRT
<213> ORGANISM: Artificial sequence
<220> FEATURE:
<223> OTHER INFORMATION: gp120-R LC

<400> SEQUENCE: 69

```
Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 70
<211> LENGTH: 450
<212> TYPE: PRT
<213> ORGANISM: Artificial sequence
<220> FEATURE:
<223> OTHER INFORMATION: anti-RSV-L HC (F405L)

<400> SEQUENCE: 70

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 71
<211> LENGTH: 218
<212> TYPE: PRT
<213> ORGANISM: Artificial sequence
<220> FEATURE:
<223> OTHER INFORMATION: anti-RSV LC

<400> SEQUENCE: 71

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
                20                  25                  30

Gly Ile Ser Tyr Met His Trp Tyr Gln Gln Lys Pro Gly Gln Pro Pro
            35                  40                  45

Lys Leu Leu Ile Tyr Ala Ala Ser Asn Pro Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 72
<211> LENGTH: 450
<212> TYPE: PRT
<213> ORGANISM: Artificial sequence
<220> FEATURE:
<223> OTHER INFORMATION: RSV-L[Q311A] HC (Q311A/ F405L)

<400> SEQUENCE: 72
```

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Ala Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 73
<211> LENGTH: 450
<212> TYPE: PRT
<213> ORGANISM: Artificial sequence
<220> FEATURE:
<223> OTHER INFORMATION: RSV-L[Q311K] HC (Q311K/ F405L)

<400> SEQUENCE: 73

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Lys Asp Trp Leu Asn Gly Lys
305                 310                 315                 320
```

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 74
<211> LENGTH: 450
<212> TYPE: PRT
<213> ORGANISM: Artificial sequence
<220> FEATURE:
<223> OTHER INFORMATION: RSV-L[Q311K] HC (Q311R/ F405L)

<400> SEQUENCE: 74

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser

-continued

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Arg Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 75
<211> LENGTH: 450
<212> TYPE: PRT
<213> ORGANISM: Artificial sequence
<220> FEATURE:
<223> OTHER INFORMATION: RSV-L[Q311K] HC (Q311H/ F405L)

<400> SEQUENCE: 75

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Leu Tyr Gly Phe Thr Tyr Gly Phe Ala Tyr Trp Gly Gln
        100                 105                 110

Gly Thr Leu Val Thr Val Ser Ser Ala Ser Thr Lys Gly Pro Ser Val
    115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 76
<211> LENGTH: 450
<212> TYPE: PRT
<213> ORGANISM: Artificial sequence
<220> FEATURE:
<223> OTHER INFORMATION: RSV-L[TL] HC (T307P/L309Q/ F405L)

<400> SEQUENCE: 76

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30
```

```
Gly Met Gly Val Ser Trp Ile Arg Gln Pro Pro Gly Lys Ala Leu Glu
         35                  40                  45
Trp Leu Ala His Ile Tyr Trp Asp Asp Lys Arg Tyr Asn Pro Ser
 50                  55                  60
Leu Lys Ser Arg Leu Thr Ile Thr Lys Asp Thr Ser Lys Asn Gln Val
 65                  70                  75                  80
Val Leu Thr Met Thr Asn Met Asp Pro Val Asp Thr Ala Thr Tyr Tyr
                 85                  90                  95
Cys Ala Arg Leu Tyr Gly Phe Thr Tyr Gly Phe Ala Tyr Trp Gly Gln
             100                 105                 110
Gly Thr Leu Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
             130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
             195                 200                 205
Pro Ser Asn Thr Lys Val Asp Lys Lys Val Glu Pro Lys Ser Cys Asp
             210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
290                 295                 300
Val Val Ser Val Leu Pro Val Gln His Gln Asp Trp Leu Asn Gly Lys
305                 310                 315                 320
Glu Tyr Lys Cys Lys Val Ser Asn Lys Ala Leu Pro Ala Pro Ile Glu
             325                 330                 335
Lys Thr Ile Ser Lys Ala Lys Gly Gln Pro Arg Glu Pro Gln Val Tyr
             340                 345                 350
Thr Leu Pro Pro Ser Arg Asp Glu Leu Thr Lys Asn Gln Val Ser Leu
             355                 360                 365
Thr Cys Leu Val Lys Gly Phe Tyr Pro Ser Asp Ile Ala Val Glu Trp
             370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Leu Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
             435                 440                 445
Gly Lys
```

<210> SEQ ID NO 77
<211> LENGTH: 450
<212> TYPE: PRT
<213> ORGANISM: Artificial sequence
<220> FEATURE:
<223> OTHER INFORMATION: RSV-L[TLQ] HC (T307P/L309Q/Q311R/F405L)

<400> SEQUENCE: 77

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Pro Val Gln His Arg Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Leu Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450

<210> SEQ ID NO 78
<211> LENGTH: 450
<212> TYPE: PRT
<213> ORGANISM: Artificial sequence
<220> FEATURE:
<223> OTHER INFORMATION: RSV-L[I253D] HC (I253D/F405L)

<400> SEQUENCE: 78

Gln Ile Thr Leu Lys Glu Ser Gly Pro Thr Leu Val Lys Pro Thr Gln
1               5                   10                  15
Thr Leu Thr Leu Thr Cys Thr Phe

```
                   260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Leu Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 79
<211> LENGTH: 449
<212> TYPE: PRT
<213> ORGANISM: Artificial sequence
<220> FEATURE:
<223> OTHER INFORMATION: aVb5 HC

<400> SEQUENCE: 79

Gln Val Gln Leu Val Glu Ser Gly Gly Gly Val Val Gln Pro Gly Arg
1               5                   10                  15
Ser Arg Arg Leu Ser Cys Ala Ala Ser Gly Phe Thr Phe Ser Arg Tyr
            20                  25                  30
Thr Met His Trp Val Arg Gln Ala Pro Gly Lys Gly Leu Glu Trp Val
        35                  40                  45
Ala Val Ile Ser Phe Asp Gly Ser Asn Lys Tyr Tyr Val Gly Ser Val
    50                  55                  60
Lys Gly Arg Phe Thr Ile Ser Arg Asp Asn Ser Glu Asn Thr Leu Tyr
65                  70                  75                  80
Leu Gln Val Asn Ile Leu Arg Ala Glu Asp Thr Ala Val Tyr Tyr Cys
                85                  90                  95
Ala Arg Glu Ala Arg Gly Ser Tyr Ala Phe Asp Ile Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
```

```
            165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 80
<211> LENGTH: 215
<212> TYPE: PRT
<213> ORGANISM: Artificial sequence
<220> FEATURE:
<223> OTHER INFORMATION: anti-TNF and anti-aVb5 LC

<400> SEQUENCE: 80

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Pro Pro
                85                  90                  95
Phe Thr Phe Gly Pro Gly Thr Lys Val Asp Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 81
<211> LENGTH: 456
<212> TYPE: PRT
<213> ORGANISM: Artificial sequence
<220> FEATURE:
<223> OTHER INFORMATION: TNF HC

<400> SEQUENCE: 81

Glu Val Gln Leu Val Glu Ser Gly Gly Gly Val Val Gln Pro Gly Gly
1               5                   10                  15
Ser Leu Ser Leu Ser Cys Ala Ala Ser Gly Phe Ile Phe Ser Ser Tyr
            20                  25                  30
Ala Met His Trp Val Arg Gln Ala Pro Gly Asn Gly Leu Glu Trp Val
        35                  40                  45
Ala Phe Met Ser Tyr Asp Gly Ser Asn Lys Lys Tyr Ala Asp Ser Val
    50                  55                  60
Lys Gly Arg Phe Thr Ile Ser Arg Asp Asn Ser Glu Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Gly Ile Ala Ala Gly Gly Asn Tyr Tyr Tyr Tyr Gly
            100                 105                 110
Met Asp Val Trp Gly Gln Gly Thr Thr Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
```

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 82
<211> LENGTH: 456
<212> TYPE: PRT
<213> ORGANISM: Artificial sequence
<220> FEATURE:
<223> OTHER INFORMATION: TNF-[Q311R] HC

<400> SEQUENCE: 82

Glu Val Gln Leu Val Glu Ser Gly Gly Gly Val Val Gln Pro Gly Gly
1               5                   10                  15

Ser Leu Ser Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Arg
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 83
<211> LENGTH: 456
<212> TYPE: PRT
<213> ORGANISM: Artificial sequence
<220> FEATURE:
<223> OTHER INFORMATION: TNF-[TLQ] HC (T307P/L309Q/Q311R)

<400> SEQUENCE: 83

Glu Val Gln Leu Val Glu Ser Gly Gly Gly Val Val Gln Pro Gly Gly
1               5                   10                  15

Ser Leu Ser Leu Ser Cys Ala Ala Ser Gly Phe Ile Phe Ser Ser Tyr
            20                  25                  30

-continued

```
Ala Met His Trp Val Arg Gln Ala Pro Gly Asn Gly Leu Glu Trp Val
        35                  40                  45
Ala Phe Met Ser Tyr Asp Gly Ser Asn Lys Lys Tyr Ala Asp Ser Val
 50                  55                  60
Lys Gly Arg Phe Thr Ile Ser Arg Asp Asn Ser Glu Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Asp Arg Gly Ile Ala Ala Gly Gly Asn Tyr Tyr Tyr Tyr Gly
            100                 105                 110
Met Asp Val Trp Gly Gln Gly Thr Thr Val Thr Val Ser Ser Ala Ser
            115                 120                 125
Thr Lys Gly Pro Ser Val Phe Pro Leu Ala Pro Ser Ser Lys Ser Thr
        130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Pro Val Gln His Arg
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
        355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
```

```
Ser Leu Ser Leu Ser Pro Gly Lys
    450                 455
```

<210> SEQ ID NO 84
<211> LENGTH: 456
<212> TYPE: PRT
<213> ORGANISM: Artificial sequence
<220> FEATURE:
<223> OTHER INFORMATION: TNF-knob[Q311R] HC (Q311R/T366W)

<400> SEQUENCE: 84

```
Glu Val Gln Leu Val Glu Ser Gly Gly Gly Val Val Gln Pro Gly Gly
1               5                   10                  15

Ser Leu Ser Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Arg
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350
```

```
Arg Glu Pro Gln Val Tyr Thr Leu Pro Pro Ser Arg Glu Met Thr
            355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 85
<211> LENGTH: 456
<212> TYPE: PRT
<213> ORGANISM: Artificial sequence
<220> FEATURE:
<223> OTHER INFORMATION: TNF-knob[TLQ] HC (T307P/L309Q/Q311R/T366W)

<400> SEQUENCE: 85

Glu Val Gln Leu Val Glu Ser Gly Gly Gly Val Val Gln Pro Gly Gly
1               5                   10                  15

Ser Leu Ser Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255
```

-continued

```
Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Pro Val Gln His Arg
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Trp Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 86
<211> LENGTH: 449
<212> TYPE: PRT
<213> ORGANISM: Artificial sequence
<220> FEATURE:
<223> OTHER INFORMATION: aVb5-hole HC (T366S/L368A/Y407V)

<400> SEQUENCE: 86

```
Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Gly Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

| | | | | | | | | | | | |
|---|---|---|---|---|---|---|---|---|---|---|---|
|Asn|Ser|Gly|Ala|Leu|Thr|Ser|Gly|Val|His|Thr|Phe|Pro|Ala|Val|Leu|
| | | |165| | | |170| | | |175|

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 87
<211> LENGTH: 645
<212> TYPE: DNA
<213> ORGANISM: Artificial sequence
<220> FEATURE:
<223> OTHER INFORMATION: IgG2 CH2-CH3 Q311R

<400> SEQUENCE: 87
ccacctgtgg caggaccgtc agtcttcctc ttccccccaa acccaaggac acccctcatg      60
atctcccgga cccctgaggt cacgtgcgtg gtggtggacg tgagccacga agaccccgag     120
gtccagttca actggtacgt ggacggcgtg gaggtgcata atgccaagac aaagccacgg     180
gaggagcagt tcaacagcac gttccgtgtg gtcagcgtcc tcaccgttgt gcaccgggac     240
tggctgaacg gcaaggagta caagtgcaag gtctccaaca aaggcctccc agcccccatc     300
gagaaaacca tctccaaaac caagggcagc cccgagaaca cacaggtgta caccctgccc     360
ccatcccggg aggagatgac caagaaccag gtcagcctga cctgcctggt caaaggcttc     420

```
tacccccagcg acatcgccgt ggagtgggag agcaatgggc agccggagaa caactacaag        480
accacacctc ccatgctgga ctccgacggc tccttcttcc tctacagcaa gctcaccgtg        540
gacaagagca ggtggcagca ggggaacgtc ttctcatgct ccgtgatgca tgaggctctg        600
cacaaccact acacgcagaa gagcctctcc ctgtctccgg gtaaa                        645
```

<210> SEQ ID NO 88
<211> LENGTH: 645
<212> TYPE: DNA
<213> ORGANISM: Artificial sequence
<220> FEATURE:
<223> OTHER INFORMATION: IgG2 CH2-CH3 T307P/V309Q/Q311R

<400> SEQUENCE: 88

```
ccacctgtgg caggaccgtc agtcttcctc ttcccccccaa acccaaggga caccctcatg         60
atctcccgga cccctgaggt cacgtgcgtg gtggtggacg tgagccacga agaccccgag        120
gtccagttca actggtacgt ggacggcgtg gaggtgcata atgccaagac aaagccacgg        180
gaggagcagt tcaacagcac gttccgtgtg gtcagcgtcc tccccgttca gcaccgggac        240
tggctgaacg gcaaggagta caagtgcaag gtctccaaca aaggcctccc agcccccatc        300
gagaaaacca tctccaaaac caaagggcag ccccgagaac acaggtgta caccctgccc        360 ccatcccggg aggagatgac caagaaccag gtcagcctga cctgcctggt caaaggcttc        420
taccccagcg acatcgccgt ggagtgggag agcaatgggc agccggagaa caactacaag        480
accacacctc ccatgctgga ctccgacggc tccttcttcc tctacagcaa gctcaccgtg        540
gacaagagca ggtggcagca ggggaacgtc ttctcatgct ccgtgatgca tgaggctctg        600
cacaaccact acacgcagaa gagcctctcc ctgtctccgg gtaaa                        645
```

<210> SEQ ID NO 89
<211> LENGTH: 645
<212> TYPE: DNA
<213> ORGANISM: Homo sapiens

<400> SEQUENCE: 89

```
ccacctgtgg caggaccgtc agtcttcctc ttcccccccaa acccaaggga caccctcatg         60
atctcccgga cccctgaggt cacgtgcgtg gtggtggacg tgagccacga agaccccgag        120
gtccagttca actggtacgt ggacggcgtg gaggtgcata atgccaagac aaagccacgg        180
gaggagcagt tcaacagcac gttccgtgtg gtcagcgtcc tcaccgttgt gcaccaggac        240
tggctgaacg gcaaggagta caagtgcaag gtctccaaca aaggcctccc agcccccatc        300
gagaaaacca tctccaaaac caaagggcag ccccgagaac acaggtgta caccctgccc        360 ccatcccggg aggagatgac caagaaccag gtcagcctga cctgcctggt caaaggcttc        420
taccccagcg acatcgccgt ggagtgggag agcaatgggc agccggagaa caactacaag        480
accacacctc ccatgctgga ctccgacggc tccttcttcc tctacagcaa gctcaccgtg        540
gacaagagca ggtggcagca ggggaacgtc ttctcatgct ccgtgatgca tgaggctctg        600
cacaaccact acacgcagaa gagcctctcc ctgtctccgg gtaaa                        645
```

<210> SEQ ID NO 90
<211> LENGTH: 645
<212> TYPE: DNA
<213> ORGANISM: Artificial sequence
<220> FEATURE:
<223> OTHER INFORMATION: IgG2 F405L/K409R -continued

```
<400> SEQUENCE: 90
ccacctgtgg caggaccgtc agtcttcctc ttccccccaa acccaagga caccctcatg    60
atctcccgga cccctgaggt cacgtgcgtg gtggtggacg tgagccacga agaccccgag   120
gtccagttca actggtacgt ggacggcgtg gaggtgcata atgccaagac aaagccacgg   180
gaggagcagt tcaacagcac gttccgtgtg gtcagcgtcc tcaccgttgt gcaccaggac   240
tggctgaacg gcaaggagta caagtgcaag gtctccaaca aaggcctccc agcccccatc   300
gagaaaacca tctccaaaac caaagggcag ccccgagaac acaggtgta caccctgccc   360
ccatcccggg aggagatgac caagaaccag gtcagcctga cctgcctggt caaaggcttc   420
taccccagcg acatcgccgt ggagtgggag agcaatgggc agccggagaa caactacaag   480
accacacctc ccatgctgga ctccgacggc tccttcctgc tctacagccg gctcaccgtg   540
gacaagagca ggtggcagca ggggaacgtc ttctcatgct ccgtgatgca tgaggctctg   600
cacaaccact acacgcagaa gagcctctcc ctgtctccgg gtaaa              645

<210> SEQ ID NO 91
<211> LENGTH: 645
<212> TYPE: DNA
<213> ORGANISM: Artificial sequence
<220> FEATURE:
<223> OTHER INFORMATION: IgG4 CH2-CH3 T307P/V309Q

<400> SEQUENCE: 91
ccacctgtgg caggaccgtc agtcttcctc ttccccccaa acccaagga caccctcatg    60
atctcccgga cccctgaggt cacgtgcgtg gtggtggacg tgagccacga agaccccgag   120
gtccagttca actggtacgt ggacggcgtg gaggtgcata atgccaagac aaagccacgg   180
gaggagcagt tcaacagcac gttccgtgtg gtcagcgtcc tccccgttca gcaccaggac   240
tggctgaacg gcaaggagta caagtgcaag gtctccaaca aaggcctccc agcccccatc   300
gagaaaacca tctccaaaac caaagggcag ccccgagaac acaggtgta caccctgccc   360
ccatcccggg aggagatgac caagaaccag gtcagcctga cctgcctggt caaaggcttc   420
taccccagcg acatcgccgt ggagtgggag agcaatgggc agccggagaa caactacaag   480
accacacctc ccatgctgga ctccgacggc tccttcttcc tctacagcaa gctcaccgtg   540
gacaagagca ggtggcagca ggggaacgtc ttctcatgct ccgtgatgca tgaggctctg   600
cacaaccact acacgcagaa gagcctctcc ctgtctccgg gtaaa              645

<210> SEQ ID NO 92
<211> LENGTH: 10
<212> TYPE: PRT
<213> ORGANISM: Homo sapiens

<400> SEQUENCE: 92

Glu Pro Lys Ser Cys Asp Lys Thr His Thr
1               5                   10

<210> SEQ ID NO 93
<211> LENGTH: 7
<212> TYPE: PRT
<213> ORGANISM: Homo sapiens

<400> SEQUENCE: 93

Glu Arg Lys Cys Cys Val Glu
1               5
```

```
<210> SEQ ID NO 94
<211> LENGTH: 12
<212> TYPE: PRT
<213> ORGANISM: Homo sapiens

<400> SEQUENCE: 94

Glu Leu Lys Thr Pro Leu Gly Asp Thr Thr His Thr
1               5                   10

<210> SEQ ID NO 95
<211> LENGTH: 5
<212> TYPE: PRT
<213> ORGANISM: Homo sapiens

<400> SEQUENCE: 95

Glu Ser Lys Tyr Gly
1               5

<210> SEQ ID NO 96
<211> LENGTH: 10
<212> TYPE: PRT
<213> ORGANISM: Artificial sequence
<220> FEATURE:
<223> OTHER INFORMATION: IgG1 engineered hinge

<400> SEQUENCE: 96

Glu Pro Lys Ser Ser Asp Lys Thr His Thr
1               5                   10

<210> SEQ ID NO 97
<211> LENGTH: 18
<212> TYPE: PRT
<213> ORGANISM: Homo sapiens

<400> SEQUENCE: 97

Pro Ser Thr Pro Pro Thr Pro Ser Pro Ser Thr Pro Pro Thr Pro Ser
1               5                   10                  15

Pro Ser

<210> SEQ ID NO 98
<211> LENGTH: 22
<212> TYPE: PRT
<213> ORGANISM: Homo sapiens

<400> SEQUENCE: 98

Gly Gly Glu Glu Lys Lys Lys Glu Lys Glu Lys Glu Glu Gln Glu Glu
1               5                   10                  15

Arg Glu Thr Lys Thr Pro
            20

<210> SEQ ID NO 99
<211> LENGTH: 34
<212> TYPE: PRT
<213> ORGANISM: Artificial Sequence
<220> FEATURE:
<223> OTHER INFORMATION: engineered Z domain

<400> SEQUENCE: 99

Phe Asn Met Gln Cys Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp Cys
```

<210> SEQ ID NO 100
<211> LENGTH: 58
<212> TYPE: PRT
<213> ORGANISM: Artificial Sequence
<220> FEATURE:
<223> OTHER INFORMATION: engineered Z domain

<400> SEQUENCE: 100

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 101
<211> LENGTH: 33
<212> TYPE: PRT
<213> ORGANISM: Artificial Sequence
<220> FEATURE:
<223> OTHER INFORMATION: engineered Z domain

<400> SEQUENCE: 101

```
Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp
```

<210> SEQ ID NO 102
<211> LENGTH: 4
<212> TYPE: PRT
<213> ORGANISM: Homo sapiens

<400> SEQUENCE: 102

```
Ile Gln Arg Thr
1
```

<210> SEQ ID NO 103
<211> LENGTH: 23
<212> TYPE: PRT
<213> ORGANISM: Homo sapiens

<400> SEQUENCE: 103

```
Leu Asn Gly Glu Glu Phe Met Asp Phe Asp Leu Lys Gln Gly Thr Trp
1               5                   10                  15

Gly Gly Asp Trp Pro Glu Ala
            20
```

<210> SEQ ID NO 104
<211> LENGTH: 11
<212> TYPE: PRT
<213> ORGANISM: Homo sapiens

<400> SEQUENCE: 104

```
Val Leu Thr Val Leu His Gln Asp Trp Leu Asn
1               5                   10
```

<210> SEQ ID NO 105
<211> LENGTH: 11

```
<212> TYPE: PRT
<213> ORGANISM: Mus musculus

<400> SEQUENCE: 105

Ala Leu Pro Ile Gln His Gln Asp Trp Met Ser
1               5                   10
```

ENGINEERED MULTISPECIFIC ANTIBODIES AND OTHER MULTIMERIC PROTEINS WITH ASYMMETRICAL CH2-CH3 REGION MUTATIONS

CROSS-REFERENCE TO RELATED APPLICATIONS

This application claims the benefit of U.S. Provisional Application Ser. No. 62/515,316, filed 5 Jun. 2017, the entire contents of which are incorporated herein by reference.

FIELD OF THE INVENTION

The present invention relates to engineered multispecific antibodies and other multimeric proteins with asymmetrical CH2-CH3 region mutations and methods of making and using them.

SEQUENCE LISTING

This application contains a Sequence Listing submitted via EFS-Web, the entire content of which is incorporated herein by reference. The ASCII text file, created on 29 May 2018, is named JBI5124USNP_ST25.txt and is 164 kilobytes in size.

BACKGROUND OF THE INVENTION

Therapeutic biologics programs are increasingly turning to bispecific antibodies for dual-targeting, cell redirection efforts, and immune checkpoint modulation; indeed many bispecific therapeutics are currently in clinical trials (Jachimowicz et al. *BioDrugs*. 2014 (4):331-43). The development of bispecific antibodies has been limited by the difficulty of both upstream and downstream processes, being able to generate high titers and pure product in a reproducible and scalable manner, and separating bispecific molecules from excess parental or intermediate molecules. Methods for specifically pairing IgG heavy chains or half molecules have been developed, and include knob-in-holes, controlled Fab arm exchange, CrossMAb, and common light chains and orthogonal Fab interface. Production of Fv-based molecules (i.e. BiTEs, Diabodies) and non-IgG based scaffolds (i.e. DARPins, Adnectins, fynomers, and centyrins) have increased interest in developing these molecules as therapeutics.

A disadvantage of Fv-only or alternative scaffold-based molecules is their typically shorter serum lifetimes resulting from urinary excretion or from lysosomal degradation due to their inability to be recycled by FcRn. Thus, IgG-based multispecific molecules containing an intact Fc domain are attractive based on their longer serum half-lives, ability to facilitate effector functions, and induction of apoptotic pathways.

Purification of bispecific antibodies can be challenging due to the multiple steps required to remove residual parental and other intermediate mAbs and Ab fragment molecules. Such molecules can have biophysical characteristics that are similar to the derived bispecific antibodies and thus cannot be easily separated by chromatographic methods. This difficulty in purification can lead to either a decrease in yield or purity of the bispecific molecule.

Therefore, there remains need for alternative bispecific and multispecific formats and method for purification of bispecific and multispecific molecules such as antibodies.

BRIEF SUMMARY OF THE INVENTION

The invention provides for an isolated multispecific antibody comprising a first CH2-CH3 region comprising a mutation Q311R, Q311K, T307P/L309Q, T307P/V309Q, T307P/L309Q/Q311R or T307P/V309Q/Q311R and a second CH2-CH3 region comprising a wild-type amino acid residue at positions 307, 309 and 311, wherein residue numbering is according to the EU Index.

The invention also provides for an isolated multispecific antibody comprising a first CH2-CH3 region comprising a mutation Q311R and a second CH2-CH3 region comprising a wild-type amino acid residue at position 311, wherein residue numbering is according to the EU Index.

The invention also provides for an isolated multispecific antibody comprising a first CH2-CH3 region comprising a mutation Q311K and a second CH2-CH3 region comprising a wild-type amino acid residue at position 311, wherein residue numbering is according to the EU Index.

The invention also provides for an isolated multispecific antibody comprising a first CH2-CH3 region comprising a mutation T307P/L309Q and a second CH2-CH3 region comprising a wild-type amino acid residue at positions 307 and 309, wherein residue numbering is according to the EU Index.

The invention also provides for an isolated multispecific antibody comprising a first CH2-CH3 region comprising a mutation T307P/V309Q and a second CH2-CH3 region comprising a wild-type amino acid residue at positions 307 and 309, wherein residue numbering is according to the EU Index.

The invention also provides for an isolated multispecific antibody comprising a first CH2-CH3 region comprising a mutation T307P/L309Q/Q311R and a second CH2-CH3 region comprising a wild-type amino acid residue at positions 307, 309 and 311, wherein residue numbering is according to the EU Index.

The invention also provides for an isolated multispecific antibody comprising a first CH2-CH3 region comprising a mutation T307P/V309Q/Q311R and a second CH2-CH3 region comprising a wild-type amino acid residue at positions 307, 309 and 311, wherein residue numbering is according to the EU Index.

The invention also provides for an isolated polynucleotide
comprising the polynucleotide encoding the first CH2-CH3 region comprising a mutation Q311R, Q311K, T307P/L309Q, T307P/V309Q, T307P/L309Q/Q311R or T307P/V309Q/Q311R;
comprising the polynucleotide encoding the first CH2-CH3 region comprising a mutation Q311R, Q311K, T307P/L309Q, T307P/V309Q, T307P/L309Q/Q311R or T307P/V309Q/Q311R and the second CH2-CH3 region comprising a wild-type amino acid residue at positions 307, 309 and 311; or
comprising a polynucleotide sequence of SEQ ID NOs: 27, 28, 29, 30, 31, 32, 33, 34, 35, 36, 37, 38, 39, 40, 41, 42, 43, 44, 45, 46, 87, 88 or 91.

The invention also provides for a vector comprising
the isolated polynucleotide encoding the first CH2-CH3 region comprising a mutation Q311R, Q311K, T307P/L309Q, T307P/V309Q, T307P/L309Q/Q311R or T307P/V309Q/Q311R;
the isolated polynucleotide comprising a polynucleotide sequence of SEQ ID NOs: 27, 28, 29, 30, 31, 32, 33, 34, 35, 36, 37, 38, 39, 40, 41, 42, 43, 44, 45, 46, 87, 88 or 91;
the isolated polynucleotide comprising the polynucleotide encoding the first CH2-CH3 region comprising a mutation Q311R, Q311K, T307P/L309Q, T307P/V309Q, T307P/ L309Q/Q311R or T307P/V309Q/Q311R and the second CH2-CH3 region comprising a wild-type amino acid residue at positions 307, 309 and 311; or the isolated polynucleotide comprising
SEQ ID NOs: 27, and 47, respectively;
SEQ ID NOs: 28 and 47, respectively;
SEQ ID NOs: 29 and 47, respectively;
SEQ ID NOs: 30 and 47, respectively;
SEQ ID NOs: 31 and 48, respectively;
SEQ ID NOs: 32 and 48, respectively;
SEQ ID NOs: 33 and 48, respectively;
SEQ ID NOs: 34 and 48, respectively;
SEQ ID NOs: 35 and 49, respectively;
SEQ ID NOs: 36 and 49, respectively;
SEQ ID NOs: 37 and 49, respectively;
SEQ ID NOs: 38 and 49, respectively;
SEQ ID NOs: 39 and 50, respectively;
SEQ ID NOs: 40 and 50, respectively;
SEQ ID NOs: 41 and 50, respectively;
SEQ ID NOs: 42 and 50, respectively;
SEQ ID NOs: 43 and 51, respectively;
SEQ ID NOs: 44 and 51, respectively;
SEQ ID NOs: 45 and 51, respectively;
SEQ ID NOs: 46 and 51, respectively;
SEQ ID NOs: 87 and 89, respectively;
SEQ ID Nos: 87 and 90, respectively;
SEQ ID NOs: 88 and 89, respectively;
SEQ ID Nos: 88 and 90, respectively;
SEQ ID Nos: 92 and 89, respectively; or
SEQ ID Nos: 92 and 90, respectively.

The invention also provides for a host cell comprising the vector of the invention.

The invention also provides for a method of making the isolated multispecific antibody of the invention, comprising
culturing the host cell of the invention under conditions that the multispecific antibody is expressed; and
purifying the multispecific antibody using protein A ligand affinity chromatography.

The invention also provides for a method of making an isolated multispecific antibody comprising a first heavy chain comprising a mutation Q311R, Q311K, T307P/ L309Q, T307P/V309Q, T307P/L309Q/Q311R or T307P/ V309Q/Q311R and a second heavy chain comprising wild-type amino acid residue at positions 307, 309 and 311, comprising
providing a first parental antibody comprising the first heavy chain comprising the mutation Q311R, Q311K, T307P/L309Q, T307P/V309Q, T307P/L309Q/Q311R or T307P/V309Q/Q311R and a first light chain;
providing a second parental antibody comprising the second heavy chain comprising wild-type amino acid residue at positions 307, 309 and 311 and a second light chain; contacting the first parental antibody and the second parental antibody in a sample; incubating the sample; and
purifying the multispecific antibody using protein A ligand affinity chromatography.

The invention also provides for an isolated antibody comprising two heavy chains or fragments thereof having identical amino acid sequences and two light chains or fragments thereof, wherein the two heavy chains comprise a mutation Q311R, Q311K, T307P/L309Q, T307P/V309Q, T307P/L309Q/Q311R or T307P/V309Q/Q311R, wherein residue numbering is according to the EU Index.

The invention also provides for a polynucleotide
encoding the antibody heavy chain comprising the CH2-CH3 region of SEQ ID NOs: 2, 3, 4, 5, 6, 7, 8, 9, 10, 11, 12, 13, 14, 15, 16, 17, 18, 19, 20, 21, 52, 53 or 56; or
comprising the polynucleotide sequence of SEQ ID NOs: 27, 28, 29, 30, 31, 32, 33, 34, 35, 36, 37, 38, 39, 40, 41, 42, 43, 44, 45, 46, 87, 88 or 91.

The invention also provides for a multimeric protein comprising a first polypeptide and a second polypeptide, wherein the first polypeptide comprises a first CH2-CH3 region comprising a mutation Q311R, Q311K, T307P/ L309Q, T307P/V309Q, T307P/L309Q/Q311R or T307P/ V309Q/Q311R and the second polypeptide comprises a second CH2-CH3 region comprising a wild-type amino acid residue at positions 307, 309 and 311, wherein residue numbering is according to the EU Index.

The invention also provides for pharmaceutical composition comprising the multimeric protein of the invention.

The invention also provides for a method of making an isolated multimeric protein comprising a first CH2-CH3 region comprising a mutation Q311R, Q311K, T307P/ L309Q, T307P/V309Q, T307P/L309Q/Q311R or T307P/ V309Q/Q311R and a second CH2-CH3 region comprising a wild-type amino acid residue at positions 307, 309 and 311, comprising
providing a first parental protein comprising the first CH2-CH3 region comprising the mutation Q311R, Q311K, T307P/L309Q, T307P/V309Q, T307P/L309Q/ Q311R or T307P/V309Q/Q311R;
providing a second parental protein comprising the second CH2-CH3 region comprising the wild-type amino acid residue at positions 307, 309 and 311;
contacting the first parental protein and the second parental protein in a sample;
incubating the sample; and
purifying the multispecific protein using protein A ligand affinity chromatography.

BRIEF DESCRIPTION OF THE DRAWINGS

FIG. 1A shows the alignment between human IgG1 and mouse IgG2a CH2 domains from amino acid residues 305 to 315; residue numbering according to the EU Index.

FIG. 3C shows a dose response curve of competition binding of indicated monospecific or bispecific antibodies with the mAb RSV-L for FcγRIIb using AlphaScreen assay. The graph displays % maximum signal plotted vs concentration of competitor.

FIG. 3D shows a dose response curve of competition binding of indicated monospecific or bispecific antibodies with the mAb RSV-L for FcγRIIIa using AlphaScreen assay. The graph displays % maximum signal plotted vs concentration of competitor.

FIG. 4A shows hydrophobic interaction chromatography (HIC) chromatogram demonstrating that a bispecific antibody can be separated from parental monospecific mAbs under conditions developed.

FIG. 5B shows HIC analyses of protein A affinity column pH 4.7 eluates of a sample from in-supernatant Fab arm exchanged bsRSV-L[TLQ].

FIG. 5C shows HIC analyses of protein A affinity column pH 4.2 eluates of a sample from in-supernatant Fab arm exchanged bsRSV-L[TLQ].

FIG. 5D shows HIC analyses of protein A affinity column pH 3.4 eluates of a sample from in-supernatant Fab arm exchanged bsRSV-L[TLQ].

FIG. 6B shows HIC analyses of protein A affinity column pH 4.6 eluates of a sample from in-supernatant Fab arm exchanged bsRSV-L[Q311R].

FIG. 6D shows HIC analyses of protein A affinity column pH 3.4 eluates of a sample from in-supernatant Fab arm exchanged bsRSV-L[Q311R].

FIG. 8 shows the pharmacokinetic analysis of indicated antibodies in Tg32 hemizygous mice. The graph displays the concentration of each mAb normalized to the initial time point of the linear phase plotted vs time. Each point represents mean±standard error of four animals per group.

DETAILED DESCRIPTION OF THE INVENTION

Figure 1B:
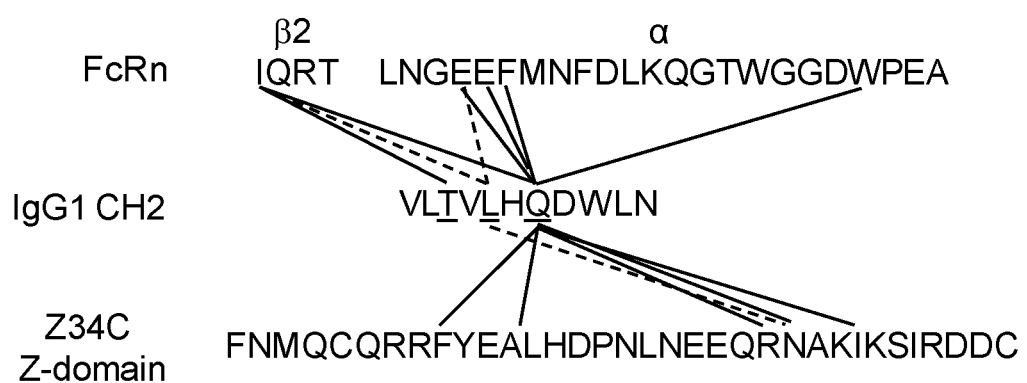
FIG. 1B shows the interactions of IgG1 CH2 residues T307, L309, and Q311 (underlined residues in the Figure) with FcRn or Z-domain (Z34C peptide). Each residue made side-chain interactions with residues in FcRn and with Z-domain. T307 interacted with I1 on the β2 microglobulin domain of FcRn. L309 and Q311R were responsible for interactions with both FcRn and Z-domain (dashed and solid lines for L309 and Q311, respectively). IQRT: SEQ ID NO: 102 (portion of β2 chain of FcRn); LNGEEFMDFDLKQGTWGGDWPEA: SEQ ID NO: 103 (portion of α chain of FcRn); VLTVLHQDWLN: SEQ ID NO: 104 (portion of IgG1 CH2 domain); FNMQCQRRF-YEALHDPNLNEEQRNAKIKSIRDDC: SEQ ID NO: 99.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

Definitions

As used in this specification and the appended claims, the singular forms "a," "an," and "the" include plural referents unless the content clearly dictates otherwise. Thus, for example, reference to "a cell" includes a combination of two or more cells, and the like.

"Multimeric protein" refers to a protein that is composed of two or more separate polypeptide chains that combine to form a single protein. The polypeptide chains may be coupled non-covalently or covalently for example via disulfide bonds.

"Bind" refers to specific binding of two proteins, such as binding of an antibody to an antigen or binding of a multispecific protein to its ligand. "Specific binding" refers to preferential binding of the two proteins with typically an equilibrium dissociation constant ($K_D$) of about $1 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred-fold less than its $K_D$ for binding to a non-specific antigen (e.g., BSA, casein).

"Reduced binding" refers to a measurable reduction in binding of the antibodies or the multispecific proteins of the invention having at least one mutation in the CH2-CH3 region to protein A ligand when compared to the binding of the parental molecule without the mutation.

"Modulates binding" refers to a measurable difference in binding of the antibodies or the multispecific proteins of the invention having at least one mutation in the CH2-CH3 region to FcγR or FcRn.

"Antigen" refers to a molecule, such as protein or a fragment of a protein that is capable of mounting an immune response in a subject.

"Asymmetric stabilizing mutations" refers to mutations in a first CH2-CH3 region and in a second CH2-CH3 region which are at different positions in the first and in the second CH2-CH3 region and favor (e.g. stabilize) heterodimer formation between the first CH2-CH3 region and the second CH2-CH3 region over homodimer formation between the first CH2-CH3 region or the second CH2-CH3 region.

"Heterologous protein" refers to a polypeptide or protein that is not naturally part or portion of a polypeptide comprising a CH2-CH3 region in an endogenous cell.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, *Proc Nat Acad Sci USA* 89:8990-8994, 1992; Meinke et al., *J Bacteriol* 175:1910-1918, 1993; Watanabe et al., *J Biol Chem* 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10). FN3 domains can ben engineered to bind an antigen with high specificity and affinity.

"Fynomer" refers to an antigen-binding protein derived from human Fyn SH3 domain that can be engineered to bind an antigen with high specificity and affinity.

"Antibodies" is meant in a broad sense and includes immunoglobulin molecules including monoclonal antibodies including murine, rabbit, human, humanized and chimeric monoclonal antibodies, antigen-binding fragments, monospecific, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (for example IgM). Each heavy chain is comprised of a heavy chain variable region (VH) and a heavy chain constant region (comprised of domains CH1, hinge CH2 and CH3). Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-terminus to carboxyl-terminus in the following order: FR1, CDR1, FR2, CDR2, FR3, CDR3, and FR4.

"Complementarity determining regions (CDR)" are regions in an antibody that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu and Kabat, *J Exp Med* 132:211-250, 1970; Kabat et al., Sequences of Proteins of Immunological Interest, 5th Ed. Public Health Service, National Institutes of Health, Bethesda, Md., 1991), Chothia (Chothia and Lesk, *J Mol Biol* 196: 901-917, 1987) and IMGT (Lefranc et al., *Dev Comp Immunol* 27:55-77, 2003). The correspondence between the various delineations and variable region numbering are described (see e.g. Lefranc et al., *Dev Comp Immunol* 27: 55-77, 2003; Honegger and Pluckthun, *J Mol Biol* 309:657-70, 2001; International ImMunoGeneTics (IMGT) database; Web resources, http://www imgt org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant region amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant regions.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"CH2-CH3 region" refers to a portion of a human antibody constant domain and includes amino acid residues 231-446 (residue numbering according to the EU Index). The CH2-CH3 region may have the C-terminal lysine at position 447 deleted.

"Monoclonal antibody" refers to an antibody population with single amino acid composition in each heavy and each light chain, except for possible well known alterations such as removal of C-terminal lysine from the antibody heavy chain. Monoclonal antibodies typically specifically bind one antigenic epitope, except that bispecific or multispecific monoclonal antibodies specifically bind two or more distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Humanized antibody" refers to an antibody in which CDR sequences are derived from non-human species and the frameworks are derived from human immunoglobulin sequences. Humanized antibody may include substitutions in the framework so that the framework may not be an exact copy of expressed human immunoglobulin or human immunoglobulin germline gene sequences.

"Human antibody" refers to an antibody that is optimized to have minimal immune response when administered to a human subject. Variable regions of human antibody are derived from human germline immunoglobulin sequences. If the antibody contains a constant region or a portion of the constant region, the constant region is also derived from human germline immunoglobulin sequences.

Human antibody comprises heavy or light chain variable regions that are "derived from" human germline immunoglobulin sequences if the variable regions of the antibody are obtained from a system that uses human germline immunoglobulin genes. Such exemplary systems are human immunoglobulin gene libraries displayed on phage or mammalian cells, and transgenic non-human animals such as mice or rats carrying human immunoglobulin loci. "Human antibody" typically contains amino acid differences when compared to the immunoglobulins expressed in humans due to, for example introduction of somatic mutations, intentional introduction of substitutions into the framework or CDRs, and amino acid changes introduced during cloning and VJD recombination in non-human animals "Human antibody" is typically about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin sequences. In some cases, "human antibody" may contain consensus framework sequences derived from human framework sequence analyses, for example as described in Knappik et al., *J Mol Biol* 296: 57-86, 2000, or synthetic HCDR3 incorporated into human immunoglobulin gene libraries displayed on phage, for example as described in Shi et al., *J Mol Biol* 397: 385-396, 2010 and in Int. Patent Publ. No. WO2009/085462. Antibodies in which CDRs are derived from a non-human species are not included in the definition of "human antibody".

"Recombinant" refers to antibodies and other proteins that are prepared, expressed, created or isolated by recombinant means.

"Multispecific" refers to a protein, such as an antibody, that specifically binds two or more distinct antigens or two or more distinct epitopes within the same antigen. Multispecific protein may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Bispecific" refers to a protein, such as an antibody, that specifically binds two distinct antigens or two distinct epitopes within the same antigen. Bispecific protein may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Monospecific" refers to a protein, such as an antibody, that specifically binds one distinct antigen or a distinct epitope. Monospecific protein may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems "Protein A ligand affinity chromatography" refers to an affinity chromatographic method that makes use of the affinity of the IgG binding domains of Protein A ligand for the Fc region of an immunoglobulin molecule. This Fc region comprises human or animal immunoglobulin constant domains CH2 and CH3 or immunoglobulin domains substantially similar to these. Protein A ligand encompasses native protein A from the cell wall of *Staphylococcus aureus*, Protein A produced by recombinant or synthetic methods, and variants that retain the ability to bind to the Fc region. In practice, Protein A ligand chromatography involves using Protein A ligand immobilized to a solid support. See Gagnon, Protein A Affinity Chromatography, Purification Tools for Monoclonal Antibodies, pp. 155-198, Validated Biosystems, 1996. The solid support is a non-aqueous matrix onto which Protein A ligand adheres. Such well-known supports include agarose, sepharose, glass, silica, polystyrene, nitrocellulose, charcoal, sand, cellulose and any other suitable material. Any suitable well-known method can be used to affix the second protein to the solid support. Such solid supports, with and without immobilized Protein A ligand, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden), Pall (Port Washington, N.Y.) and EMD-Millipore (Billerica, Mass.). Protein A ligand immobilized to a pore glass matrix is commercially available as PROSEP®-A (Millipore). The solid phase may also be an agarose-based matrix. Protein A ligand immobilized on an agarose matrix is commercially available as MABSELECT™ (Amersham Biosciences).

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a synthetic polynucleotide.

"Polypeptide" or "protein" refers to a molecule that comprises at least two amino acid residues linked by a peptide bond to form a polypeptide Small polypeptides of less than 50 amino acids may be referred to as "peptides".

"Variant" refers to a polypeptide or a polynucleotide that differs from a reference polypeptide or a reference polynucleotide by one or more modifications, for example one or more substitutions, insertions or deletions.

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Protein A ligand" refers to a naturally occurring or modified Staphylococcal Protein A, and includes engineered Protein A domains. Engineered Protein A may be, for example, Z-domain, variants of Z-domain, Y-domain, or an engineered Protein A that lacks D and E domains. Engineered Protein A domains may be unable to bind (or bind with very low affinity if at all) to the VH3 domain of an immunoglobulin, but can still bind to the CH2-CH3 region of IgG1, IgG2 and IgG4.

"Z-domain" is a synthetic engineered variant of B domain of *Staphylococcus aureus* protein A having mutations A1V and G29A when compared to the wild-type B domain of protein A. Z-domain comprises the amino acid sequence of SEQ ID NO: 1. Additional Z-domain variants are variants having the amino acid sequences of SEQ ID NOs: 99, 100 and 101, and those described in US2006/0194950.

```
                                              SEQ ID NO: 1
VDNKFNKEQQNAFYEILHLPNLNEEQRNAFIQSLKDDPSQSANLLAEAKK
LNDAQAPK

SEQ ID NO: 99
FNMQCQRRFYEALHDPNLNEEQRNAKIKSIRDDC

SEQ ID NO: 100
VDNKFNKEQQNAFYEILHLPNLNEEQRNAFIQSLKDDPSQSANLLAEAKK
LNDAQAPK

SEQ ID NO: 101
FNMQQQRRFYEALHDPNLNEEQRNAKIKSIRDD
```

The numbering of amino acid residues in the antibody constant region throughout the specification is according to the EU Index as described in Kabat et al., Sequences of Proteins of Immunological Interest, 5th Ed. Public Health Service, National Institutes of Health, Bethesda, Md. (1991), unless otherwise explicitly stated. Correspondence between various constant domain numbering systems is available at International ImMunoGeneTics (IMGT) database; Web resources, http://www imgt org).

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter: Multispecific Antibodies

The invention provides multispecific antibodies and other multimeric CH2-CH3 region containing proteins having asymmetric mutations in the CH2-CH3 region which facilitate their purification using protein A ligand chromatography, polynucleotides encoding them, vectors and host cells, and methods of making and using them.

Production and purification of full length bispecific therapeutic antibodies require efficient separation of the bispecific antibodies from excess parental and/or intermediate molecules. Fc mutations have been identified herein which reduce binding of the mutated heavy chain to protein A ligand. Bispecific antibodies having these Fc mutations in asymmetric manner (e.g. in one heavy chain only) can therefore be purified from the parental antibodies based on their differential elution profile from protein A ligand affinity columns Various methods for specifically pairing IgG heavy chains or half molecules have been developed, and include knob-in-holes (see e.g. U.S. Pat. No. 7,695,936) CrossMAb (Schaefer et al., *Proc Natl Acad Sci USA* 108:11187-11192, 2011), controlled Fab arm exchange (Labrijn et al., *Proc Natl Acad Sci USA* 110:5145-5150, 2013), common light chains (see e.g. U.S. Pat. No. 7,951,917) and orthogonal Fab interface (Lewis et al., *Nat Biotechnol* 32:191-198, 2014). The compositions and methods described herein provide further improved methods for generating and purifying bispecific antibodies.

FcRn is responsible for the transfer of maternal IgG to the fetus and for protecting serum IgG from lysosomal degradation. Both of these processes depend on the ability of FcRn to bind with $K_D$~600 nM to IgG at acidic pH (<6.5) in the recycling endosome and to dissociate at neutral pH, releasing the IgG back into the serum (Roopenian and Akilesh, *Nat Rev Immunol* 7: 715-725, 2007). IgG binds FcRn at the CH2-CH3 interface, such that a single Fc contains two identical FcRn binding sites. Structural and biochemical studies showed that a single Fc binds two FcRn heterodimers, although endocytic trafficking may involve multimerization of FcRn itself on membrane surfaces. Several studies have shown that modulating the interaction between the Fc and FcRn strongly impacts serum lifetime (Dall'Acqua et al., *J Immunol* 169: 5171-5180, 2002; Hinton et al., *J Biol Chem* 279(8): 6213-6216, 2004; Hinton et al., *J Immunol* 176: 346-356, 2006; Vaccaro et al., *Nat Biotechnol* 23: 1283-1288, 2005; Yeung et al., *J Immunol* 182: 7663-7671, 2009; Stapleton et al., *Nat Commun* 2: 599, 2011) leading to the conclusion that FcRn is primarily responsible for determining serum lifetime of IgG in adults.

Efforts to modulate protein A ligand binding characteristics of Abs are often associated with significantly decreased serum half-lives since both protein A and the neonatal Fc receptor (FcRn) share a binding site on the Fc. The mutations introduced herein do not reduce binding of the Fc to FcRn and therefore do not reduce serum half-life of the engineered antibodies. One of the introduced mutations, Q311R, resulted in slightly enhanced binding to FcRn and increased serum half-life of the antibody.

While the examples describe successful engineering and purification of multispecific full length antibodies from parental antibodies, the technology described herein is applicable to any multimeric protein that contains two CH2-CH3 regions.

The invention provides for an isolated multispecific antibody comprising a first CH2-CH3 region comprising a mutation Q311R, Q311K, T307P/L309Q, T307P/V309Q, T307P/L309Q/Q311R or T307P/V309Q/Q311R and a second CH2-CH3 region comprising a wild-type amino acid residue at positions 307, 309 and 311, wherein residue numbering is according to the EU Index.

The isolated multispecific antibody with asymmetric Q311R, Q311K, T307P/L309Q, T307P/V309Q, T307P/L309Q/Q311R or T307P/V309Q/Q311R mutations can be efficiently purified from parental antibodies using protein A ligand affinity chromatography. The introduced Q311K, T307P/L309Q and T307P/L309Q/Q311R mutations do not reduce binding of the engineered antibodies to FcRn or FcγR, and hence are not expected to alter antibody half-life or effector functions. The introduced Q311R mutation enhanced binding to FcRn and serum half-life of the antibody.

The invention also provides for an isolated multispecific antibody comprising a first CH2-CH3 region comprising a mutation Q311R and a second CH2-CH3 region comprising a wild-type amino acid residue at position 311, wherein residue numbering is according to the EU Index.

The invention also provides for an isolated multispecific antibody comprising a first CH2-CH3 region comprising a mutation Q311K and a second CH2-CH3 region comprising a wild-type amino acid residue at position 311, wherein residue numbering is according to the EU Index.

The invention also provides for an isolated multispecific antibody comprising a first CH2-CH3 region comprising a mutation T307P/L309Q and a second CH2-CH3 region comprising a wild-type amino acid residue at positions 307 and 309, wherein residue numbering is according to the EU Index.

The invention also provides for an isolated multispecific antibody comprising a first CH2-CH3 region comprising a mutation T307P/V309Q and a second CH2-CH3 region comprising a wild-type amino acid residue at positions 307 and 309, wherein residue numbering is according to the EU Index.

The invention also provides for an isolated multispecific antibody comprising a first CH2-CH3 region comprising a mutation T307P/L309Q/Q311R and a second CH2-CH3 region comprising a wild-type amino acid residue at positions 307, 309 and 311, wherein residue numbering is according to the EU Index.

The invention also provides for an isolated multispecific antibody comprising a first CH2-CH3 region comprising a mutation T307P/V309Q/Q311R and a second CH2-CH3 region comprising a wild-type amino acid residue at positions 307, 309 and 311, wherein residue numbering is according to the EU Index.

In some embodiments, the first CH2-CH3 region has reduced binding to protein A ligand when compared to the second CH2-CH3 region.

Binding to protein A ligand may be determined experimentally using any suitable method. Such methods may utilize ProteOn™ XPR36, Biacore 3000 or KinExA instrumentation. The measured affinity may vary if measured under different conditions (e.g., osmolarity, pH). Thus, measurements of affinity and other binding parameters (e.g., $K_D$, $k_{on}$, $k_{off}$) are typically made with standardized conditions and a standardized buffer, such as the buffer described herein. Alternatively, binding to protein A ligand may be assessed directly using protein A ligand chromatography using a pH gradient. Molecules with reduced binding to protein A ligand elute at higher pH. An exemplary protein A ligand chromatography may use mAbSelect Sure column (GE Healthcare) and the samples are eluted in 3 steps using buffers containing 50 mM citrate at pH of about pH4.7, pH 4.2 or pH 3.4.

In some embodiments, protein A ligand comprises Staphylococcal Protein A.

In some embodiments, protein A ligand comprises Z-domain.

In some embodiments, Z-domain comprises an amino acid sequence of SEQ ID NO: 1.

In some embodiments, protein A ligand comprises Y-domain.

In some embodiments, protein A ligand comprises an amino acid sequence of SEQ ID NO: 99.

In some embodiments, protein A ligand comprises an amino acid sequence of SEQ ID NO: 100.

In some embodiments, protein A ligand comprises an amino acid sequence of SEQ ID NO: 101.

Staphylococcal protein A (spA) contains 5 homologous helical IgG-binding domains, denoted E, D, A, B, and C (Uhlen, Guss et al. 1984). Each of these domains is sufficient to bind to the Fc region however spA also binds to the VH region of human VH3-family members (Romagnani et al., *J Immunol* 129:596-602, 1982; Sasso et al., *J Immunol* 147: 1877-1883, 1991). Stability-enhancing mutations introduced into the spA B domain or C domain led to a synthetic Z-domain and Y-domain, respectively, which are resistant to high pH treatment and bind only Fc. Tandem or tetrameric Z-domains, tetrameric Y-domains or native spA have been incorporated into commercial affinity resins such as Mab-Select SuRe (GE), TOYOPEARL AF-rProtein A HC-650F and MabSelect Xtra.

In some embodiments, the multispecific antibody is an IgG1 isotype.

In some embodiments, the multispecific antibody is an IgG2 isotype.

In some embodiments, the multispecific antibody is an IgG4 isotype.

While the examples provide experimental data on successful generation and purification of IgG1 multispecific antibodies, it is expected that the identified mutations will also be functional on IgG2 and IgG4 isotypes as residues 307 and 311 are conserved across all three isotypes and position 309 is conserved between IgG1 and IgG4 with a conservative Leu to Val substitution in IgG2.

In some embodiments, binding of the multispecific antibody to FcγR is comparable to that of the parental antibody without the mutation.

In some embodiments, FcγR is FcγRI, FcγRIIa, FcγRIIb. and/or FcγRIIIa.

In some embodiments, FcγR is FcγRI.
In some embodiments, FcγR is FcγRIIa.
In some embodiments, FcγR is FcγRIIb.
In some embodiments, FcγR is FcγRIIIa.

Exemplary multispecific antibodies with comparable binding to FcγR are multispecific antibodies with Q311R or T307P/L309Q/Q311R mutations.

In some embodiments, binding of the multispecific antibody to FcRn is comparable to that of the parental antibody without the mutation.

Exemplary multispecific antibodies with comparable binding to FcRn are multispecific antibodies with Q311K or T307P/L309Q/Q311R mutations.

In some embodiments, binding of the multispecific antibody to FcRn is enhanced when compared to binding of the parental antibody without the mutation to FcRn.

Exemplary multispecific antibodies with enhanced binding to FcRn are antibodies with Q311R mutation.

The invention also provides for an isolated multispecific antibody comprising a first CH2-CH3 region comprising a mutation Q311R, Q311K, T307P/L309Q, T307P/V309Q, T307P/L309Q/Q311R or T307P/V309Q/Q311R and a second CH2-CH3 region comprising a wild-type amino acid residue at positions 307, 309 and 311, wherein residue numbering is according to the EU Index, wherein the multispecific antibody further comprises asymmetric stabilizing mutations in the first CH2-CH3 region and in the second CH2-CH3 region.

In some embodiments, the asymmetric stabilizing mutations in the first CH2-CH3 region and in the second CH2-CH3 region or in the second CH2-CH3 region and in the first CH2-CH3 region are F405L and K409R, respectively;
wild-type and F405L/R409K, respectively;
T366W and T366S/L368A/Y407V, respectively;
T366Y/F405A and T394W/Y407T, respectively;
T366W/F405W and T394S/Y407A, respectively;
F405W/Y407A and T366W/T394S, respectively;
L351Y/F405A/Y407V and T394W, respectively;
T366I/K392M/T394W and F405A/Y407V, respectively;
T366L/K392M/T394W and F405A/Y407V, respectively;
L351Y/Y407A and T366A/K409F, respectively;
L351Y/Y407A and T366V/K409F, respectively;
Y407A and T366A/K409F, respectively;
D399K/E356K and K409D/K392D, respectively; or
D399K/E356K/E357K and K409D/K392D/K370, respectively.

In some embodiments, the asymmetric stabilizing mutations in the first CH2-CH3 region and in the second CH2-CH3 region or in the second CH2-CH3 region and in the first CH2-CH3 region are F405L and K409R, respectively.

In some embodiments, the asymmetric stabilizing mutations in the first CH2-CH3 region and in the second CH2-CH3 region or in the second CH2-CH3 region and in the first CH2-CH3 region are wild-type and F405L/R409K, respectively.

In some embodiments, the asymmetric stabilizing mutations in the first CH2-CH3 region and in the second CH2-CH3 region or in the second CH2-CH3 region and in the first CH2-CH3 region are T366W and T366S/L368A/Y407V, respectively.

In some embodiments, the asymmetric stabilizing mutations in the first CH2-CH3 region and in the second CH2-CH3 region or in the second CH2-CH3 region and in the first CH2-CH3 region are T366Y/F405A and T394W/Y407T, respectively.

In some embodiments, the asymmetric stabilizing mutations in the first CH2-CH3 region and in the second CH2-CH3 region or in the second CH2-CH3 region and in the first CH2-CH3 region are T366W/F405W and T394S/Y407A, respectively.

In some embodiments, the asymmetric stabilizing mutations in the first CH2-CH3 region and in the second CH2-CH3 region or in the second CH2-CH3 region and in the first CH2-CH3 region are F405W/Y407A and T366W/T394S, respectively.

In some embodiments, the asymmetric stabilizing mutations in the first CH2-CH3 region and in the second CH2-CH3 region or in the second CH2-CH3 region and in the first CH2-CH3 region are L351Y/F405A/Y407V and T394W, respectively.

In some embodiments, the asymmetric stabilizing mutations in the first CH2-CH3 region and in the second CH2-CH3 region or in the second CH2-CH3 region and in the first CH2-CH3 region are T366I/K392M/T394W and F405A/Y407V, respectively.

In some embodiments, the asymmetric stabilizing mutations in the first CH2-CH3 region and in the second CH2-CH3 region or in the second CH2-CH3 region and in the first CH2-CH3 region are T366L/K392M/T394W and F405A/Y407V, respectively.

In some embodiments, the asymmetric stabilizing mutations in the first CH2-CH3 region and in the second CH2-CH3 region or in the second CH2-CH3 region and in the first CH2-CH3 region are L351Y/Y407A and T366A/K409F, respectively.

In some embodiments, the asymmetric stabilizing mutations in the first CH2-CH3 region and in the second CH2-CH3 region or in the second CH2-CH3 region and in the first CH2-CH3 region are L351Y/Y407A and T366V/K409F, respectively.

In some embodiments, the asymmetric stabilizing mutations in the first CH2-CH3 region and in the second CH2-CH3 region or in the second CH2-CH3 region and in the first CH2-CH3 region are Y407A and T366A/K409F, respectively.

In some embodiments, the asymmetric stabilizing mutations in the first CH2-CH3 region and in the second CH2-CH3 region or in the second CH2-CH3 region and in the first CH2-CH3 region are D399K/E356K and K409D/K392D, respectively.

In some embodiments, the asymmetric stabilizing mutations in the first CH2-CH3 region and in the second CH2-CH3 region or in the second CH2-CH3 region and in the first CH2-CH3 region are D399K/E356K/E357K and K409D/K392D/K370, respectively.

Asymmetric stabilizing mutations may be introduced into bispecific or multispecific antibodies to facilitate downstream processes of separating them from excess parental or intermediate molecules.

Exemplary asymmetric stabilizing mutations are those that promote Fab arm exchange (e.g., half molecule exchange, exchanging on heavy chain-light chain pair) between two parental antibodies. In this technology mutations that favor heterodimer formation of two parental antibody half-molecules either in vitro in cell-free environment or using co-expression are introduced to the heavy chain CH3 interface in each parental antibody. For example, mutations F405L in a first parental antibody and K409R in a second parental antibody may be used to promote Fab arm exchange of IgG1. For IgG4 antibodies, a wild-type first parental antibody and F405L/R409K mutation in the second parental antibody may be used.

Additional asymmetric stabilizing mutations are knob-in-hole mutations (Genentech) or mutations that introduce electrostatically-matched residues (Chugai, Amgen, NovoNordisk, Oncomed). Exemplary knob-in-hole mutations (expressed as mutated position in the first parental antibody/mutated position in the second parental antibody) are T366Y/F405A, T366W/F405W, F405W/Y407A, T394W/Y407T, T394S/Y407A, T366W/T394S, F405W/T394S and T366W/T366S_L368A_Y407V. Exemplary mutations that introduce electrostatically-matched residues are those described in US Patent Publ. No. US2010/0015133; US Patent Publ. No. US2009/0182127; US Patent Publ. No. US2010/028637 or US Patent Publ. No. US2011/0123532. Additional asymmetric stabilizing mutations are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

Mutations are typically made at the DNA level to a molecule such as the constant domain of the antibody using standard methods.

In some embodiments, the multispecific antibody comprises Q311R/F405L mutation in the first CH2-CH3 region and K409R mutation in the second CH2-CH3 region.

In some embodiments, the multispecific antibody comprises Q311K/F405L mutation in the first CH2-CH3 region and K409R mutation in the second CH2-CH3 region.

In some embodiments, the multispecific antibody comprises T307P/L309Q/F405L mutation in the first CH2-CH3 region and K409R mutation in the second CH2-CH3 region.

In some embodiments, the multispecific antibody comprises T307P/L309Q/Q311R/F405L mutation in the first CH2-CH3 region and K409R mutation in the second CH2-CH3 region.

In some embodiments, the multispecific antibody comprises Q311R/K409R mutation in the first CH2-CH3 region and F405L mutation in the second CH2-CH3 region.

In some embodiments, the multispecific antibody comprises Q311K/K409R mutation in the first CH2-CH3 region and F405L mutation in the second CH2-CH3 region.

In some embodiments, the multispecific antibody comprises T307P/L309Q/K409R mutation in the first CH2-CH3 region and F405L mutation in the second CH2-CH3 region.

In some embodiments, the multispecific antibody comprises T307P/L309Q/Q311R/K409R mutation in the first CH2-CH3 region and F405L mutation in the second CH2-CH3 region.

In some embodiments, the multispecific antibody comprises Q311R mutation in the first CH2-CH3 region and F405L/R409K mutation in the second CH2-CH3 region.

In some embodiments, the multispecific antibody comprises Q311K mutation in the first CH2-CH3 region and F405L/R409K mutation in the second CH2-CH3 region.

In some embodiments, the multispecific antibody comprises T307P/V309Q mutation in the first CH2-CH3 region and F405L/R409K mutation in the second CH2-CH3 region.

In some embodiments, the multispecific antibody comprises T307P/V309Q/Q311R mutation in the first CH2-CH3 region and F405L/R409K mutation in the second CH2-CH3 region.

In some embodiments, the multispecific antibody comprises Q311R/T366W mutation in the first CH2-CH3 region and T366S/L368A/Y407V mutation in the second CH2-CH3 region.

In some embodiments, the multispecific antibody comprises Q311K/T366W mutation in the first CH2-CH3 region and T366S/L368A/Y407V mutation in the second CH2-CH3 region.

In some embodiments, the multispecific antibody comprises T307P/L309Q/T366W mutation in the first CH2-CH3 region and T366S/L368A/Y407V mutation in the second CH2-CH3 region.

In some embodiments, the multispecific antibody comprises T307P/L309Q/Q311R/T366W mutation in the first CH2-CH3 region and T366S/L368A/Y407V mutation in the second CH2-CH3 region.

In some embodiments, the multispecific antibody comprises Q311R/T366S/L368A/Y407V mutation in the first CH2-CH3 region and T366W mutation in the second CH2-CH3 region.

In some embodiments, the multispecific antibody comprises Q311K/T366S/L368A/Y407V mutation in the first CH2-CH3 region and T366W mutation in the second CH2-CH3 region.

In some embodiments, the multispecific antibody comprises T307P/L309Q/T366S/L368A/Y407V mutation in the first CH2-CH3 region and T366W mutation in the second CH2-CH3 region.

In some embodiments, the multispecific antibody comprises T307P/L309Q/Q311R/T366S/L368A/Y407V mutation in the first CH2-CH3 region and T366W mutation in the second CH2-CH3 region.

The amino acid sequences of exemplary CH2-CH3 regions in the multispecific antibodies of the invention are shown in Table 2 and Table 3.

In some embodiments, the first CH2-CH3 region and the second CH2-CH3 region comprise an amino acid sequence of SEQ ID NOs: 2 and 22, respectively.

In some embodiments, the first CH2-CH3 region and the second CH2-CH3 region comprise an amino acid sequence of SEQ ID NOs: 3 and 22, respectively.

In some embodiments, the first CH2-CH3 region and the second CH2-CH3 region comprise an amino acid sequence of SEQ ID NOs: 4 and 22, respectively.

In some embodiments, the first CH2-CH3 region and the second CH2-CH3 region comprise an amino acid sequence of SEQ ID NOs: 5 and 22, respectively.

In some embodiments, the first CH2-CH3 region and the second CH2-CH3 region comprise an amino acid sequence of SEQ ID NOs: 6 and 23, respectively.

In some embodiments, the first CH2-CH3 region and the second CH2-CH3 region comprise an amino acid sequence of SEQ ID NOs: 7 and 23, respectively.

In some embodiments, the first CH2-CH3 region and the second CH2-CH3 region comprise an amino acid sequence of SEQ ID NOs: 8 and 23, respectively.

In some embodiments, the first CH2-CH3 region and the second CH2-CH3 region comprise an amino acid sequence of SEQ ID NOs: 9 and 23, respectively.

In some embodiments, the first CH2-CH3 region and the second CH2-CH3 region comprise an amino acid sequence of SEQ ID NOs: 10 and 24, respectively.

In some embodiments, the first CH2-CH3 region and the second CH2-CH3 region comprise an amino acid sequence of SEQ ID NOs: 11 and 24, respectively.

In some embodiments, the first CH2-CH3 region and the second CH2-CH3 region comprise an amino acid sequence of SEQ ID NOs: 12 and 24, respectively.

In some embodiments, the first CH2-CH3 region and the second CH2-CH3 region comprise an amino acid sequence of SEQ ID NOs: 13 and 24, respectively.

In some embodiments, the first CH2-CH3 region and the second CH2-CH3 region comprise an amino acid sequence of SEQ ID NOs: 14 and 25, respectively.

In some embodiments, the first CH2-CH3 region and the second CH2-CH3 region comprise an amino acid sequence of SEQ ID NOs: 15 and 25, respectively.

In some embodiments, the first CH2-CH3 region and the second CH2-CH3 region comprise an amino acid sequence of SEQ ID NOs: 16 and 25, respectively.

In some embodiments, the first CH2-CH3 region and the second CH2-CH3 region comprise an amino acid sequence of SEQ ID NOs: 17 and 25, respectively.

In some embodiments, the first CH2-CH3 region and the second CH2-CH3 region comprise an amino acid sequence of SEQ ID NOs: 18 and 26, respectively.

In some embodiments, the first CH2-CH3 region and the second CH2-CH3 region comprise an amino acid sequence of SEQ ID NOs: 19 and 26, respectively.

In some embodiments, the first CH2-CH3 region and the second CH2-CH3 region comprise an amino acid sequence of SEQ ID NOs: 20 and 26, respectively.

In some embodiments, the first CH2-CH3 region and the second CH2-CH3 region comprise an amino acid sequence of SEQ ID NOs: 21 and 26, respectively.

In some embodiments, the first CH2-CH3 region and the second CH2-CH3 region comprise an amino acid sequence of SEQ ID NOs: 52 and 54, respectively.

In some embodiments, the first CH2-CH3 region and the second CH2-CH3 region comprise an amino acid sequence of SEQ ID NOs: 52 and 55, respectively.

In some embodiments, the first CH2-CH3 region and the second CH2-CH3 region comprise an amino acid sequence of SEQ ID NOs: 53 and 54, respectively.

In some embodiments, the first CH2-CH3 region and the second CH2-CH3 region comprise an amino acid sequence of SEQ ID NOs: 53 and 55, respectively.

In some embodiments, the first CH2-CH3 region and the second CH2-CH3 region comprise an amino acid sequence of SEQ ID NOs: 56 and 54, respectively.

In some embodiments, the first CH2-CH3 region and the second CH2-CH3 region comprise an amino acid sequence of SEQ ID NOs: 56 and 55, respectively.

The multispecific antibodies of the invention may further comprise a common light chain to further facilitate downstream processes of separating them from excess parental or intermediate molecules.

In some embodiments, the multispecific antibody comprises a first light chain and a second light chain.

In some embodiments, the first light chain and the second light chain have identical amino acid sequences.

In some embodiments, the multispecific antibody is a bispecific antibody.

TABLE 2

| CH2-CH3 domain | Protein SEQ ID NO: | cDNA SEQ ID NO: |
|---|---|---|
| IgG1 CH2-CH3 Q311K | 2 | 27 |
| IgG1 CH2-CH3 Q311R | 3 | 28 |
| IgG1 CH2-CH3 T307P/L309Q | 4 | 29 |
| IgG1 CH2-CH3 T307P/L309Q/Q311R | 5 | 30 |
| IgG1 CH2-CH3 Q311K/F405L | 6 | 31 |
| IgG1 CH2-CH3 Q311R/F405L | 7 | 32 |
| IgG1 CH2-CH3 T307P/L309Q/F405L | 8 | 33 |
| IgG1 CH2-CH3 T307P/L309Q/Q311R/F405L | 9 | 34 |
| IgG1 CH2-CH3 Q311K/K409R | 10 | 35 |
| IgG1 CH2-CH3 Q311R/K409R | 11 | 36 |
| IgG1 CH2-CH3 T307P/L309Q/K409R | 12 | 37 |
| IgG1 CH2-CH3 T307P/L309Q/Q311R/K409R | 13 | 38 |
| IgG1 CH2-CH3 Q311K/T366W | 14 | 39 |
| IgG1 CH2-CH3 Q311R/T366W | 15 | 40 |
| IgG1 CH2-CH3 T307P/L309Q/T366W | 16 | 41 |
| IgG1 CH2-CH3 T307P/L309Q/Q311R/T366W | 17 | 42 |
| IgG1 CH2-CH3 Q311K/T366S/L368A/Y407V | 18 | 43 |
| IgG1 CH2-CH3 Q311R/T366S/L368A/Y407V | 19 | 44 |
| IgG1 CH2-CH3 T307P/L309Q/T366S/L368A/Y407V | 20 | 45 |
| IgG1 CH2-CH3 T307P/L309Q/Q311R/T366S/L368A/Y407V | 21 | 46 |
| Wild-type IgG1 CH2-CH3 | 22 | 47 |
| IgG1 CH2-CH3 K409R | 23 | 48 |
| IgG1 CH2-CH3 F405L | 24 | 49 |
| IgG1 CH2-CH3 T366S/L368A/Y407V | 25 | 50 |
| IgG1 CH2-CH3 T366W | 26 | 51 |
| IgG2 CH2-CH3 Q311R | 52 | 87 |
| IgG2 CH2-CH3 T307P/V309Q/Q311R | 53 | 88 |
| Wild-type IgG2 CH2-CH3 | 54 | 89 |
| IgG2 CH2-CH3 F405L/K409R | 55 | 90 |
| IgG4 CH2-CH3 T307P/V309Q | 56 | 91 |

TABLE 3

| CH2-CH3 domain | Protein SEQ ID NO: | Protein amino acid sequence |
|---|---|---|
| IgG1 CH2-CH3 Q311K | 2 | PELLGGPSVFLFPPKPKDTLMISRTPEVTCVVV DVSHEDPEVKFNWYVDGVEVHNAKTKPREEQ YNSTYRVVSVLTVLHKDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSKLTVDKSRWQQGN VFSCSVMHEALHNHYTQKSLSLSPGK |
| IgG1 CH2-CH3 Q311R | 3 | PELLGGPSVFLFPPKPKDTLMISRTPEVTCVVV DVSHEDPEVKFNWYVDGVEVHNAKTKPREEQ YNSTYRVVSVLTVLHRDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSKLTVDKSRWQQGN VFSCSVMHEALHNHYTQKSLSLSPGK |
| IgG1 CH2-CH3 T307P/L309Q | 4 | PELLGGPSVFLFPPKPKDTLMISRTPEVTCVVV DVSHEDPEVKFNWYVDGVEVHNAKTKPREEQ YNSTYRVVSVLPVQHQDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSKLTVDKSRWQQGN VFSCSVMHEALHNHYTQKSLSLSPGK |
| IgG1 CH2-CH3 T307P/L309Q/Q311R | 5 | PELLGGPSVFLFPPKPKDTLMISRTPEVTCVVV DVSHEDPEVKFNWYVDGVEVHNAKTKPREEQ YNSTYRVVSVLPVQHRDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSKLTVDKSRWQQGN VFSCSVMHEALHNHYTQKSLSLSPGK |
| IgG1 CH2-CH3 Q311K/F405L | 6 | PELLGGPSVFLFPPKPKDTLMISRTPEVTCVVV DVSHEDPEVKFNWYVDGVEVHNAKTKPREEQ YNSTYRVVSVLTVLHKDWLNGKEYKCKVSN |

TABLE 3-continued

| CH2-CH3 domain | Protein SEQ ID NO: | Protein amino acid sequence |
|---|---|---|
| | | KALPAPIEKTISKAKGQPREPQVYTLPPSRDEL<br>TKNQVSLTCLVKGFYPSDIAVEWESNGQPENN<br>YKTTPPVLDSDGSFLLYSKLTVDKSRWQQGN<br>VFSCSVMHEALHNHYTQKSLSLSPGK |
| IgG1 CH2-CH3<br>Q311R/F405L | 7 | PELLGGPSVFLFPPKPKDTLMISRTPEVTCVVV<br>DVSHEDPEVKFNWYVDGVEVHNAKTKPREEQ<br>YNSTYRVVSVLTVLHRDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFLLYSKLTVDKSRWQQGN<br>VFSCSVMHEALHNHYTQKSLSLSPGK |
| IgG1 CH2-CH3<br>T307P/L309Q/F405L | 8 | PELLGGPSVFLFPPKPKDTLMISRTPEVTCVVV<br>DVSHEDPEVKFNWYVDGVEVHNAKTKPREEQ<br>YNSTYRVVSVLPVQHQDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFLLYSKLTVDKSRWQQGN<br>VFSCSVMHEALHNHYTQKSLSLSPGK |
| IgG1 CH2-CH3<br>T307P/L309Q/Q311R/<br>F405L | 9 | PELLGGPSVFLFPPKPKDTLMISRTPEVTCVVV<br>DVSHEDPEVKFNWYVDGVEVHNAKTKPREEQ<br>YNSTYRVVSVLPVQHRDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFLLYSKLTVDKSRWQQGN<br>VFSCSVMHEALHNHYTQKSLSLSPGK |
| IgG1 CH2-CH3<br>Q311K/K409R | 10 | PELLGGPSVFLFPPKPKDTLMISRTPEVTCVVV<br>DVSHEDPEVKFNWYVDGVEVHNAKTKPREEQ<br>YNSTYRVVSVLTVLHKDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFFLYSRLTVDKSRWQQGNV<br>FSCSVMHEALHNHYTQKSLSLSPGK |
| IgG1 CH2-CH3<br>Q311R/K409R | 11 | PELLGGPSVFLFPPKPKDTLMISRTPEVTCVVV<br>DVSHEDPEVKFNWYVDGVEVHNAKTKPREEQ<br>YNSTYRVVSVLTVLHRDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFFLYSRLTVDKSRWQQGNV<br>FSCSVMHEALHNHYTQKSLSLSPGK |
| IgG1 CH2-CH3<br>T307P/L309Q/K409R | 12 | PELLGGPSVFLFPPKPKDTLMISRTPEVTCVVV<br>DVSHEDPEVKFNWYVDGVEVHNAKTKPREEQ<br>YNSTYRVVSVLPVQHQDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFFLYSRLTVDKSRWQQGNV<br>FSCSVMHEALHNHYTQKSLSLSPGK |
| IgG1 CH2-CH3<br>T307P/L309Q/Q311R/<br>K409R | 13 | PELLGGPSVFLFPPKPKDTLMISRTPEVTCVVV<br>DVSHEDPEVKFNWYVDGVEVHNAKTKPREEQ<br>YNSTYRVVSVLPVQHRDWLNGKEYKCKVSN<br>KALPAPIEKTISKAKGQPREPQVYTLPPSRDEL<br>TKNQVSLTCLVKGFYPSDIAVEWESNGQPENN<br>YKTTPPVLDSDGSFFLYSRLTVDKSRWQQGNV<br>FSCSVMHEALHNHYTQKSLSLSPGK |
| IgG1 CH2-CH3<br>Q311K/ T366W | 14 | PELLGGPSVFLFPPKPKDTLMISRTPEVTCVVV<br>DVSHEDPEVKFNWYVDGVEVHNAKTKPREEQ<br>YNSTYRVVSVLTVLHKDWLNGKEYKCKVSN<br>KALPAPIEKTISKAKGQPREPQVYTLPPSREEM<br>TKNQVSLWCLVKGFYPSDIAVEWESNGQPEN<br>NYKTTPPVLDSDGSFFLYSKLTVDKSRWQQG<br>NVFSCSVMHEALHNHYTQKSLSLSPGK |
| IgG1 CH2-CH3<br>Q311R/T366W | 15 | PELLGGPSVFLFPPKPKDTLMISRTPEVTCVVV<br>DVSHEDPEVKFNWYVDGVEVHNAKTKPREEQ<br>YNSTYRVVSVLTVLHRDWLNGKEYKCKVSN<br>KALPAPIEKTISKAKGQPREPQVYTLPPSREEM<br>TKNQVSLWCLVKGFYPSDIAVEWESNGQPEN<br>NYKTTPPVLDSDGSFFLYSKLTVDKSRWQQG<br>NVFSCSVMHEALHNHYTQKSLSLSPGK |

TABLE 3-continued

| CH2-CH3 domain | Protein SEQ ID NO: | Protein amino acid sequence |
|---|---|---|
| IgG1 CH2-CH3 T307P/L309Q/ T366W | 16 | PELLGGPSVFLFPPKPKDTLMISRTPEVTCVVV DVSHEDPEVKFNWYVDGVEVHNAKTKPREEQ YNSTYRVVSVLPVQHQDWLNGKEYKCKVSN KALPAPIEKTISKAKGQPREPQVYTLPPSREEM TKNQVSLWCLVKGFYPSDIAVEWESNGQPEN NYKTTPPVLDSDGSFFLYSKLTVDKSRWQQG NVFSCSVMHEALHNHYTQKSLSLSPGK |
| IgG1 CH2-CH3 T307P/L309Q/Q311R/ T366W | 17 | PELLGGPSVFLFPPKPKDTLMISRTPEVTCVVV DVSHEDPEVKFNWYVDGVEVHNAKTKPREEQ YNSTYRVVSVLPVQHRDWLNGKEYKCKVSN KALPAPIEKTISKAKGQPREPQVYTLPPSREEM TKNQVSLWCLVKGFYPSDIAVEWESNGQPEN NYKTTPPVLDSDGSFFLYSKLTVDKSRWQQG NVFSCSVMHEALHNHYTQKSLSLSPGK |
| IgG1 CH2-CH3 Q311K/T366S/L368A/ Y407V | 18 | PELLGGPSVFLFPPKPKDTLMISRTPEVTCVVV DVSHEDPEVKFNWYVDGVEVHNAKTKPREEQ YNSTYRVVSVLTVLHKDWLNGKEYKCKVSN KALPAPIEKTISKAKGQPREPQVYTLPPSREEM TKNQVSLSCAVKGFYPSDIAVEWESNGQPENN YKTTPPVLDSDGSFFLVSKLTVDKSRWQQGN VFSCSVMHEALHNHYTQKSLSLSPGK |
| IgG1 CH2-CH3 Q311R/T366S/L368 A/Y407V | 19 | PELLGGPSVFLFPPKPKDTLMISRTPEVTCVVV DVSHEDPEVKFNWYVDGVEVHNAKTKPREEQ YNSTYRVVSVLTVLHRDWLNGKEYKCKVSN KALPAPIEKTISKAKGQPREPQVYTLPPSREEM TKNQVSLSCAVKGFYPSDIAVEWESNGQPENN YKTTPPVLDSDGSFFLVSKLTVDKSRWQQGN VFSCSVMHEALHNHYTQKSLSLSPGK |
| IgG1 CH2-CH3 T307P/L309Q/ T366S/L368A/Y407V | 20 | PELLGGPSVFLFPPKPKDTLMISRTPEVTCVVV DVSHEDPEVKFNWYVDGVEVHNAKTKPREEQ YNSTYRVVSVLPVQHQDWLNGKEYKCKVSN KALPAPIEKTISKAKGQPREPQVYTLPPSREEM TKNQVSLSCAVKGFYPSDIAVEWESNGQPENN YKTTPPVLDSDGSFFLVSKLTVDKSRWQQGN VFSCSVMHEALHNHYTQKSLSLSPGK |
| IgG1 CH2-CH3 IgG1 T307P/L309Q/Q311R/ T366S/L368A/Y407V | 21 | PELLGGPSVFLFPPKPKDTLMISRTPEVTCVVV DVSHEDPEVKFNWYVDGVEVHNAKTKPREEQ YNSTYRVVSVLPVQHRDWLNGKEYKCKVSN KALPAPIEKTISKAKGQPREPQVYTLPPSREEM TKNQVSLSCAVKGFYPSDIAVEWESNGQPENN YKTTPPVLDSDGSFFLVSKLTVDKSRWQQGN VFSCSVMHEALHNHYTQKSLSLSPGK |
| IgG1 CH2-CH3 wild-type | 22 | PELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSKLTVDKSRWQQGN VFSCSVMHEALHNHYTQKSLSLSPGK |
| IgG1 CH2-CH3 K409R | 23 | PELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSN KALPAPIEKTISKAKGQPREPQVYTLPPSREEM TKNQVSLTCLVKGFYPSDIAVEWESNGQPENN YKTTPPVLDSDGSFFLYSRLTVDKSRWQQGNV FSCSVMHEALHNHYTQKSLSLSPGK |
| IgG1 CH2-CH3 F405L | 24 | PELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSN KALPAPIEKTISKAKGQPREPQVYTLPPSREEM TKNQVSLTCLVKGFYPSDIAVEWESNGQPENN YKTTPPVLDSDGSFLLYSKLTVDKSRWQQGN VFSCSVMHEALHNHYTQKSLSLSPGK |
| IgG1 CH2-CH3 T366S/L368A/Y407V | 25 | PELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSN |

TABLE 3-continued

| CH2-CH3 domain | Protein SEQ ID NO: | Protein amino acid sequence |
|---|---|---|
| | | KALPAPIEKTISKAKGQPREPQVYTLPPSREEM TKNQVSLSCAVKGFYPSDIAVEWESNGQPENN YKTTPPVLDSDGSFFLVSKLTVDKSRWQQGN VFSCSVMHEALHNHYTQKSLSLSPGK |
| IgG1 CH2-CH3 T366W | 26 | PELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSN KALPAPIEKTISKAKGQPREPQVYTLPPSREEM TKNQVSLWCLVKGFYPSDIAVEWESNGQPEN NYKTTPPVLDSDGSFFLYSKLTVDKSRWQQG NVFSCSVMHEALHNHYTQKSLSLSPGK |
| IgG2 CH2-CH3 Q311R | 52 | PPVAGPSVFLFPPKPKDTLMISRTPEVTCVVVD VSHEDPEVQFNWYVDGVEVHNAKTKPREEQF NSTFRVVSVLTVVHRDWLNGKEYKCKVSNKG LPAPIEKTISKTKGQPREPQVYTLPPSREEMTK NQVSLTCLVKGFYPSDISVEWESNGQPENNYK TTPPMLDSDGSFFLYSKLTVDKSRWQQGNVFS CSVMHEALHNHYTQKSLSLSPGK |
| IgG2 CH2-CH3 T307P/V309Q/Q311R | 53 | PPVAGPSVFLFPPKPKDTLMISRTPEVTCVVVD VSHEDPEVQFNWYVDGVEVHNAKTKPREEQF NSTFRVVSVLPVQHRDWLNGKEYKCKVSNKG LPAPIEKTISKTKGQPREPQVYTLPPSREEMTK NQVSLTCLVKGFYPSDISVEWESNGQPENNYK TTPPMLDSDGSFFLYSKLTVDKSRWQQGNVFS CSVMHEALHNHYTQKSLSLSPGK |
| Wild-type IgG2 CH2-CH3 | 54 | PPVAGPSVFLFPPKPKDTLMISRTPEVTCVVVD VSHEDPEVQFNWYVDGVEVHNAKTKPREEQF NSTFRVVSVLTVVHQDWLNGKEYKCKVSNK GLPAPIEKTISKTKGQPREPQVYTLPPSREEMT KNQVSLTCLVKGFYPSDISVEWESNGQPENNY KTTPPMLDSDGSFFLYSKLTVDKSRWQQGNV FSCSVMHEALHNHYTQKSLSLSPGK |
| IgG2 CH2-CH3 F405L/K409R | 55 | PPVAGPSVFLFPPKPKDTLMISRTPEVTCVVVD VSHEDPEVQFNWYVDGVEVHNAKTKPREEQF NSTFRVVSVLTVVHQDWLNGKEYKCKVSNK GLPAPIEKTISKTKGQPREPQVYTLPPSREEMT KNQVSLTCLVKGFYPSDISVEWESNGQPENNY KTTPPMLDSDGSFLLYSRLTVDKSRWQQGNV FSCSVMHEALHNHYTQKSLSLSPGK |
| IgG4 CH2-CH3 T307P/V309Q | 56 | PEFLGGPSVFLFPPKPKDTLMISRTPEVTCVVV DVSQEDPEVQFNWYVDGVEVHNAKTKPREEQ FNSTYRVVSVLTVLHQDWLNGKEYKCKVSNK GLPSSIEKTISKAKGQPREPQVYTLPPSQEEMT KNQVSLTCLVKGFYPSDIAVEWESNGQPENNY KTTPPVLDSDGSFFLYSRLTVDKSRWQEGNVF SCSVMHEALHNHYTQKSLSLSLGK |

The mutations may be transferred to IgG2 and IgG4 isotypes as positions 307, 309 and 311 are conserved across the isotypes except that IgG2 has valine at positon 309. Positions 366, 368 and 407 are also conserved across antibody isotypes. F405L is conserved, however IgG4 has R at position 409. In order to promote Fab arm exchange of human IgG4 antibody, one parental antibody will be engineered to have F405L/R409K mutation and the other parental antibody is wild-type.

In some embodiments, the multispecific antibody binds at least two antigens.

In some embodiments, the antigen is ABCF1, ACVR1, ACVR1B, ACVR2, ACVR2B, ACVRL1, ADORA2A, Aggrecan, AGR2, AICDA, AIF1, AIG1, AKAP1, AKAP2, albumin, AMH, AMHR2, ANGPT1, ANGPT2, ANGPTL3, ANGPTL4, ANPEP, APC, APOC1, APOE, AR, AZGP1 (zinc-a-glycoprotein), B7.1, B7.2, BAD, BAFF, BAG1, BAI1, BCL2, BCL6, BDNF, BLNK, BLR1 (MDR15), BlyS, BMP1, BMP2, BMP3B (GDF10), BMP4, BMP6, BMP8, BMPR1A, BMPR1B, BMPR2, BPAG1 (plectin), BRCA1, BTLA, C19orf10 (IL27w), C3, C4A, C5, C5R1, CANT1, CASP1, CASP4, CAV1, CCBP2 (D6/JAB61), CCL1 (1-309), CCL11 (eotaxin), CCL13 (MCP-4), CCL15 (MIP-1d), CCL16 (HCC-4), CCL17 (TARC), CCL18 (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CCL3 (MIP-1a), CCL4 (MIP-1b), CCL5 (RANTES), CCL7 (MCP-3), CCL8 (mcp-2), CCNA1, CCNA2, CCND1, CCNE1, CCNE2, CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), CD123, CD137, CD164, CD16a, CD16b, CD19, CD1C, CD20, CD200, CD-22, CD24, CD28, CD3, CD30, CD32a, CD32b, CD37, CD38, CD39, CD3E, CD3G, CD3Z, CD4, CD40, CD40L, CD44, CD45RB, CD47, CD52, CD69, CD72, CD73, CD74, CD79A, CD79B, CD8, CD80, CD81, CD83, CD86, CD89, CD96, CDH1 (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21Wap1/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST10, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COL1A1, COL4A3, COL6A1, CR2, CRP, CSF1 (M-CSF), CSF2 (GM-CSF), CSF3 (GCSF), CTLA4, CTNNB1 (b-catenin), CTSB (cathepsin B), CX3CL1 (SCYD1), CX3CR1 (V28), CXCL1 (GRO1), CXCL10 (IP-10), CXCL11 (I-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYC1, CYSLTR1, DAB2IP, DES, DKFZp451J0118, DNAM-1, DNCL1, DPP4, E2F1, ECGF1, EDG1, EFNA1, EFNA3, EFNB2, EGF, EGFR, ELAC2, ENG, ENO1, ENO2, ENO3, EPHB4, EPO, ERBB2 (Her-2), EREG, ERK8, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR, FGFR3, FIGF (VEGFD), FIL1 (EPSILON), FIL1 (ZETA), FLJ12584, F1125530, FLRT1 (fibronectin), FLT1, FOS, FOSL1 (FRA-1), FY (DARC), GABRP (GABAa), GAGEB1, GAGEC1, GALNAC4S-6ST, GATA3, GDF5, GFI1, GGT1, GITR, GITRL, GM-CSF, GNAS1, GNRH1, GPR2 (CCR10), GPR31, GPR44, GPR81 (FKSG80), GRCC10 (C10), GRP, GSN (Gelsolin), GSTP1, HAVCR2, HDAC4, HDAC5, HDAC7A, HDAC9, HGF, HIF1A, HIP1, histamine and histamine receptors, HLA, HLA-A, HLA-DRA, HM74, HMOX1, HUMCYT2A, HVEM, ICEBERG, ICOS, ICOSL, IDO, ID2, IFN-a, IFNA1, IFNA2, IFNA4, IFNA6, IFNA7, IFNB1, IFNgamma, IFNW1, IGBP1, IGF1, IGF1R, IGF2, IGFBP2, IGFBP3, IGFBP6, IL-1, IL10, IL10RA, IL10RB, IL11, IL11RA, IL-12, IL12A, IL12B, IL12RB1, IL12RB2, IL13, IL13RA1, IL13RA2, IL14, IL15, IL15RA, IL16, IL17, IL17B, IL17C, IL17R, IL18, IL18BP, IL18R1, IL18RAP, IL19, IL1A, IL1B, IL1F10, IL1F5, IL1F6, IL1F7, IL1F8, IL1F9, IL1HY1, IL1R1, IL1R2, IL1RAP, IL1RAPL1, IL1RAPL2, IL1RL1, IL1RL2, IL1RN, IL2, IL20, IL20RA, IL21R, IL22, IL22R, IL22RA2, IL23, IL24, IL25, IL26, IL27, IL28A, IL28B, IL29, IL2RA, IL2RB, IL2RG, IL3, IL30, IL3RA, IL4, IL4R, ILS, IL5RA, IL6, IL6R, IL6ST (glycoprotein 130), IL7, IL7R, IL8, IL8RA, IL8RB, IL8RB, IL9, IL9R, ILK, INHA, INHBA, INSL3, INSL4, insulin, insulin receptor, IRAK1, IRAK2, ITGA1, ITGA2, ITGA3, ITGA6 (a6 integrin), ITGAV, ITGB3, ITGB4 (b 4 integrin), JAG1, JAK1, JAK3, JUN, K6HF, KAI1, KDR, KITLG, KIR, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMAS, LDL, LEP (leptin), LFA, Lingo-p75, Lingo-Troy, LPS, LTA (TNF-b), LTB, LTB4R (GPR16), LTB4R2, LTBR, MACMARCKS, MAG or Omgp, MAP2K7 (c-Jun), MDK, mesothelin, MIB1, midkine, MIF, MIP-2, MKI67 (Ki-67), MMP2, MMP9, MS4A1, MSMB, MT3 (metallothionectin-III), MTSS1, MUC1 (mucin), MYC, MYD88, NCK2, neurocan, NFKB1, NFKB2, NGFB (NGF), NGFR, NgR-Lingo, NgR-Nogo66 (Nogo), NgR-p75, NgR-Troy, NKG2D, NKp46, NME1 (NM23A), NOX5, NPPB, NR0B1, NR0B2, NR1D1, NR1D2, NR1H2, NR1H3, NR1H4, NRII2, NRII3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZ1, OPRD1, OX-40, OX-40L, P2RX7, PAP, PART1, PATE, PAWR, PCA3, PCNA, PD-1, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PR1, PRKCQ, PRKD1, PRL, PROC, PROK2, PSAP, PSCA, PTAFR, PTEN, PTGS2 (COX-2), PTN, RAC2 (p21Rac2), RARB, RGS1, RGS13, RGS3, RNF110 (ZNF144), ROBO2, ROR1, SI00A2, SCGB1D2 (lipophilin B), SCGB2A1 (mammaglobin 2), SCGB2A2 (mammaglobin 1), SCYE1 (endothelial Monocyte-activating cytokine), SDF2, SERPINA1, SERPINA3, SERPINB5 (maspin), SERPINE1 (PAI-1), SERPINF1, SHBG, SLA2, SLC2A2, SLC33A1, SLC43A1, SLIT2, SPP1, SPRR1B (Spr1), ST6GAL1, STAB1, STAT6, STEAP, STEAP2, TB4R2, TBX21, TCP10, TDGF1, TEK, TF (transferrin receptor), TGFA, TGFB1, TGFB111, TGFB2, TGFB3, TGFBI, TGFBR1, TGFBR2, TGFBR3, TH1L, THBS1 (thrombospondin-1), THBS2, THBS4, THPO, TIE (Tie-1), TIGIT, TIM-3, TIMP3, tissue factor, TLR10, TLR2, TLR3, TLR4, TLR5, TLR6, TLR7, TLR8, TLR9, TNF, TNF-a, TNFAIP2 (B94), TNFAIP3, TNFRSF11A, TNFRSF1A, TNFRSF1B, TNFRSF21, TNFRSF5, TNFRSF6 (Fas), TNFRSF7, TNFRSF8, TNFRSF9, TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Iia), TP53, TPM1, TPM2, TRADD, TRAF1, TRAF2, TRAF3, TRAF4, TRAF5, TRAF6, TREM1, TREM2, TRPC6, TSLP, TWEAK, VEGF, VEGFB, VEGFC, versican, VHL C5, VISTA, VLA-4, XCL1 (lymphotactin), XCL2 (SCM-1b), XCR1 (GPR5/CCXCR1), YY1, and ZFPM2.

In some embodiments, the multispecific antibody binds CD3.

In some embodiments, the multispecific antibody binds CD3 and a tumor antigen.

In some embodiments, the multispecific antibody binds two antigens wherein the two antigens are any two of PD1, CD27, CD28, NKP46, ICOS, GITR, OX40, CTLA4, LAG3, TIM3, KIRa, CD73, CD39, IDO, BTLA, VISTA, TIGIT, CD96, CD30, HVEM, DNAM-1, LFA, tumor antigen, EGFR, cMet, FGFR, ROR1, CD123, IL1RAP, FGFR, mesothelin, CD3, T cell receptor, CD32b, CD32a, CD16a, CD16b, NKG2D, NKp46, CD28, CD47, DLL, CD8, CD89, HLA, B cell receptor or CD137.

Engineering Multispecific Antibodies of the Invention

Additional Fc mutations may be made to the multispecific antibodies of the invention to modulate effector functions and pharmacokinetic properties. In traditional immune function, the interaction of antibody-antigen complexes with cells of the immune system results in a wide array of responses, ranging from effector functions such as antibody-dependent cytotoxicity and phagocytosis to immunomodulatory signals such as regulating lymphocyte proliferation and antibody secretion. All of these interactions are initiated through the binding of the Fc region of antibodies or immune complexes to specialized cell surface receptors. The diversity of cellular responses triggered by antibodies and immune complexes results from the structural heterogeneity of Fc receptors: FcγRI (CD64), FcγRIIA (CD32A) and FcγRIII (CD16) are activating Fcγ receptors (i.e., immune system enhancing), and FcγRIIB (CD32B) is an inhibitory Fcγ receptor (i.e., immune system dampening). Binding to the FcRn receptor modulates antibody half-life.

In some embodiments, the multispecific antibody of the invention further comprises at least one mutation that modulates binding of the antibody to FcγR.

In some embodiments, the multispecific antibody of the invention further comprises at least one mutation that modulates binding of the antibody to or FcRn.

Exemplary mutations that increase half-life of the multispecific antibody are mutations M428L/N434S, M252Y/S254T/T256E, T250Q/M428L, N434A and T307A/E380A/N434A. Exemplary mutations that reduce half-life of the multispecific antibody are mutations H435A, P257I/N434H, D376V/N434H, M252Y/S254T/T256E/H433K/N434F, T308P/N434A and H435R.

In some embodiments, the multispecific antibody of the invention comprises at least one mutation that reduces binding of the antibody to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Exemplary mutations that reduce binding of the multispecific antibody of the invention to activating FcγR and/or minimize antibody effector functions are L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4.

Exemplary mutations that increase binding of the multispecific antibody of the invention to an activating Fcγ and/or enhance antibody effector functions are S239D/I332E, S298A/E333A/K334A, F243L/R292P/Y300L, F243L/R292P/Y300L/P396L, F243L/R292P/Y300L/V305I/P396L and G236A/S239D/I332E, K326A/E333A, K326W/E333A, H268F/S324T, S267E/H268F, S267E/S324T and S267E/H268F/S324T.

Well-known S228P may be made in IgG4 antibodies to enhance IgG4 stability.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcγRIIIa. Death of the antibody-coated target cells occurs as a result of effector cell activity through the secretion of membrane pore-forming proteins and proteases. To assess ADCC activity of the antibodies of the invention, the antibodies may be added to cells expressing the desired antigen in combination with immune effector cells, which may be activated by the antigen antibody complexes resulting in cytolysis of the target cell. Cytolysis may be detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include cells expressing the desired antigen either endogenously or recombinantly. In an exemplary assay, target cells are used with a ratio of 1 target cell to 50 effector cells. Target cells are pre-labeled with BATDA (PerkinElmer) for 20 minutes at 37° C., washed twice and resuspended in DMEM, 10% heat-inactivated FBS, 2 mM L-glutamine (all from Invitrogen). Target ($1 \times 10^4$ cells) and effector cells ($0.5 \times 10^6$ cells) are combined and 100 µl of cells are added to the wells of 96-well U-bottom plates. An additional 100 µl is added with or without the test antibodies. The plates are centrifuged at 200 g for 3 minutes, incubated at 37° C. for 2 hours, and then centrifuged again at 200 g for 3 minutes. A total of 20 µl of supernatant is removed per well and cell lysis is measured by the addition of 200 µl of the DELPHIA® Europium-based reagent (PerkinElmer). Data is normalized to maximal cytotoxicity with 0.67% Triton X-100 (Sigma Aldrich) and minimal control determined by spontaneous release of BATDA from target cells in the absence of any antibody.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma or tumor cells expressing the desired antigen as target cells engineered to express GFP or other labeled molecule. Effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the $CD11^+CD14^+$ macrophages using standard methods.

"Complement-dependent cytotoxicity" (CDC), refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC may be measured for example by plating Daudi cells at $1 \times 10^5$ cells/well (50 µl/well) in RPMI-B (RPMI supplemented with 1% BSA), adding 50 µl of test antibodies to the wells at final concentration between 0-100 µg/ml, incubating the reaction for 15 min at room temperature, adding 11 µl of pooled human serum to the wells, and incubation the reaction for 45 min at 37° C. Percentage (%) lysed cells may be detected as % propidium iodide stained cells in FACS assay using standard methods.

Additional mutations may further be made to the multispecific antibodies of the invention that enhance binding of the antibody to FcγRIIb. Exemplary such mutations are mutations S267E, S267D, S267E/I332E, S267E/L328F, G236D/S267E and E233D/G237D/H268D/P271G/A330R/P238D.

In general, mutations enhancing binding to activating FcγR and reducing binding to inhibitory FcγRIIb may be engineered into antibodies to be used to enhance immune responses in a subject, such as for the treatment of cancers and infections. Mutations reducing binding to activating FcγR or enhancing binding to the inhibitory FcγRIIb may be engineered into antibodies which are used to dampen immune responses in a subject, such as for the treatment of inflammatory or autoimmune disease. Mutations enhancing binding to inhibitory FcγRIIb may also be introduced into agonistic antibodies that bind TNFR superfamily members to enhance their agonistic activity.

The ability of the multispecific antibodies of the invention to induce ADCC may be enhanced by engineering their oligosaccharide component. Human IgG1 is N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolarity, application of a variant CHO line Lec13 as the host cell line, application of a variant CHO line EB66 as the host cell line, application of a rat hybridoma cell line YB2/0 as the host cell line, introduction of small interfering RNA specifically against the cc 1,6-fucosyltrasferase (FUT8) gene, or coexpression of β-1,4-N-acetylglucosaminyltransferase III and Golgi α-mannosidase II or a potent alpha-mannosidase I inhibitor, kifunensine.

In some embodiments, the multispecific antibodies of the invention have a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the multispecific antibodies of the invention have a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" refers to antibodies with fucose content of about 0%-15%.

"Normal fucose" or 'normal fucose content" refers to antibodies with fucose content of about over 50%, typically about over 60%, 70%, 80% or over 85%.

The multispecific antibodies of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention described herein may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function.

Multispecific antibodies of the invention may be modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn and Pluckthun 2001). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold. Formulation studies suggest that a Fab $T_m$ has implication for long-term physical stability of a corresponding mAb.

C-terminal lysine (CTL) may be removed from injected antibodies by endogenous circulating carboxypeptidases in the blood stream. During manufacturing, CTL removal may be controlled to less than the maximum level by control of concentration of extracellular $Zn^{2+}$, EDTA or EDTA—$Fe^{3+}$ as described in U.S. Patent Publ. No. US20140273092. CTL content in antibodies can be measured using known methods.

In some embodiments, the multispecific antibodies of the invention have a C-terminal lysine content of about 10% to about 90%, about 20% to about 80%, about 40% to about 70%, about 55% to about 70%, or about 60%.

In some embodiments, the multispecific antibodies of the invention have a C-terminal lysine content of about 0%, 5%, 10%, 20%, 30%, 40%, 50%, 60%, 70%, 80%, 90% or 100%.

The invention also provides for an isolated antibody comprising two heavy chains having identical amino acid sequences and two light chains, wherein the two identical heavy chains comprises a mutation Q311R, Q311K, T307P/L309Q, T307P/V309Q, T307P/L309Q/Q311R or T307P/V309Q/Q311R, wherein residue numbering is according to the EU Index.

The invention also provides for an isolated antibody comprising two heavy chains having identical amino acid sequences and two light chains, wherein the two identical heavy chains comprises a mutation Q311R, wherein residue numbering is according to the EU Index.

The invention also provides for an isolated antibody comprising two heavy chains having identical amino acid sequences and two light chains, wherein the two identical heavy chains comprises a mutation Q311K, wherein residue numbering is according to the EU Index.

The invention also provides for an isolated antibody comprising two heavy chains having identical amino acid sequences and two light chains, wherein the two identical heavy chains comprises a mutation T307P/L309Q, wherein residue numbering is according to the EU Index.

The invention also provides for an isolated antibody comprising two heavy chains having identical amino acid sequences and two light chains, wherein the two identical heavy chains comprises a mutation T307P/V309Q, wherein residue numbering is according to the EU Index.

The invention also provides for an isolated antibody comprising two heavy chains having identical amino acid sequences and two light chains, wherein the two identical heavy chains comprises a mutation T307P/L309Q/Q311R, wherein residue numbering is according to the EU Index.

The invention also provides for an isolated antibody comprising two heavy chains having identical amino acid sequences and two light chains, wherein the two identical heavy chains comprises a mutation T307P/V309Q/Q311R, wherein residue numbering is according to the EU Index.

The isolated antibody is useful as a parental antibody for generating the multispecific antibodies of the invention.

In some embodiments, the isolated antibody further comprises a mutation F405L, K409R, F405L/R409K, T366W or T366S/L368A/Y407V.

In some embodiments, the isolated antibody is an IgG1, an IgG2 or an IgG4 isotype.

Methods of Generating Engineered Multispecific Antibodies of the Invention

The engineered multispecific antibodies of the invention that have altered amino acid sequences when compared to the parental multispecific antibodies may be generated using standard cloning and expression technologies. For example, site-directed mutagenesis or PCR-mediated mutagenesis may be performed to introduce the mutation(s) and the effect on antibody binding or other property of interest, may be evaluated using well known methods and the methods described herein in the Examples.

Antibody Allotypes

Immunogenicity of therapeutic antibodies is associated with increased risk of infusion reactions and decreased duration of therapeutic response (Baert et al., (2003) *N Engl J Med* 348:602-08). The extent to which therapeutic antibodies induce an immune response in the host may be determined in part by the allotype of the antibody (Stickler et al., (2011) *Genes and Immunity* 12:213-21). Antibody allotype is related to amino acid sequence variations at specific locations in the constant region sequences of the antibody.

Table 4 shows select IgG1, IgG2 and IgG4 allotypes.

In some embodiments, the multispecific antibodies of the invention are of G2m(n), G2m(n–), G2m(n)/(n–), nG4m(a), G1m(17) or G1m(17,1) allotype.

TABLE 4

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n) | T | M | | | | | | |
| G2m(n–) | P | V | | | | | | |
| G2m(n)/(n–) | T | V | | | | | | |
| nG4m(a) | | | L | R | | | | |
| G1m(17) | | | | | K | E | M | A |
| G1m(17,1) | | | | | K | D | L | A |

Generation and Isolation of Multispecific Antibodies of the Invention

The multispecific antibodies of the invention may be generated using standard molecular biology techniques and promoting Fab arm exchange of the parental antibodies. The multispecific antibodies of the invention may be purified using protein A ligand affinity chromatography.

The invention also provides for a method of making an isolated multispecific antibody comprising a first heavy chain or fragment thereof comprising a mutation Q311R, Q311K, T307P/L309Q, T307P/V309Q, T307P/L309Q/Q311R or T307P/V309Q/Q311R and a second heavy chain or fragment thereof comprising wild-type amino acid residue at positions 307, 309 and 311, comprising providing a first parental antibody comprising the first heavy chain or fragment thereof comprising the mutation Q311R, Q311K, T307P/L309Q, T307P/V309Q, T307P/L309Q/Q311R or T307P/V309Q/Q311R and a first light chain;

providing a second parental antibody comprising the second heavy chain or fragment thereof comprising wild-type amino acid residue at positions 307, 309 and 311 and a second light chain;

contacting the first parental antibody and the second parental antibody in a sample;

incubating the sample; and purifying the multispecific antibody using protein A ligand affinity chromatography.

The invention also provides for a method of making an isolated multispecific antibody comprising a first heavy chain or fragment thereof comprising a mutation T307P/L309Q and a second heavy chain or fragment thereof comprising wild-type amino acid residue at positions 307 and 309, comprising providing a first parental antibody comprising the first heavy chain or fragment thereof comprising the mutation T307P/L309Q and a first light chain;

providing a second parental antibody comprising the second heavy chain or fragment thereof comprising wild-type amino acid residue at positions 307 and 309 and a second light chain;

contacting the first parental antibody and the second parental antibody in a sample;

incubating the sample; and purifying the multispecific antibody using protein A ligand affinity chromatography.

The invention also provides for a method of making an isolated multispecific antibody comprising a first heavy chain or fragment thereof comprising a mutation T307P/

V309Q and a second heavy chain or fragment thereof comprising wild-type amino acid residue at positions 307 and 309, comprising providing a first parental antibody comprising the first heavy chain or fragment thereof comprising the mutation T307P/V309Q and a first light chain;

providing a second parental antibody comprising the second heavy chain or fragment thereof comprising wild-type amino acid residue at positions 307 and 309 and a second light chain;

contacting the first parental antibody and the second parental antibody in a sample;

incubating the sample; and purifying the multispecific antibody using protein A ligand affinity chromatography.

The invention also provides for a method of making an isolated multispecific antibody comprising a first heavy chain or fragment thereof comprising a mutation T307P/L309Q/Q311R and a second heavy chain or fragment thereof comprising wild-type amino acid residue at positions 307, 309 and 311, comprising providing a first parental antibody comprising the first heavy chain or fragment thereof comprising the mutation T307P/L309Q/Q311R and a first light chain;

providing a second parental antibody comprising the second heavy chain or fragment thereof comprising wild-type amino acid residue at positions 307, 309 and 311 and a second light chain;

contacting the first parental antibody and the second parental antibody in a sample;

incubating the sample; and purifying the multispecific antibody using protein A ligand affinity chromatography.

The invention also provides for a method of making an isolated multispecific antibody comprising a first heavy chain or fragment thereof comprising a mutation T307P/V309Q/Q311R and a second heavy chain or fragment thereof comprising wild-type amino acid residue at positions 307, 309 and 311, comprising providing a first parental antibody comprising the first heavy chain or fragment thereof comprising the mutation T307P/V309Q/Q311R and a first light chain;

providing a second parental antibody comprising the second heavy chain or fragment thereof comprising wild-type amino acid residue at positions 307, 309 and 311 and a second light chain;

contacting the first parental antibody and the second parental antibody in a sample;

incubating the sample; and purifying the multispecific antibody using protein A ligand affinity chromatography.

The VH and the VL regions of the multispecific antibodies may be derived from existing VH/VL regions of antibodies specific to a desired antigen, or from VH/VL domains of parental antibodies generated de novo.

The parental antibodies may be generated de novo using various technologies. For example, the hybridoma method of Kohler and Milstein, Nature 256:495, 1975 may be used to generate them. In the hybridoma method, a mouse or other host animal, such as a hamster, rat or monkey, is immunized with an antigen followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Transgenic mice carrying human immunoglobulin (Ig) loci in their genome may be used to generate the parental antibodies against a desired antigen, and are described in for example Int. Pat. Publ. No. WO90/04036, U.S. Pat. No. 6,150,584, Int. Pat. Publ. No. WO99/45962, Int. Pat. Publ. No. WO02/066630, Int. Pat. Publ. No. WO02/43478, Lonberg et al., Nature 368:856-9, 1994; Green et al., Nature Genet 7:13-21, 1994; Green & Jakobovits, Exp. Med. 188: 483-95, 1998; Lonberg and Huszar, Int Rev Immunol 13:65-93, 1995; Bruggemann et al., Eur J Immunol 21:1323-1326, 1991; Fishwild et al., Nat Biotechnol 14:845-851, 1996; Mendez et al., Nat Genet 15:146-156, 1997; Green, J Immunol Methods 231:11-23, 1999; Yang et al., Cancer Res 59:1236-1243, 1999; Brüggemann and Taussig, Curr Opin Biotechnol. 8:455-458, 1997; Int. Pat. Publ. No. WO02/043478). The endogenous immunoglobulin loci in such mice may be disrupted or deleted, and at least one complete or partial human immunoglobulin locus may be inserted into the mouse genome using homologous or non-homologous recombination, using transchromosomes, or using minigenes. Companies such as Regeneron (http://www regeneron com), Harbour Antibodies (http://www harbourantibodies com), Open Monoclonal Technology, Inc. (OMT) (http://www omtinc net), KyMab (http://www kymab com), Trianni (http://www trianni com) and Ablexis (http://www ablexis com) may be engaged to provide human antibodies directed against a selected antigen using technology as described above.

The parental antibodies may also be selected from a phage display library, where the phage is engineered to express human immunoglobulins or portions thereof such as Fabs, single chain antibodies (scFv), or unpaired or paired antibody variable regions. The parental antibodies may be isolated for example from phage display library expressing antibody heavy and light chain variable regions as fusion proteins with bacteriophage pIX coat protein as described in Shi et al., J Mol Biol 397:385-96, 2010 and Int. Pat. Publ. No. WO09/085462). The libraries may be screened for phage binding to the desired antigen and the obtained positive clones may be further characterized, the Fabs isolated from the clone lysates, and expressed as full length IgGs. Such phage display methods for isolating human antibodies are described in for example: U.S. Pat. Nos. 5,223,409; 5,403,484, 5,571,698, 5,427,908, 5,580,717, 5,969,108, 6,172,197, 5,885,793; 6,521,404; 6,544,731; 6,555,313; 6,582,915 and 6,593,081.

The isolated VH/VL regions may be cloned as any Ig isotype or a portion of antibody constant domain, such as a CH2-CH3 region using standard cloning methods. Fc mutations may be introduced to the parental antibodies using standard methods.

In some embodiments, the first parental antibody and the second parental antibody are provided as purified antibodies.

In some embodiments, the first parental antibody and the second parental antibody are provided in a cell culture medium collected from cells expressing the first parental antibody and the second parental antibody.

In some embodiments, the first parental antibody and the second parental antibody are co-expressed in a cell.

It has been demonstrated herein that generation of multispecific antibodies of the invention occurs when parental antibodies are provided in crude extracts as unpurified antibodies. Ability to purify the multispecific antibodies from crude extracts reduces cost of downstream processing as only one purification step is needed.

Once the parental antibodies are contacted together, an incubation step is performed.

In some embodiments, incubation is performed at a temperature of about 20° C. to about 37° C.

In some embodiments, incubation is performed at a temperature of about 25° C. to about 37° C.

In some embodiments, incubation is performed at a temperature of about 25° C. to about 37° C. about ninety minutes to about six hours.

In some embodiments, a reducing agent is added during the incubation step.

In some embodiments, the reducing agent is 2-mercaptoethylamine (2-MEA).

In some embodiments, the reducing agent is dithiothreitol (DTT).

In some embodiments, the reducing agent is dithioerythritol (DTE).

In some embodiments, the reducing agent is glutathione.

In some embodiments, the reducing agent is tris(2-carboxyethyl)phosphine (TCEP).

In some embodiments, the reducing agent is L-cysteine.

In some embodiments, the reducing agent is beta-mercaptoethanol.

In some embodiments, the reducing agent is present at a concentration of about 10 mM to about 100 mM.

In some embodiments, 2-MEA is present at a concentration of about 10 mM to about 100 mM.

In some embodiments, 2-MEA is present at a concentration of about 25 mM to about 75 mM.

For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

In some embodiments, protein A ligand chromatography employs a pH gradient.

In some embodiments, the pH gradient is from about pH 7.0 to about pH 3.0.

In some embodiments, the pH gradient is from about pH 4.6 to about pH 3.4.

In some embodiments, the multimeric antibody elutes between about pH 4.4 to about pH 4.1.

In some embodiments, the pH gradient is a step gradient of pH 4.6, pH 4.1 and pH 3.4.

In some embodiments, protein A ligand chromatography employs a citrate buffer.

In some embodiments, protein A ligand chromatography employs a 50 mM citrate buffer.

In some embodiments, protein A ligand chromatography employs an acetate buffer.

In some embodiments, protein A ligand chromatography employs a 40 mM acetate buffer.

Protein A chromatography may be carried out using mAbSelect Sure columns (GE Healthcare) or in batch mode. Culture supernatants are loaded onto the column directly without additional processing, according to the manufacturer's column specifications. Antibodies are eluted using pH step gradient using buffers containing 50 mM citrate pH 4.7, pH 4.2 or pH 3.4. Elution fractions are collected and concentrated to >1 mg/mL prior to analysis. Purity of the isolated multimeric antibody can be assessed using hydrophobic interaction chromatography (HIC).

Compositions of Matter: Multimeric Proteins of the Invention

The mutations identified herein may be used to isolate any multimeric protein from its parental proteins as long as the multimeric protein has at least two polypeptide chains each having a CH2-CH3 region with asymmetrical Q311R, Q311K, T307P/L309Q, T307P/V309Q, T307P/L309Q/Q311R or T307P/V309Q/Q311R mutations.

The invention also provides for a multimeric protein comprising a first polypeptide and a second polypeptide, wherein the first polypeptide comprises a first CH2-CH3 region comprising a mutation Q311R, Q311K, T307P/L309Q, T307P/V309Q, T307P/L309Q/Q311R or T307P/V309Q/Q311R and the second polypeptide comprises a second CH2-CH3 region comprising a wild-type amino acid residue at positions 307, 309 and 311, wherein residue numbering is according to the EU Index.

The invention also provides for a multimeric protein comprising a first polypeptide and a second polypeptide, wherein the first polypeptide comprises a first CH2-CH3 region comprising a mutation Q311R and the second polypeptide comprises a second CH2-CH3 region comprising a wild-type amino acid residue at position 311, wherein residue numbering is according to the EU Index.

The invention also provides for a multimeric protein comprising a first polypeptide and a second polypeptide, wherein the first polypeptide comprises a first CH2-CH3 region comprising a mutation Q311K and the second polypeptide comprises a second CH2-CH3 region comprising a wild-type amino acid residue at position 311, wherein residue numbering is according to the EU Index.

The invention also provides for a multimeric protein comprising a first polypeptide and a second polypeptide, wherein the first polypeptide comprises a first CH2-CH3 region comprising a mutation T307P/L309Q and the second polypeptide comprises a second CH2-CH3 region comprising a wild-type amino acid residue at positions 307 and 309, wherein residue numbering is according to the EU Index.

The invention also provides for a multimeric protein comprising a first polypeptide and a second polypeptide, wherein the first polypeptide comprises a first CH2-CH3 region comprising a mutation T307P/V309Q and the second polypeptide comprises a second CH2-CH3 region comprising a wild-type amino acid residue at positions 307 and 309, wherein residue numbering is according to the EU Index.

The invention also provides for a multimeric protein comprising a first polypeptide and a second polypeptide, wherein the first polypeptide comprises a first CH2-CH3 region comprising a mutation T307P/L309Q/Q311R and the second polypeptide comprises a second CH2-CH3 region comprising a wild-type amino acid residue at positions 307, 309 and 311, wherein residue numbering is according to the EU Index.

The invention also provides for a multimeric protein comprising a first polypeptide and a second polypeptide, wherein the first polypeptide comprises a first CH2-CH3 region comprising a mutation T307P/V309Q/Q311R and the second polypeptide comprises a second CH2-CH3 region comprising a wild-type amino acid residue at positions 307, 309 and 311, wherein residue numbering is according to the EU Index.

In some embodiments, the first CH2-CH3 region and the second CH2-CH3 region are an IgG1 isotype.

In some embodiments, the first CH2-CH3 region and the second CH2-CH3 region are an IgG2 isotype.

In some embodiments, the first CH2-CH3 region and the second CH2-CH3 region are an IgG4 isotype.

In some embodiments, the first CH2-CH3 region has reduced binding to protein A ligand when compared to the second CH2-CH3 region.

In some embodiments, protein A ligand comprises Staphylococcal Protein A.

In some embodiments, protein A ligand comprises Z-domain.

In some embodiments, protein A ligand comprises Y-domain.

In some embodiments, Z-domain comprises an amino acid sequence of SEQ ID NO: 1.

In some embodiments, protein A ligand comprises an amino acid sequence of SEQ ID Nos: 99, 100 or 101.

In some embodiments, the multimeric protein further comprises asymmetric stabilizing mutations in the first CH2-CH3 region and in the second CH2-CH3 region.

In some embodiments, the asymmetric stabilizing mutations in the first CH2-CH3 region and in the second CH2-CH3 region or in the second CH2-CH3 region and in the first CH2-CH3 region are F405L and K409R, respectively;
wild-type and F405L/R409K, respectively;
T366W and T366S/L368A/Y407V, respectively;
T366Y/F405A and T394W/Y407T, respectively;
T366W/F405W and T394S/Y407A, respectively;
F405W/Y407A and T366W/T394S, respectively;
L351Y/F405A/Y407V and T394W, respectively;
T366I/K392M/T394W and F405A/Y407V, respectively;
T366L/K392M/T394W and F405A/Y407V, respectively;
L351Y/Y407A and T366A/K409F, respectively;
L351Y/Y407A and T366V/K409F, respectively;
Y407A and T366A/K409F, respectively;
D399K/E356K and K409D/K392D, respectively; or
D399K/E356K/E357K and K409D/K392D/K370, respectively.

In some embodiments, the first CH2-CH3 region and the second CH2-CH3 region comprise an amino acid sequence of SEQ ID NOs: 2, and 22, respectively;
SEQ ID NOs: 3 and 22, respectively;
SEQ ID NOs: 4 and 22, respectively;
SEQ ID NOs: 5 and 22, respectively;
SEQ ID NOs: 6 and 23, respectively;
SEQ ID NOs: 7 and 23, respectively;
SEQ ID NOs: 8 and 23, respectively;
SEQ ID NOs: 9 and 23, respectively;
SEQ ID NOs: 10 and 24, respectively;
SEQ ID NOs: 11 and 24, respectively;
SEQ ID NOs: 12 and 24, respectively;
SEQ ID NOs: 13 and 24, respectively;
SEQ ID NOs: 14 and 25, respectively;
SEQ ID NOs: 15 and 25, respectively;
SEQ ID NOs: 16 and 25, respectively;
SEQ ID NOs: 17 and 25, respectively;
SEQ ID NOs: 18 and 26, respectively;
SEQ ID NOs: 19 and 26, respectively;
SEQ ID NOs: 20 and 26, respectively;
SEQ ID NOs: 21 and 26, respectively;
SEQ ID NOs: 52 and 54, respectively;
SEQ ID NOs: 52 and 55, respectively;
SEQ ID NOs: 53 and 54, respectively;
SEQ ID NOs: 53 and 55, respectively;
SEQ ID NOs: 56 and 54, respectively; or
SEQ ID NOs: 56 and 55, respectively.

In some embodiments, the first CH2-CH3 region and/or the second CH2-CH3 region is coupled to a heterologous protein.

In some embodiments, the heterologous protein is a peptide.

In some embodiments, the heterologous protein is an extracellular domain of a receptor.

In some embodiments, the heterologous protein is an extracellular domain of a ligand.

In some embodiments, the heterologous protein is a secreted protein.

In some embodiments, the heterologous protein is a scFv.

In some embodiments, the heterologous protein is a heavy chain variable region (VH).

In some embodiments, the heterologous protein is a light chain variable region (VL).

In some embodiments, the heterologous protein is a fibronectin type III domain.

In some embodiments, the heterologous protein is a fynomer.

In some embodiments, the heterologous protein is coupled to the N-terminus of the first CH2-CH3 region and/or the second CH2-CH3 region, optionally via a linker.

In some embodiments, the heterologous protein is coupled to the C-terminus of the first CH2-CH3 region and/or the second CH2-CH3 region, optionally via a linker.

In some embodiments, the linker comprises an amino acid sequence of SEQ ID NOs: 57, 58, 59, 60, 61, 62, 63, 64, 65, 66, 67, 92, 93, 94, 95, 96, 97 or 98.

In some embodiments, the multimeric protein is an antibody.

In some embodiments, the antibody is multispecific.

In some embodiments, the antibody is bispecific.

In some embodiments, the antibody is monospecific.

In some embodiments, the multimeric protein contains two polypeptide chains.

In some embodiments, the multimeric protein contains three polypeptide chains.

In some embodiments, the multimeric protein contains four polypeptide chains.

Exemplary multimeric protein formats that are encompassed by the invention are shown in Table 5. In the formats, peptide (P) may be an extracellular domain of a receptor, an extracellular domain of a ligand, a secreted protein, a scFv, a Fab, a heavy chain variable region (VH), a light chain variable region (VL), a fibronectin type III domain or a fynomer. In the formats, linker (L) may optionally be absent. Exemplary linkers are shown in Table 6. Asterix (*) in the table indicates that the two CH2-CH3 domains harbor asymmetrical mutations as have been described herein.

The multimeric proteins of the invention may be further modified as described herein for multispecific antibodies using standard methods. The multimeric proteins of the invention may be made using standard cloning methods.

TABLE 5

| Format | Polypeptide chains |
|---|---|
| Format 1 | (P-L)$_n$-CH2-CH3 |
|  | (P-L)$_n$-CH2-CH3* |
| Format 2 | CH2-CH3-(L-P)$_n$ |
|  | CH2-CH3*-(L-P)$_n$ |
| Format 3 | (P-L)$_n$-CH2-CH3-(L-P)$_n$ |
|  | (P-L)$_n$-CH2-CH3*-(L-P)$_n$ |
| Format 4 | VH1-CH1-hinge-CH2-CH3 |
|  | VH2-CH1-hinge-CH2-CH3* |
|  | VL1 |
|  | VL2 |
| Format 5 | VH1-L-VH2-L-CH2-CH3 |
|  | VH1-L-VH2-L-CH2-CH3* |
|  | VL1 |
|  | VL2 |
| Format 6 | VH1-CH1-hinge-CH2-CH3 |
|  | VH2-CH1-hinge-CH2-CH3* |
|  | VL1 |

TABLE 5-continued

| Format | Polypeptide chains |
|---|---|
| Format 7 | VH1-L-VH2-L-CH2-CH3<br>VH1-L-VH2-L-CH2-CH3*<br>VL1 |
| Format 8 | VH1-L-VL2-L-CH2-CH3<br>VL1-L-VH2-L-CH2-CH3* |
| Format 9 | VH1-L-VL2-L-CH2-CH3<br>VL1-L-VH2<br>L-CH2-CH3* |
| Format 10 | (P-L)$_n$-VH1-CH1-hinge-CH2-CH3-(L-P)$_n$<br>(P-L)$_n$-VH2-CH1-hinge-CH2-CH3*-(L-P)$_n$<br>VL1<br>VL2<br>n = 1-5 |

TABLE 6

| Linker name | Linker amino acid sequence | SEQ ID NO: |
|---|---|---|
| 1FU1 | ASLDTTAENQAKNEHLQKENERLLRDWNDVQG RFEKGS | 57 |
| 1DC1(13AA)$_2$ | ASEKNKRSTPYIERAEKNKRSTPYIERAGS | 58 |
| 1DC1(13AA)$_3$ | ASEKNKRSTPYIERAEKNKRSTPYIERAEKNK RSTPYIERAGS | 59 |
| AS(AP)$_{10}$GS | ASAPAPAPAPAPAPAPAPAPAPGS | 60 |
| AS(AP)$_{20}$GS | ASAPAPAPAPAPAPAPAPAPAPAPAPAPAPAP APAPAPAPAPGS | 61 |
| (EAAAK)$_4$ | ASAEAAAKEAAAKEAAAKEAAAKAGS | 62 |
| (EAAAK)$_8$ | ASAEAAAKEAAAKEAAAKEAAAKEAAAKEAAA KEAAAKEAAAKAGS | 63 |
| GS(G$_4$S)$_4$ | GSGGGGSGGGGSGGGGSGGGGS | 64 |
| GS(G$_4$S)$_8$ | GSGGGGSGGGGSGGGGSGGGGSGGGGSGGGGS GGGGSGGGGS | 65 |
| GS12X(G4S) | GSGGGGSGGGGSGGGGSGGGGSGGGGSGGGGS GGGGSGGGGSGGGGSGGGGSGGGGSGGGGS | 66 |
| GS16X(G4S) | GSGGGGSGGGGSGGGGSGGGGSGGGGSGGGGS GGGGSGGGGSGGGGSGGGGSGGGGSGGGGSGG GGSGGGGSGGGGSGGGGS | 67 |
| IgG1 hinge | EPKSCDKTHT | 92 |
| IgG2 hinge | ERKCCVE | 93 |
| IgG3 hinge | ELKTPLGDTTHT | 94 |
| IgG4 hinge | ESKYG | 95 |
| IgG1 engineered hinge | EPKSSDKTHT | 96 |
| IgA hinge | PSTPPTPSPSTPPTPSPS | 97 |
| IgD hinge | GGEEKKKEKEKEEQEERETKTP | 98 |

Polynucleotides, Vectors and Host Cells

The invention also provides for an isolated polynucleotide encoding any of the CH2-CH3 regions, antibody heavy chains, antibody light chains or polypeptides of the multimeric proteins of the invention.

The invention also provides for an isolated polynucleotide comprising the polynucleotide encoding the first CH2-CH3 region comprising a mutation Q311R, Q311K, T307P/L309Q, T307P/V309Q, T307P/L309Q/Q311R or T307P/V309Q/Q311R;

comprising the polynucleotide encoding the first CH2-CH3 region comprising a mutation Q311R, Q311K, T307P/L309Q, T307P/V309Q, T307P/L309Q/Q311R or T307P/V309Q/Q311R and the second CH2-CH3 region comprising a wild-type amino acid residue at positions 307, 309 and 311; or comprising a polynucleotide sequence of SEQ ID NOs: 27, 28, 29, 30, 31, 32, 33, 34, 35, 36, 37, 38, 39, 40, 41, 42, 43, 44, 45, 46, 87, 88 or 91.

The polynucleotide sequences of the invention may be operably linked to one or more regulatory elements, such as a promoter or enhancer, that allow expression of the nucleotide sequence in the intended host cell. The polynucleotide may be a cDNA.

The invention also provides for a vector comprising the polynucleotide of the invention. Such vectors may be plasmid vectors, viral vectors, vectors for baculovirus expression, transposon based vectors or any other vector suitable for introduction of the synthetic polynucleotide of the invention into a given organism or genetic background by any means. The polynucleotides of the invention may be operably linked to control sequences in the expression vector(s) that ensure the expression of the CH2-CH3 regions the polynucleotides encode. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

In some embodiments, the vector comprises the polynucleotides of SEQ ID NOs: 27, and 47.

In some embodiments, the vector comprises the polynucleotides of SEQ ID NOs: 28 and 47.

In some embodiments, the vector comprises the polynucleotides of SEQ ID NOs: 29 and 47.

In some embodiments, the vector comprises the polynucleotides of SEQ ID NOs: 30 and 47.

In some embodiments, the vector comprises the polynucleotides of SEQ ID NOs: 31 and 48.

In some embodiments, the vector comprises the polynucleotides of SEQ ID NOs: 32 and 48.

In some embodiments, the vector comprises the polynucleotides of SEQ ID NOs: 33 and 48.

In some embodiments, the vector comprises the polynucleotides of SEQ ID NOs: 34 and 48.

In some embodiments, the vector comprises the polynucleotides of SEQ ID NOs: 35 and 49.

In some embodiments, the vector comprises the polynucleotides of SEQ ID NOs: 36 and 49.

In some embodiments, the vector comprises the polynucleotides of SEQ ID NOs: 37 and 49.

In some embodiments, the vector comprises the polynucleotides of SEQ ID NOs: 38 and 49.

In some embodiments, the vector comprises the polynucleotides of SEQ ID NOs: 39 and 50.

In some embodiments, the vector comprises the polynucleotides of SEQ ID NOs: 40 and 50.

In some embodiments, the vector comprises the polynucleotides of SEQ ID NOs: 41 and 50.

In some embodiments, the vector comprises the polynucleotides of SEQ ID NOs: 42 and 50.

In some embodiments, the vector comprises the polynucleotides of SEQ ID NOs: 43 and 51.

In some embodiments, the vector comprises the polynucleotides of SEQ ID NOs: 44 and 51.

In some embodiments, the vector comprises the polynucleotides of SEQ ID NOs: 45 and 51.

In some embodiments, the vector comprises the polynucleotides of SEQ ID NOs: 46 and 51.

In some embodiments, the vector comprises the polynucleotides of SEQ ID NOs: 87 and 89.

In some embodiments, the vector comprises the polynucleotides of SEQ ID Nos: 87 and 90.

In some embodiments, the vector comprises the polynucleotides of SEQ ID NOs: 88 and 89.

In some embodiments, the vector comprises the polynucleotides of SEQ ID NOs: 88 and 90.

In some embodiments, the vector comprises the polynucleotides of SEQ ID NOs: 92 and 89.

In some embodiments, the vector comprises the polynucleotides of SEQ ID Nos: 92 and 90.

Table 7 shows the cDNA sequences of exemplary CH2-CH3 regions.

TABLE 7

| CH2-CH3 domain | cDNA SEQ ID NO: | cDNA polynucleotide sequence |
|---|---|---|
| IgG1 CH2-CH3 Q311K | 27 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311R | 28 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q | 29 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ Q311R | 30 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311K/ F405L | 31 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACAAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCCTGCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311R/ F405L | 32 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCCTGCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ F405L | 33 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC |

TABLE 7-continued

| CH2-CH3 domain | cDNA SEQ ID NO: | cDNA polynucleotide sequence |
|---|---|---|
| | | GGGAGGAGCAGTACAACAGCACGTACCGTGTGGTCA GCGTCCTCCCCGTCCAGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCCTGCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ Q311R/ F405L | 34 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCCTGCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311K/ K409R | 35 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACAAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCCGGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311R/ K409R | 36 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCCGGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ | 37 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG |
| K409R | | ACGGCGTGGAGGTGCATAATGCCAAGACAAAGCCGC GGGAGGAGCAGTACAACAGCACGTACCGTGTGGTCA GCGTCCTCCCCGTCCAGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCCGGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ Q311R/ K409R | 38 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCCGGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311K/ T366W | 39 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCTGCCTGCACAAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGTGGTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311R/ T366W | 40 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGTGGTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ | 41 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC |

TABLE 7-continued

| CH2-CH3 domain | cDNA SEQ ID NO: | cDNA polynucleotide sequence |
|---|---|---|
| L309Q/ T366W | | ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGTGGTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ Q311R/ T366W | 42 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGTGGTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311K/ T366S/ L368A/ Y407V | 43 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACAAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGAGCTGCGCCGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCGTGAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 Q311R/ T366S/ L368A/ Y407V | 44 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACAGGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGAGCTGCGCCGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCGTGAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 | 45 | CCTGAACTGCTGGGGGGACCGTCAGTCTTCCTCTTCC CCCCAAAACCCAAGGACACCCTCATGATCTCCCGGA |
| T307P/ L309Q/ T366S/ L368A/ Y407V | | CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGAGCTGCGCCGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCGTGAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T307P/ L309Q/ Q311R/ T366S/ L368A/ Y407V | 46 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCCCCGTCCAGCACCGGGACTGGCTGAATGG CAAGGAGTACAAGTGCAAGGTCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGAGCTGCGCCGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCGTGAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 wild-type | 47 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 K409R | 48 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCCGGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |

TABLE 7-continued

| CH2-CH3 domain | cDNA SEQ ID NO: | cDNA polynucleotide sequence |
|---|---|---|
| IgG1 CH2-CH3 F405L | 49 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGACCTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T366S/ L368A/ Y407V | 50 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGAGCTGCGCCGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCGTGAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG1 CH2-CH3 T366W | 51 | CCTGAACTGCTGGGGGGACCGTCAGTCTTCCTCTTCC CCCCAAAACCCAAGGACACCCTCATGATCTCCCGGA CCCCTGAGGTCACATGCGTGGTGGTGGACGTGAGCC ACGAAGACCCTGAGGTCAAGTTCAACTGGTACGTGG ACGGCGTGGAGGTGCATAATGCCAAGACAAAGCCGC GGGAGGAGCAGTACAACAGCACGTACCGTGTGGTCA GCGTCCTCACCGTCCTGCACCAGGACTGGCTGAATGG CAAGGAGTACAAGTGCAAGGTCTCCAACAAAGCCCT CCCAGCCCCCATCGAGAAAACCATCTCCAAAGCCAA AGGGCAGCCCCGAGAACCACAGGTGTACACCCTGCC CCCATCCCGGGATGAGCTGACCAAGAACCAGGTCAG CCTGTGGTGCCTGGTCAAAGGCTTCTATCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAAGCTCACCGTGG ACAAGAGCAGGTGGCAGCAGGGGAACGTCTTCTCAT GCTCCGTGATGCATGAGGCTCTGCACAACCACTACAC GCAGAAGAGCCTCTCCCTGTCTCCGGGTAAA |
| IgG2 CH2-CH3 Q311R | 87 | CCACCTGTGGCAGGACCGTCAGTCTTCCTCTTCCCCC CAAAACCCAAGGACACCCTCATGATCTCCCGGACCC CTGAGGTCACGTGCGTGGTGGTGGACGTGAGCCACG AAGACCCCGAGGTCCAGTTCAACTGGTACGTGGACG GCGTGGAGGTGCATAATGCCAAGACAAAGCCACGGG AGGAGCAGTTCAACAGCACGTTCCGTGTGGTCAGCG TCCTCACCGTTGTGCACCGGGACTGGCTGAACGGCAA GGAGTACAAGTGCAAGGTCTCCAACAAAGGCCTCCC AGCCCCCATCGAGAAAACCATCTCCAAAACCAAAGG GCAGCCCCGAGAACCACAGGTGTACACCCTGCCCCC ATCCCGGGAGGAGATGACCAAGAACCAGGTCAGCCT GACCTGCCTGGTCAAAGGCTTCTACCCCAGCGACATC GCCGTGGAGTGGGAGAGCAATGGGCAGCCGGAGAAC AACTACAAGACCACACCTCCCATGCTGGACTCCGAC GGCTCCTTCTTCCTCTACAGCAAGCTCACCGTGGACA AGAGCAGGTGGCAGCAGGGGAACGTCTTCTCATGCT |
| | | CCGTGATGCATGAGGCTCTGCACAACCACTACACGC AGAAGAGCCTCTCCCTGTCTCCGGGTAAA |
| IgG2 CH2-CH3 T307P/ V309Q/ Q311R | 88 | CCACCTGTGGCAGGACCGTCAGTCTTCCTCTTCCCCC CAAAACCCAAGGACACCCTCATGATCTCCCGGACCC CTGAGGTCACGTGCGTGGTGGTGGACGTGAGCCACG AAGACCCCGAGGTCCAGTTCAACTGGTACGTGGACG GCGTGGAGGTGCATAATGCCAAGACAAAGCCACGGG AGGAGCAGTTCAACAGCACGTTCCGTGTGGTCAGCG TCCTCCCCGTTCAGCACCGGGACTGGCTGAACGGCAA GGAGTACAAGTGCAAGGTCTCCAACAAAGGCCTCCC AGCCCCCATCGAGAAAACCATCTCCAAAACCAAAGG GCAGCCCCGAGAACCACAGGTGTACACCCTGCCCCC ATCCCGGGAGGAGATGACCAAGAACCAGGTCAGCCT GACCTGCCTGGTCAAAGGCTTCTACCCCAGCGACATC GCCGTGGAGTGGGAGAGCAATGGGCAGCCGGAGAAC AACTACAAGACCACACCTCCCATGCTGGACTCCGAC GGCTCCTTCTTCCTCTACAGCAAGCTCACCGTGGACA AGAGCAGGTGGCAGCAGGGGAACGTCTTCTCATGCT CCGTGATGCATGAGGCTCTGCACAACCACTACACGC AGAAGAGCCTCTCCCTGTCTCCGGGTAAA |
| wild-type IgG2 CH2-CH3 | 89 | CCACCTGTGGCAGGACCGTCAGTCTTCCTCTTCCCCC CAAAACCCAAGGACACCCTCATGATCTCCCGGACCC CTGAGGTCACGTGCGTGGTGGTGGACGTGAGCCACG AAGACCCCGAGGTCCAGTTCAACTGGTACGTGGACG GCGTGGAGGTGCATAATGCCAAGACAAAGCCACGGG AGGAGCAGTTCAACAGCACGTTCCGTGTGGTCAGCG TCCTCACCGTTGTGCACCAGGACTGGCTGAACGGCAA GGAGTACAAGTGCAAGGTCTCCAACAAAGGCCTCCC AGCCCCCATCGAGAAAACCATCTCCAAAACCAAAGG GCAGCCCCGAGAACCACAGGTGTACACCCTGCCCCC ATCCCGGGAGGAGATGACCAAGAACCAGGTCAGCCT GACCTGCCTGGTCAAAGGCTTCTACCCCAGCGACATC GCCGTGGAGTGGGAGAGCAATGGGCAGCCGGAGAAC AACTACAAGACCACACCTCCCATGCTGGACTCCGAC GGCTCCTTCTTCCTCTACAGCAAGCTCACCGTGGACA AGAGCAGGTGGCAGCAGGGGAACGTCTTCTCATGCT CCGTGATGCATGAGGCTCTGCACAACCACTACACGC AGAAGAGCCTCTCCCTGTCTCCGGGTAAA |
| IgG2 CH2-CH3 F405L/ K409R | 90 | CCACCTGTGGCAGGACCGTCAGTCTTCCTCTTCCCCC CAAAACCCAAGGACACCCTCATGATCTCCCGGACCC CTGAGGTCACGTGCGTGGTGGTGGACGTGAGCCACG AAGACCCCGAGGTCCAGTTCAACTGGTACGTGGACG GCGTGGAGGTGCATAATGCCAAGACAAAGCCACGGG AGGAGCAGTTCAACAGCACGTTCCGTGTGGTCAGCG TCCTCACCGTTGTGCACCAGGACTGGCTGAACGGCAA GGAGTACAAGTGCAAGGTCTCCAACAAAGGCCTCCC AGCCCCCATCGAGAAAACCATCTCCAAAACCAAAGG GCAGCCCCGAGAACCACAGGTGTACACCCTGCCCCC ATCCCGGGAGGAGATGACCAAGAACCAGGTCAGCCT GACCTGCCTGGTCAAAGGCTTCTACCCCAGCGACATC GCCGTGGAGTGGGAGAGCAATGGGCAGCCGGAGAAC AACTACAAGACCACACCTCCCATGCTGGACTCCGAC GGCTCCTTCTGCTCTACAGCCGGCTCACCGTGGACA AGAGCAGGTGGCAGCAGGGGAACGTCTTCTCATGCT CCGTGATGCATGAGGCTCTGCACAACCACTACACGC AGAAGAGCCTCTCCCTGTCTCCGGGTAAA |
| IgG2 CH2-CH3 T307P/ V309Q | 91 | CCACCTGTGGCAGGACCGTCAGTCTTCCTCTTCCCCC CAAAACCCAAGGACACCCTCATGATCTCCCGGACCC CTGAGGTCACGTGCGTGGTGGTGGACGTGAGCCACG AAGACCCCGAGGTCCAGTTCAACTGGTACGTGGACG GCGTGGAGGTGCATAATGCCAAGACAAAGCCACGGG AGGAGCAGTTCAACAGCACGTTCCGTGTGGTCAGCG TCCTCCCCGTTCAGCACCAGGACTGGCTGAACGGCAA GGAGTACAAGTGCAAGGTCTCCAACAAAGGCCTCCC AGCCCCCATCGAGAAAACCATCTCCAAAACCAAAGG GCAGCCCCGAGAACCACAGGTGTACACCCTGCCCCC ATCCCGGGAGGAGATGACCAAGAACCAGGTCAGCCT GACCTGCCTGGTCAAAGGCTTCTACCCCAGCGACATC GCCGTGGAGTGGGAGAGCAATGGGCAGCCGGAGAAC AACTACAAGACCACACCTCCCATGCTGGACTCCGAC GGCTCCTTCTTCCTCTACAGCAAGCTCACCGTGGACA |

TABLE 7-continued

| CH2-CH3 domain | cDNA SEQ ID NO: | cDNA polynucleotide sequence |
|---|---|---|
| | | AGAGCAGGTGGCAGCAGGGGAACGTCTTCTCATGCT CCGTGATGCATGAGGCTCTGCACAACCACTACACGC AGAAGAGCCTCTCCCTGTCTCCGGGTAAA |

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a eukaryotic cell, exemplary promoters include light and/or heavy chain immunoglobulin gene promoter and enhancer elements, cytomegalovirus immediate early promoter, herpes simplex virus thymidine kinase promoter, early and late SV40 promoters, promoter present in long terminal repeats from a retrovirus, mouse metallothionein-I promoter, and various art-known tissue specific promoters. Selection of the appropriate vector and promoter is well within the level of ordinary skill in the art.

Large numbers of suitable vectors and promoters are known; many are commercially available for generating recombinant constructs. Exemplary vectors are vectors for bacterial expression such as pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden) and eukaryotic vectors such as pWLneo, pSV2cat, pOG44, PXR1, pSG (Stratagene) pSVK3, pBPV, pMSG and pSVL (Pharmacia).

The invention also provides for a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archaeal cells. *Escherichia coli*, bacilli, such as *Bacillus subtilis*, and other enterobacteriaceae, such as *Salmonella, Serratia,* and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

The invention also provides for a method of making the isolated multispecific antibody of the invention, comprising culturing the host cell of the invention under conditions that the multispecific antibody is expressed, and purifying the multispecific antibody using protein A affinity chromatography.

Pharmaceutical Compositions, Administration and Methods of Treatment

The invention also provides for pharmaceutical compositions comprising the multispecific antibodies or the multimeric proteins of the invention and a pharmaceutically acceptable carrier. For therapeutic use, the multispecific antibodies or the multimeric proteins of the invention may be prepared as pharmaceutical compositions containing an effective amount of the multispecific antibodies or the multimeric proteins of the invention as an active ingredient in a pharmaceutically acceptable carrier. "Carrier" refers to a diluent, adjuvant, excipient, or vehicle with which the active compound is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the multispecific antibodies or the multimeric proteins of the invention in such pharmaceutical formulation may vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the multispecific antibodies or the multimeric proteins of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions may be supplied as a kit comprising a container that comprises the pharmaceutical composition as described herein. A pharmaceutical composition may be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

The multispecific antibodies and other multimeric proteins can be used to treat any condition in a human subject depending on their specificity.

While having described the invention in general terms, the embodiments of the invention will be further disclosed in the following examples that should not be construed as limiting the scope of the claims.

Example 1. Design of Fc Mutations that Potentially Reduce Fc Binding to Protein A FcRn and Z-domain of protein A bind to Fc at the interface between the CH2 and CH3 domains, contacting many of the same residues on the Fc. Since mouse IgG2a/b bind to Z-domain weaker than human IgG1 while all bind to FcRn, positions were identified in the Z-domain binding interface of human IgG1 CH2 domain which were not conserved in mouse IgG2a CH2 domain. FIG. 1A shows the alignment of human IgG1 and mouse IgG2a CH2 domains between residues 305 and 315. Since the residues at positions 305, 307, 309, 314 and 315 differed between human and mouse sequences, it was hypothesized that introducing the reverse mutations T307P and/or L309Q into human IgG1 may result in engineered IgG1 variants with decreased binding to protein A without affecting FcRn interaction. Valine 305 in human IgG1 is situated in a β-strand in the CH2 domain and does not interact with protein A or FcRn. While Leucine 314 and Asparagine 315 differ between human and mouse IgG, their differences are conservative (e.g. L314 in human IgG is changed to another hydrophobic residue: L/M314 in mouse IgG and N315 is changed to another polar residue: S315 in mouse IgG). Thus, it was reasoned that changes at positions 307 and 309 would have the most significant effect on human IgG1 interactions with protein A and FcRn.

Analysis of crystal structures of complexes of Z-domain (Z34C peptide, a disulfide-bonded two helix bundle derived from Z-domain, PDB ID 1L6X) and Fc revealed that IgG1 Fc residue Q311 interacted with F9, L13, R23, N24 and 127 on Z-domain (residue numbering according to SEQ ID NO: 99) mostly through hydrophobic interactions (FIG. 1B). Conversely, IgG1 Fc residue Q311 interacted with the mostly acidic surface of FcRn, containing E115 and E116 (corresponding to residues E4 and E5 of SEQ ID NO: 103) of the α-subunit of FcRn (PDB ID 4N0U). It was hypothesized that mutating Fc residue Q311 could differentially affect binding of the resulting variant(s) to Z-domain and FcRn. FIG. 1B shows the Fc residues in contact with FcRn or Z-domain at cutoff distance 5A.

Example 2. Generation of Monospecific and Bispecific Antibodies Used in the Studies Mutations T307A, Q311A, Q311K, Q311E, T307P/L309Q or T307P/L309Q/Q311R were engineered into both heavy chains of various monospecific antibodies using standard molecular biology techniques.

Bispecific mAbs were generated using common light chain technology or by promoting Fab arm exchange using Duobody® technology or Knob-in-Hole technology. In the common light chain technology, anti-TNFα and anti-αVβ5 antibodies which were known to share the light chain were used. In the knob-in-hole technology, either knob (T366W mutation) or hole (T366S, L368A, Y407V mutations) was introduced into the parental monospecific antibodies. In the Duobody® technology, F405L or K409R mutations were introduced into the parental monospecific antibodies.

The generated bispecific antibodies harbored the mutation (s) that potentially disrupt or reduce protein A binding (T307A, Q311A, Q311K, Q311E, T307P/L309Q and T307P/L309Q/Q311R) in one heavy chain only (e.g. asymmetrical mutations).

Abs were expressed in Expi293F cells (Invitrogen) according to the manufacturer's protocol, using a molar ratio of Light chain:Heavy chain plasmid of 3:1. Co-transfections were prepared using a 3:0.5:0.5 molar ratio of light chain: heavy chain 1:heavy chain 2 plasmid. Culture supernatants were harvested by filtration after 5-day expression periods. Titers were estimated using surface bilayer interferometry against isotype control standards of known concentration. Parental Abs were purified by protein A affinity chromatography using MabSelect SuRe resin (GE Healthcare) according to the manufacturer's protocol. Variants having altered protein A binding were purified by protein G affinity chromatography (GE Healthcare) according to the manufacturer's protocol.

Table 8 shows the generated monospecific antibodies.

Table 9 shows the generated bispecific (bs) antibodies.

TABLE 8

| mAb name | Specificity | Fc Mutation(s) | HC SEQ ID NO: | LC SEQ ID NO: |
|---|---|---|---|---|
| gp120-R | gp120 | K409R | 68 | 69 |
| RSV-L | RSV | F405L | 70 | 71 |
| RSV-L[Q311A] | RSV | Q311A/F405L | 72 | 71 |
| RSV-L[Q311K] | RSV | Q311K/F405L | 73 | 71 |
| RSV-L[Q311R] | RSV | Q311R/F405L | 74 | 71 |
| RSV-L[Q311H] | RSV | Q311H/F405L | 75 | 71 |
| RSV-L[TL] | RSV | T307P/L309Q/F405L | 76 | 71 |
| RSV-L[TLQ] | RSV | T307P/L309Q/Q311R/F405L | 77 | 71 |
| RSV-[I253D] | RSV | I253D | 78 | 71 |
| aVb5 | αVβ5 integrin | wild-type | 79 | 80 |
| TNF | TNF-α | wild-type | 81 | 80 |
| TNF-[Q311R] | TNF-α | Q311R | 82 | 80 |
| TNF-[TLQ] | TNF-α | T307P/L309Q/Q311R | 83 | 80 |
| TNF-knob[Q311R] | TNF-α | Q311R/T366W | 84 | 80 |
| TNF-knob[TLQ] | TNF-α | T307P/L309Q/Q311R/T366W | 85 | 80 |
| aVb5-hole | αVβ5 integrin | T366S/L368A/Y407V | 86 | 80 |

TABLE 9

| Antibody name | Arm 1 | Arm 2 |
|---|---|---|
| bs RSV-L | gp120-R | RSV-L |
| bsRSV-L[Q311A] | gp120-R | RSV-L[Q311A] |
| bsRSV-L[Q311K] | gp120-R | RSV-L[Q311K] |
| bsRSV-L[Q311R] | gp120-R | RSV-L[Q311R] |
| bsRSV-L[TL] | gp120-R | RSV-L[TL] |
| bsRSV-L[TLQ] | gp120-R | RSV-L[TLQ] |
| bsTNF | aVb5 | TNF |
| bsTNF-[Q311R] | aVb5 | TNF-[Q311R] |
| bsTNF-[TLQ] | aVb5 | TNF-[TLQ] |
| bsTNF-knob[Q311R] | aVb5-hole | TNF-knob[Q311R] |
| bsTNF-knob[TLQ] | aVb5-hole | TNF-knob[TLQ] |

Amino acid sequences of heavy and light chain of generated antibodies:

SEQ ID NO: 68
gp120-R HC
QVQLVQSGAEVKKPGASVKVSCQASGYRFSNFVIHWVRQAPGQRFEWMGWINPYNGN
KEFSAKFQDRVTFTADTSANTAYMELRSLRSADTAVYYCARVGPYSWDDSPQDNYYM
DVWGKGTTVIVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDS
DGSFFLYSRLTVDKSRWQQGNVFSCSVMHEALHNHYTQKSLSLSPGK

SEQ ID NO: 69
gp120-R LC
EIVLTQSPGTLSLSPGERATFSCRSSHSIRSRRVAWYQHKPGQAPRLVIHGVSNRASGISD
RFSGSGSGTDFTLTITRVEPEDFALYYCQVYGASSYTFGQGTKLERKRTVAAPSVFIFPPS
DEQLKSGTASVVCLLNNFYPREAKVQWKVDNALQSGNSQESVTEQDSKDSTYSLSSTLT
LSKADYEKHKVYACEVTHQGLSSPVTKSFNRGEC

SEQ ID NO: 70
RSV-L HC
QITLKESGPTLVKPTQTLTLTCTFSGFSLSTSGMGVSWIRQPPGKALEWLAHIYWDDDKR
YNPSLKSRLTITKDTSKNQVVLTMTNMDPVDTATYYCARLYGFTYGFAYWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFLLYSKLTV
DKSRWQQGNVFSCSVMHEALHNHYTQKSLSLSPGK

SEQ ID NO: 71
RSV LC
DIVMTQSPDSLAVSLGERATINCRASQSVDYNGISYMHWYQQKPGQPPKLLIYAASNPE
SGVPDRFSGSGSGTDFTLTISSLQAEDVAVYYCQQIIEDPWTFGQGTKVEIKRTVAAPSVF
IFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

SEQ ID NO: 72
RSV-L[Q311A] HC
QITLKESGPTLVKPTQTLTLTCTFSGFSLSTSGMGVSWIRQPPGKALEWLAHIYWDDDKR
YNPSLKSRLTITKDTSKNQVVLTMTNMDPVDTATYYCARLYGFTYGFAYWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHADWLNGKEYKCKVSNKALPAPIEKTISKAKGQPREPQVYTLPP
SRDELTKNQVSLTCLVKGFYPSDIAVEWESNGQPENNYKTTPPVLDSDGSFLLYSKLTV
DKSRWQQGNVFSCSVMHEALHNHYTQKSLSLSPGK

SEQ ID NO: 73
RSV-L[Q311K] HC
QITLKESGPTLVKPTQTLTLTCTFSGFSLSTSGMGVSWIRQPPGKALEWLAHIYWDDDKR

-continued

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLTVLHKDWLNGKEYKCKVSNKALPAPIEKTISKAKGQPREPQVYTLPP

SRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 74
RSV-L[Q311R] HC (Q311R/ F405L)
QITLKESGPTLVKPTQTLTLTCTFSGFSLSTSGMGVSWIRQPPGKALEWLAHIYWDDDKR

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLTVLHRDWLNGKEYKCKVSNKALPAPIEKTISKAKGQPREPQVYTLPP

SRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 75

RSV-L[Q311H] HC (Q311H/ F405L)

QITLKESGPTLVKPTQTLTLTCTFSGFSLSTSGMGVSWIRQPPGKALEWLAHIYWDDDKR

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLTVLHHDWLNGKEYKCKVSNKALPAPIEKTISKAKGQPREPQVYTLPP

SRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 76

RSV-L[TL] HC (T307P/L309Q/ F405L)

QITLKESGPTLVKPTQTLTLTCTFSGFSLSTSGMGVSWIRQPPGKALEWLAHIYWDDDKR

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLPVQHQDWLNGKEYKCKVSNKALPAPIEKTISKAKGQPREPQVYTLPP

SRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 77

RSV-L[TLQ] HC (T307P/L309Q/Q311R/F405L)

QITLKESGPTLVKPTQTLTLTCTFSGFSLSTSGMGVSWIRQPPGKALEWLAHIYWDDDKR

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLPVQHRDWLNGKEYKCKVSNKALPAPIEKTISKAKGQPREPQVYTLPP

SRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 78
RSV-L[I253D] HC (I253D/F405L)
QITLKESGPTLVKPTQTLTLTCTFSGFSLSTSGMGVSWIRQPPGKALEWLAHIYWDDDKR

YNPSLKSRLTITKDTSKNQVVLTMTNMDPVDTATYYCARLYGFTYGFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMDSRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFLLYSKLTV

DKSRWQQGNVFSCSVMHEALHNHYTQKSLSLSPGK

SEQ ID NO: 79
aVb5 HC
QVQLVESGGGVVQPGRSRRLSCAASGFTFSRYTMHWVRQAPGKGLEWVAVISFDGSNK

YYVGSVKGRFTISRDNSENTLYLQVNILRAEDTAVYYCAREARGSYAFDIWGQGTMVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGK

SEQ ID NO: 80
TNF and anti-aVb5 LC
EIVLTQSPATLSLSPGERATLSCRASQSVSSYLAWYQQKPGQAPRLLIYDASNRATGIPAR

FSGSGSGTDFTLTISSLEPEDFAVYYCQQRSNWPPFTFGPGTKVDIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

SEQ ID NO: 81
TNF HC
EVQLVESGGGVVQPGGSLSLSCAASGFIFSSYAMHWVRQAPGNGLEWVAFMSYDGSNK

KYADSVKGRFTISRDNSENTLYLQMNSLRAEDTAVYYCARDRGIAAGGNYYYYGMDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

SEQ ID NO: 82
TNF-[Q311R] HC
EVQLVESGGGVVQPGGSLSLSCAASGFIFSSYAMHWVRQAPGNGLEWVAFMSYDGSNK

KYADSVKGRFTISRDNSENTLYLQMNSLRAEDTAVYYCARDRGIAAGGNYYYYGMDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEV

-continued

HNAKTKPREEQYNSTYRVVSVLTVLHRDWLNGKEYKCKVSNKALPAPIEKTISKAKGQ

PREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

SEQ ID NO: 83
TNF-[TLQ] HC (T307P/L309Q/Q311R):
EVQLVESGGGVVQPGGSLSLSCAASGFIFSSYAMHWVRQAPGNGLEWVAFMSYDGSNK

KYADSVKGRFTISRDNSENTLYLQMNSLRAEDTAVYYCARDRGIAAGGNYYYYGMDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEV

HNAKTKPREEQYNSTYRVVSVLPVQHRDWLNGKEYKCKVSNKALPAPIEKTISKAKGQ

PREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

SEQ ID NO: 84
TNF-knob[Q311R] HC (Q311R/T366W)
EVQLVESGGGVVQPGGSLSLSCAASGFIFSSYAMHWVRQAPGNGLEWVAFMSYDGSNK

KYADSVKGRFTISRDNSENTLYLQMNSLRAEDTAVYYCARDRGIAAGGNYYYYGMDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEV

HNAKTKPREEQYNSTYRVVSVLTVLHRDWLNGKEYKCKVSNKALPAPIEKTISKAKGQ

PREPQVYTLPPSREEMTKNQVSLWCLVKGFYPSDIAVEWESNGQPENNYKTTPPVLDSD

GSFFLYSKLTVDKSRWQQGNVFSCSVMHEALHNHYTQKSLSLSPGK

SEQ ID NO: 85
TNF-knob[TLQ] HC (T307P/L309Q/Q311R/T366W)
EVQLVESGGGVVQPGGSLSLSCAASGFIFSSYAMHWVRQAPGNGLEWVAFMSYDGSNK

KYADSVKGRFTISRDNSENTLYLQMNSLRAEDTAVYYCARDRGIAAGGNYYYYGMDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEV

HNAKTKPREEQYNSTYRVVSVLPVQHRDWLNGKEYKCKVSNKALPAPIEKTISKAKGQ

PREPQVYTLPPSREEMTKNQVSLWCLVKGFYPSDIAVEWESNGQPENNYKTTPPVLDSD

GSFFLYSKLTVDKSRWQQGNVFSCSVMHEALHNHYTQKSLSLSPGK

SEQ ID NO: 86
aVb5-hole HC (T366S/L368A/Y407V)
QVQLVESGGGVVQPGRSRRLSCAASGFTFSRYTMHWVRQAPGKGLEWVAVISFDGSNK

YYVGSVKGRFTISRDNSENTLYLQVNILRAEDTAVYYCAREARGSYAFDIWGQGTMVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

Example 3. Effect of T307, L309 and/or Q311 Mutations to Binding to Z Domain and FcRn Binding of Monospecific IgG1 Variants to Z Domain Monospecific anti-RSV antibodies harboring Fc mutations as shown in Table 8 were used in the study.

RSV-L eluted from protein A resin at pH 4.09. Whereas T307A mutation had no effect on protein A binding (data not shown), T307P/L309Q mutation (mAb RSV-L[TL]) resulted in a modest decrease in binding to protein A, causing this mAb to elute at pH 4.48. Additional weakening effect on protein A binding could be achieved by symmetrical Q311K or Q311R mutations, but not by Q311A mutation. Introducing a triple mutation T307P/L309Q/Q311R (mAb RSV-L[TLQ]) further disrupted interaction with protein A, as evidenced by elevated elution pH of 4.70. Table 10 shows the elution pH values of the generated IgG1 variants.

These results demonstrated that Q311K, Q311R, T307P/L309Q and T307P/L309Q/Q311R symmetrical mutations each decreased binding of the variant IgG1 to protein A, potentially allowing purification and separation of the bispecific antibodies harboring asymmetrical mutations generated from parental variant IgG1s based on differential protein A elution.

TABLE 10

Elution pH values of the generated IgG1 variants

| mAb | Elution pH | FcRn IC$_{50}$ (nM) |
|---|---|---|
| RSV-L | 4.09 | 79.3 |
| RSV-L[Q311A] | 4.07 | 41.1 |
| RSV-L[Q311K] | 4.72 | 45.6 |
| RSV-L[Q311R] | 4.67 | 18.2 |
| RSV-L[Q311H] | NA | 59.1 |
| RSV-L[TL] | 4.48 | NA |
| RSV-L[TLQ] | 4.70 | 79.6 |

Binding of the IgG1 Variants to FcRn

Figure 2A:
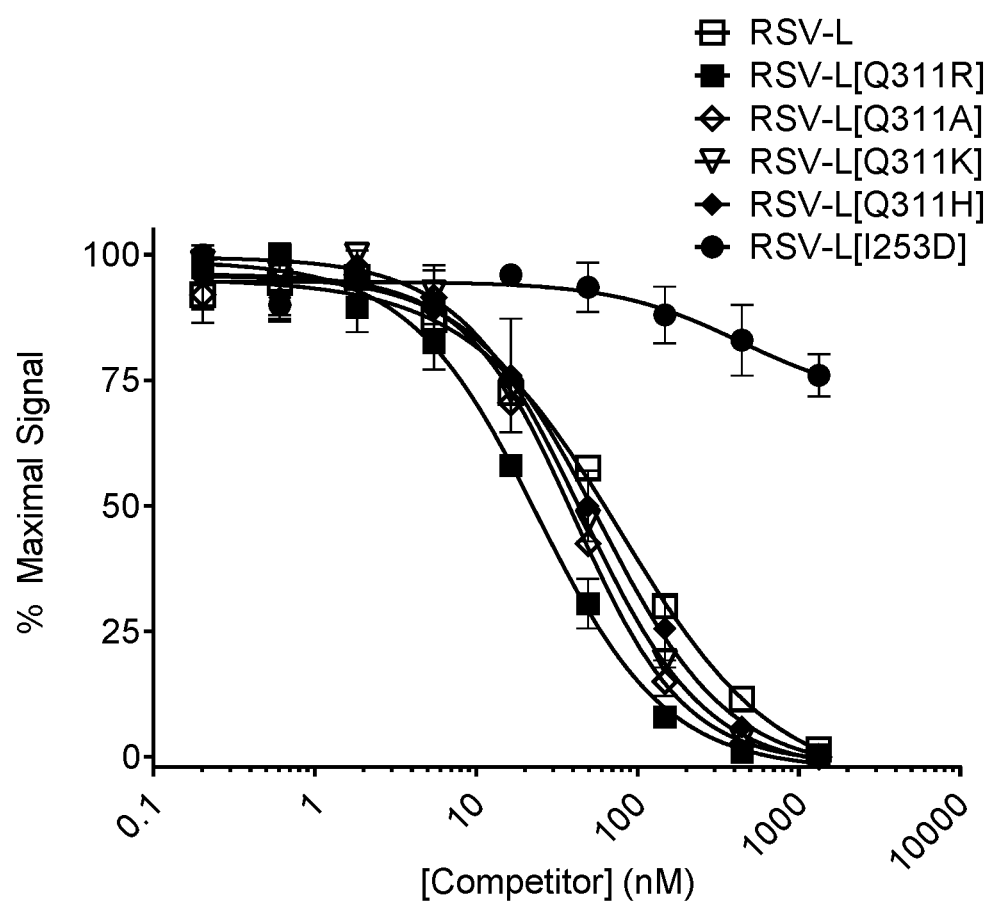
FIG. 2A shows a dose response curve of competition binding of indicated monospecific antibodies with the mAb RSV-L for FcRn using AlphaScreen assay. The graph displays % maximum signal plotted vs concentration of competitor.
Figure 2B:
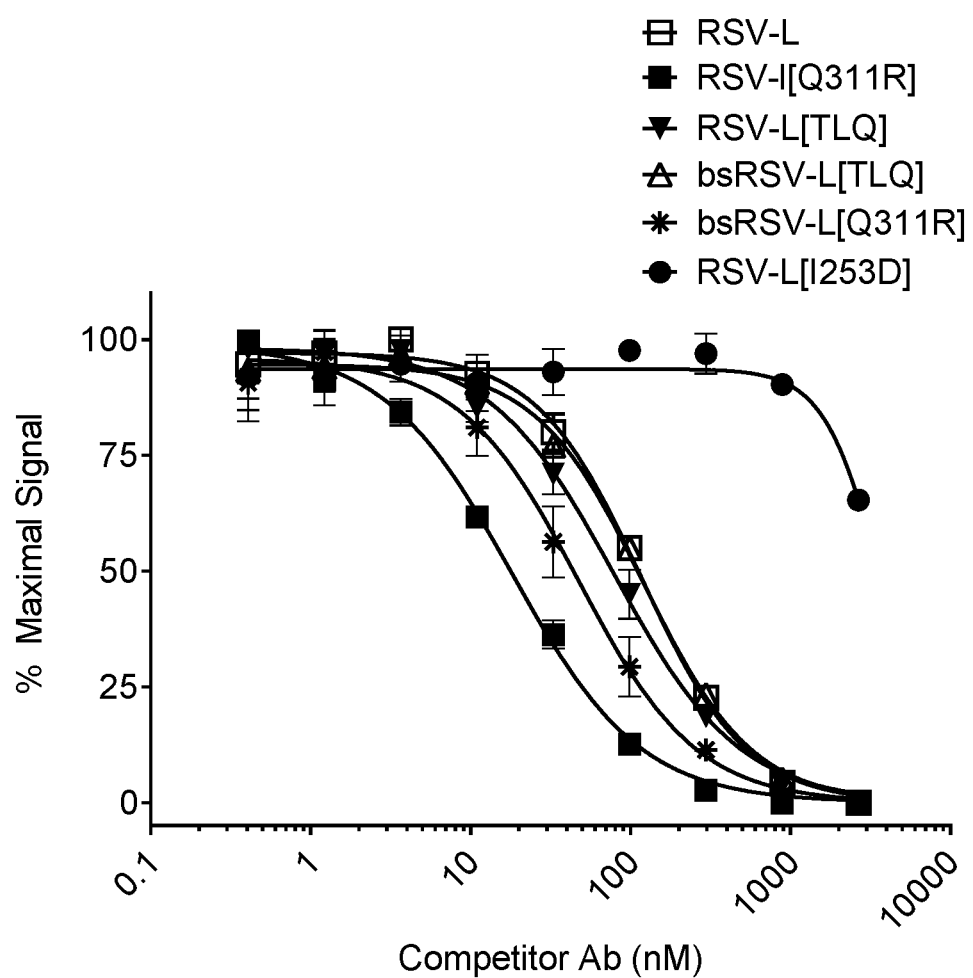
FIG. 2B shows a dose response curve of competition binding of indicated monospecific or bispecific antibodies with the mAb RSV-L for FcRn using AlphaScreen assay. The graph displays % maximum signal plotted vs concentration of competitor.
Figure 3A:
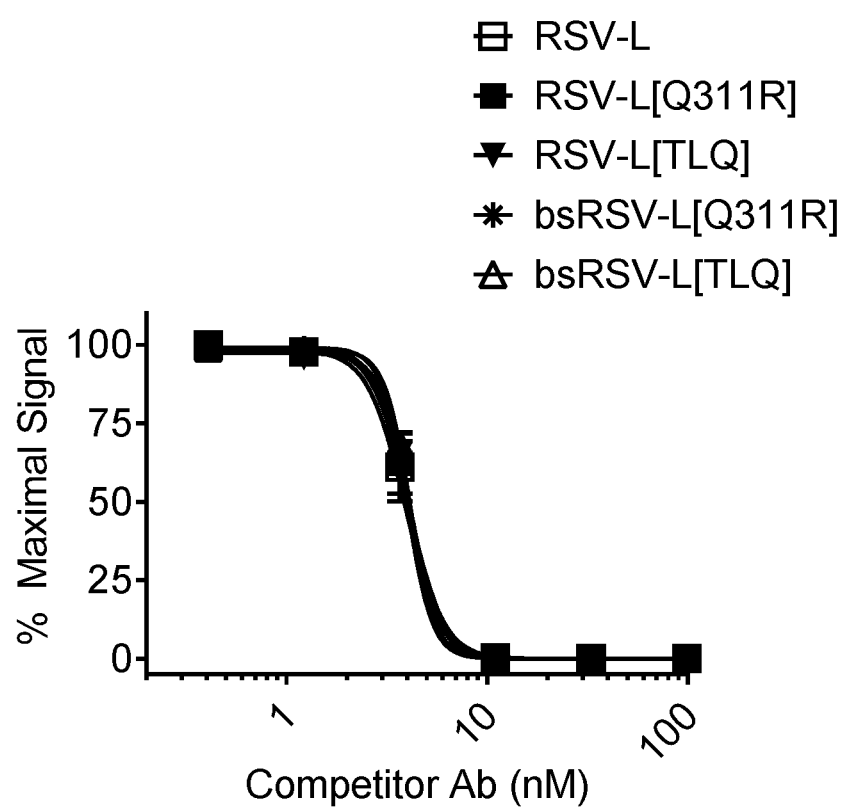
FIG. 3A shows a dose response curve of competition binding of indicated monospecific or bispecific antibodies with the mAb RSV-L for FcγRI using AlphaScreen assay. The graph displays % maximum signal plotted vs concentration of competitor.
Figure 3B:
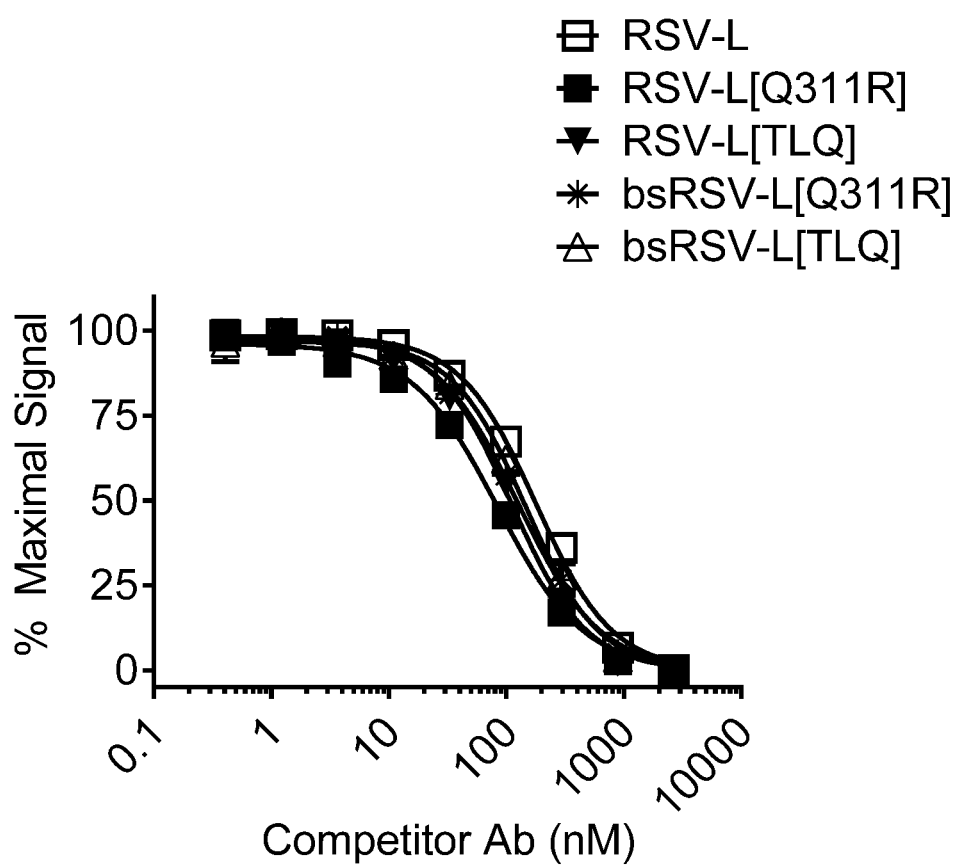
FIG. 3B shows a dose response curve of competition binding of indicated monospecific or bispecific antibodies with the mAb RSV-L for FcγRIIa using AlphaScreen assay. The graph displays % maximum signal plotted vs concentration of competitor.

None of the introduced single position mutants at position 311—(Q311R, Q311A, Q311K and Q311H) disrupted interaction of the monospecific antibodies with FcRn. Q311R mutation resulted in modestly enhanced ability to bind FcRn, suggesting that this mutation may offer extended serum half-life. RSV-L[TLQ] bound FcRn with similar affinity when compared to RSV-L. Bispecific IgG1 antibodies with asymmetrical F405L Q311R (bsRSV-L[Q311R]) or F405L/T307P/L309Q/Q311R mutations (bsRSV-L[TLQ]) also bound FcRn with identical affinity when compared to the wild-type IgG1. FIG. 2A shows the dose response curve for competition binding of the IgG1 variants with Q311R, Q311A, Q311K or Q311H mutations to FcRn. FIG. 2B shows the dose response curve for competition binding of the IgG1 variants with either symmetrical (e.g. monospecific mAbs RSV-L, RSV-L[Q311R], RSV-L[TLQ]) or asymmetrical (e.g. bispecific mAbs bsRSV-L[Q311R], bsRSV-L[TLQ]) Q311R or T307P/L309Q/Q311R mutations to FcRn. I253D mutation is known to disrupt FcRn interaction and was used as a negative control.

Mutations at Q311R, Q311A, Q311K or Q311H did not impair FcRn interaction. Mutation of Q311R enhanced FcRn interaction. Incorporation of T307P/L309Q/Q311R mutations in one or both heavy chains did not impair FcRn interaction. These results suggested that bispecific antibodies harboring asymmetrical Q311R or T307P/L309Q/Q311R mutations can be isolated and purified from their parental monospecific antibodies by differential protein A purification. Further, these antibodies may have longer serum half-life when compared to wild-type IgG1.

Methods

T307A, Q311A, Q311K, Q311R, Q311H, T307P/L309Q and T307P/L309Q/Q311R mutations were engineered into monospecific parental anti-RSV or anti-gp120 antibodies. The parental antibodies were further engineered to have a F405L mutation (anti-RSV mAb) or a K409R mutation (anti-gp120 mAb) in order to generate bispecific anti-RSV/gp120 antibodies using Fab arm exchange. The extent to which the mutations could modulate binding to Z-domain and FcRn was evaluated.

Z-domain used in the experiments has an amino acid sequence of SEQ ID NO: 1.

Protein A Binding

For each parental mAb harboring the mutations on both arms, 1 mg was loaded onto a 1 mL mAbSelect sure column (GE Healthcare) and eluted at 1 mL/min using a 30 mL gradient from 1×PBS pH 7.2 to 50 mM citrate pH 3.5. Absorbance at 280 nm and pH were monitored. The pH value at the peak maximum was used to determine the elution pH for preparative experiments.

FcRn Binding

FcRn binding was evaluated in vitro using an alphascreen assay. In these assays a biotinylated IgG was bound to a streptavidin-coated donor bead and His-tagged FcRn was bound to a Ni-coated acceptor bead. Binding between the two proteins resulted in a luminescence signal. The binding was competed using unlabeled wild-type or mutant IgG, resulting in a dose-dependent decrease in signal. mAbs were biotinylated using the SureLINK™ Chromophoric Biotin Labeling kit (KPL Inc.), according to the manufacturer's protocol. His-tagged FcRn was purchased from Sino Biological. Assays were performed in 1×PBS adjusted to pH 6.0, supplemented with 0.05% (w/v) bovine serum albumin (BSA) and 0.01% (w/v) Tween®-20. Biotinylated wild-type IgG1 at 1 µg/mL was bound to streptavidin-conjugated donor beads, and His-tagged FcRn at 0.2 µg/mL was bound to a nickel-conjugated acceptor bead. Competitor Abs were prepared at 0.4 mg/mL and were serially diluted by 3-fold for each point. Luminescence between 520-620 nm was recorded using an EnVision® plate reader (Perkin Elmer). Data were analyzed using Prism 6.01 software (GraphPad Software, Inc.) software and fit using a 4-parameter competition model, as described previously (Vafa et al., *Methods* 65:114-126, 2014).

Example 4. T307P, L309Q, and Q311R Mutations have No Effect on Fcγ Receptor (FcγR) Binding or Antibody Stability Mutations in the CH2-CH3 interface have been reported to alter the structure of the Fc, leading to increased dynamics of the Fc, decreased thermal stability, and altered interaction with Fcγ receptors (Majumdar et al., *MAbs* 7:84-95, 2015). To address whether the Q311R or T307P/L309Q/Q311R mutations have a similar impact on the structure of the Fc, antibodies harboring these mutations were assessed for their abilities to bind Fcγ receptors and for their thermal stabilities.

Neither symmetrical nor asymmetrical Q311R or T307P/L309Q/Q311R mutations in monospecific or bispecific antibodies, respectively, had an effect on the ability of the variant IgG1 to interact with Fcγ receptors in vitro. This result was somewhat expected since Fcγ receptors bind to the C$_H$2-hinge interface instead of the CH2-CH3 interface. The results also suggested that the introduced mutations did not perturb the overall structure of the Fc. FIG. 3A, FIG. 3B, FIG. 3C and FIG. 3D show the dose repose curve of competition binding of select antibodies to FcγRI, FcγRIIa, FcγRIIb, and FcγRIIIa, respectively. The graphs display % maximum signal plotted vs concentration of competitor.

Comparison of the $T_m$ values of engineered IgGs demonstrated that Q311R or T307P/L309Q/Q311R mutations did no perturb the thermal stability of the mAb. Table 11 shows the parameters for differential scanning calorimetry (Tm and enthalpy values) for the antibodies tested. Together, these results suggest the effects of the Q311R and T307P/L309Q/Q311R mutations are localized to protein A and FcRn interaction.

TABLE 11

| mAb | $C_H2$ and Fab Tm (° C.) | $C_H2$ and Fab ΔH (cal/mol) | $C_H3$ Tm (° C.) | $C_H3$ ΔH (cal/mol) |
|---|---|---|---|---|
| RSV-L | 70.97 ± 0.01 | 6.78 ± 0.02 × 10⁵ | 81.75 ± 0.03 | 1.45 ± 0.02 × 10⁵ |
| RSV-L[Q311R] | 72.10 ± 0.02 | 6.45 ± 0.13 × 10⁵ | 81.66 ± 0.03 | 1.65 ± 0.02 × 10⁵ |
| RSV-L[TLQ] | 71.55 ± 0.01 | 6.81 ± 0.03 × 10⁵ | 81.55 ± 0.04 | 1.61 ± 0.03 × 10⁵ |

Methods

Alpha-screen assay was used to assess binding of the IgG1 variants to FcγR using protocol described in Example 2 with minor modifications. The soluble extracellular domains of FcγRs which contained C-terminal His-tags were purchased from R&D systems. Assays were performed in 1×PBS pH 7.2, supplemented with 0.05% (w/v) bovine serum albumin (BSA) and 0.01% (w/v) Tween-20. Biotinylated wild-type IgG1 at 1 µg/mL was bound to streptavidin-conjugated donor beads, and His-tagged FcγRs were bound to a nickel-conjugated acceptor bead. For FcγRI, a biotinylated IgG1-L234A/L235A mutant which bound the receptor weaker than wild-type IgG1, was used to increase the signal window. The concentrations of FcγRs used were 200 ng/mL (FcγRI and FcγRIIIa), 10 ng/mL (FcγRIIa) or 14 ng/mL (FcγRIIb). Competitor Abs were prepared at 0.4 mg/mL and were serially diluted by 3-fold for each point.

Differential scanning calorimetry (DSC) was used to determine the $T_m$ and enthalpies of unfolding of antibodies. Samples were diluted to 1 mg/mL in 1×PBS pH 7.2. Samples were equilibrated to 25° C. for 15 min prior to temperature ramping from 25-95° C. at a rate of 1° C./min. Data was analyzed using Origin software.

Example 5. Separation of Bispecific Antibodies from Parental Monospecific mAbs after in Vitro Fab Arm Exchange of Purified Antibodies by Elution from Protein a Resin Introduction of asymmetric Q311R or T307P/L309Q/Q311R mutations into bispecific antibodies facilitated their purification from parental monospecific mAbs.

A 1:1:1 mixture of parental antibodies RSV-L[TLQ] and gp120-R and the bispecific bsRSV-L[TLQ] generated after in vitro Fab arm exchange were purified by differential protein A affinity chromatography and the elution peaks were pooled and analyzed by HIC.

Figure 4B:
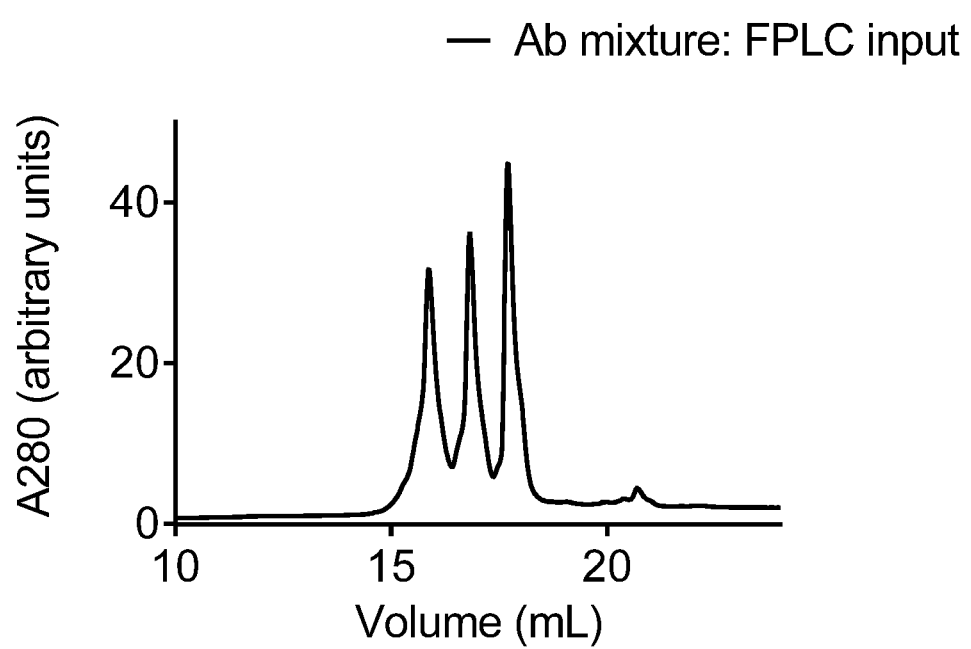
FIG. 4B shows HIC chromatogram of mixture of equimolar amount of antibodies RSV-L[TLQ] and gp120-R and bsRSV-L[TLQ] generated using Fab arm exchange.
Figure 4C:
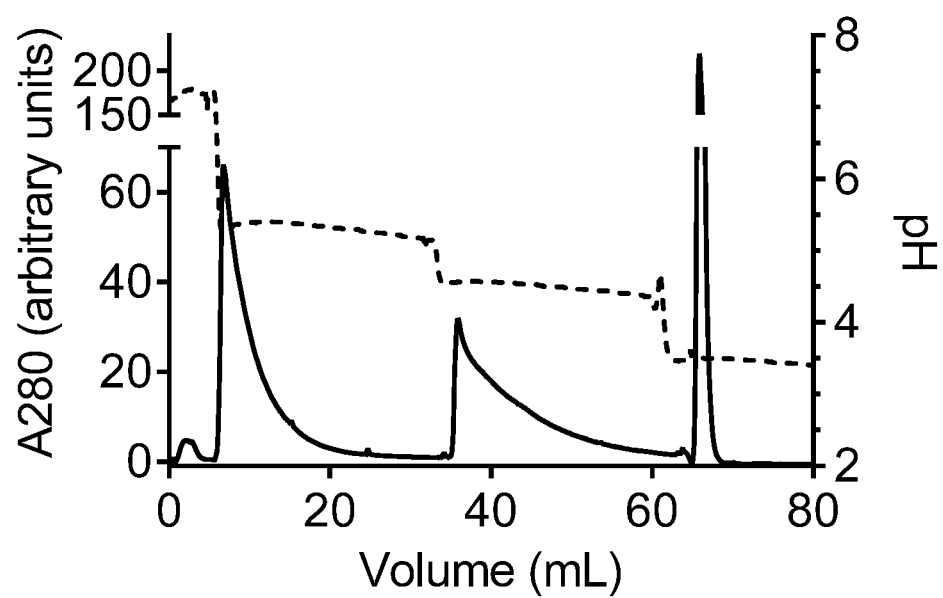
FIG. 4C shows the elution profile of a sample of a mixture of antibodies RSV-L[TLQ], gp120-R and bsRSV-L[TLQ] generated using Fab arm exchange from protein A resin.
Figure 4D:
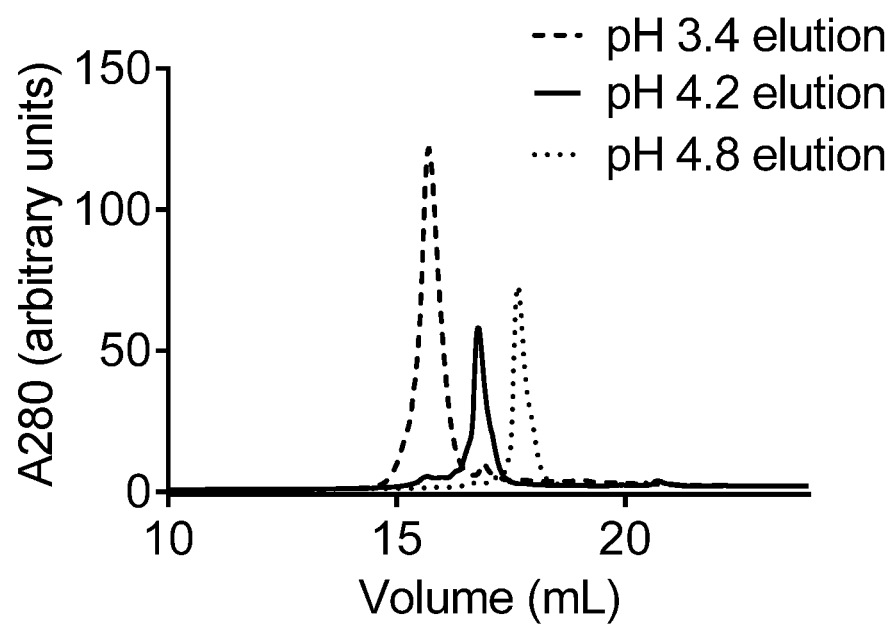
FIG. 4D shows HIC chromatogram of protein A elution peaks.
Figure 5A:
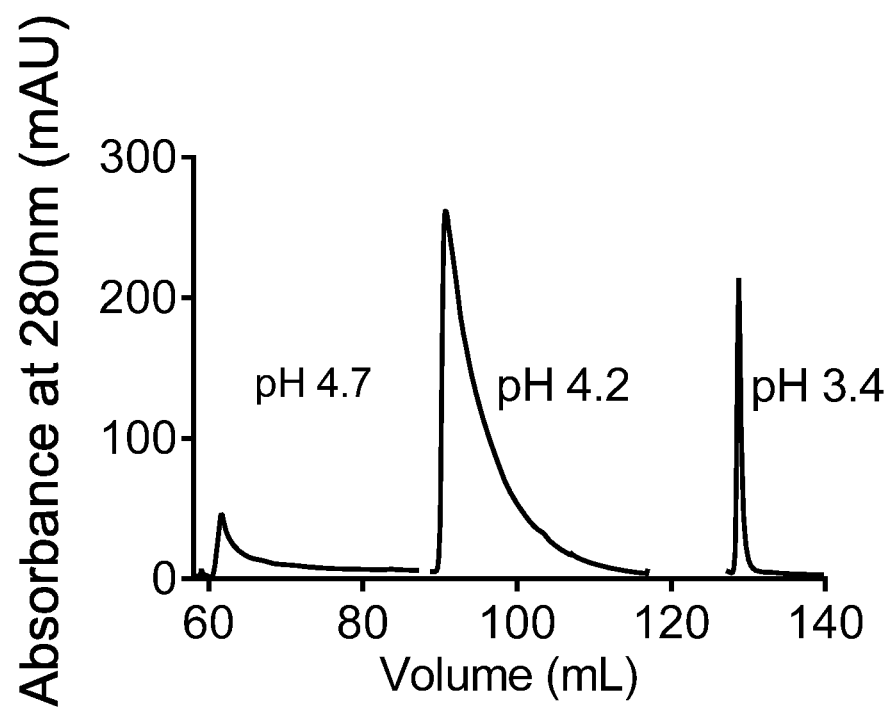
FIG. 5A shows the elution profile of a sample of in-supernatant Fab arm exchanged bsRSV-L[TLQ].
Figure 6A:
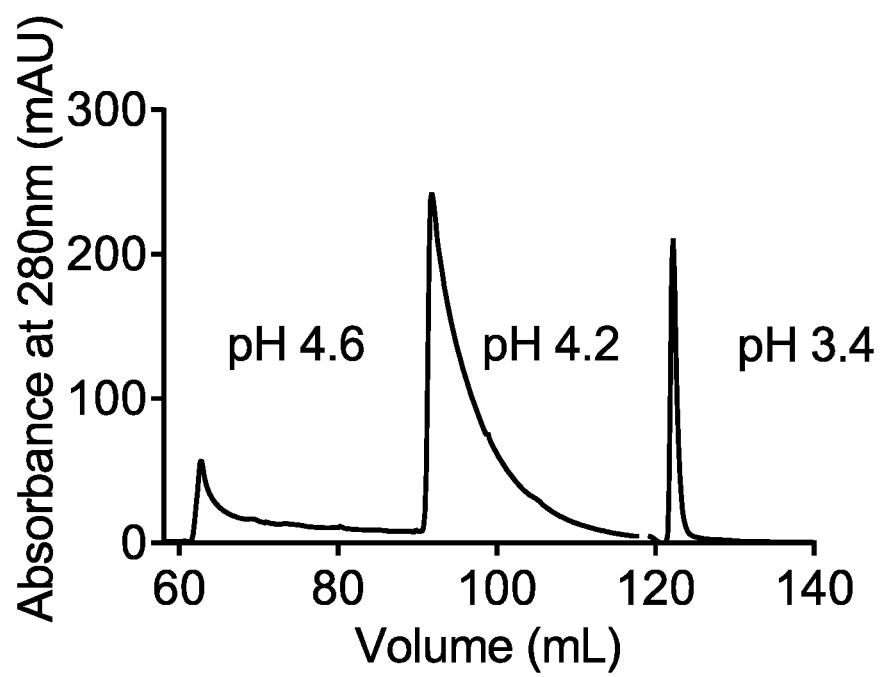
FIG. 6A shows protein A chromatogram of a sample of in-supernatant Fab arm exchanged bsRSV-L[Q311R] showing three distinct peaks eluting at pH 4.6, 4.2 and 3.4.
Figure 6C:
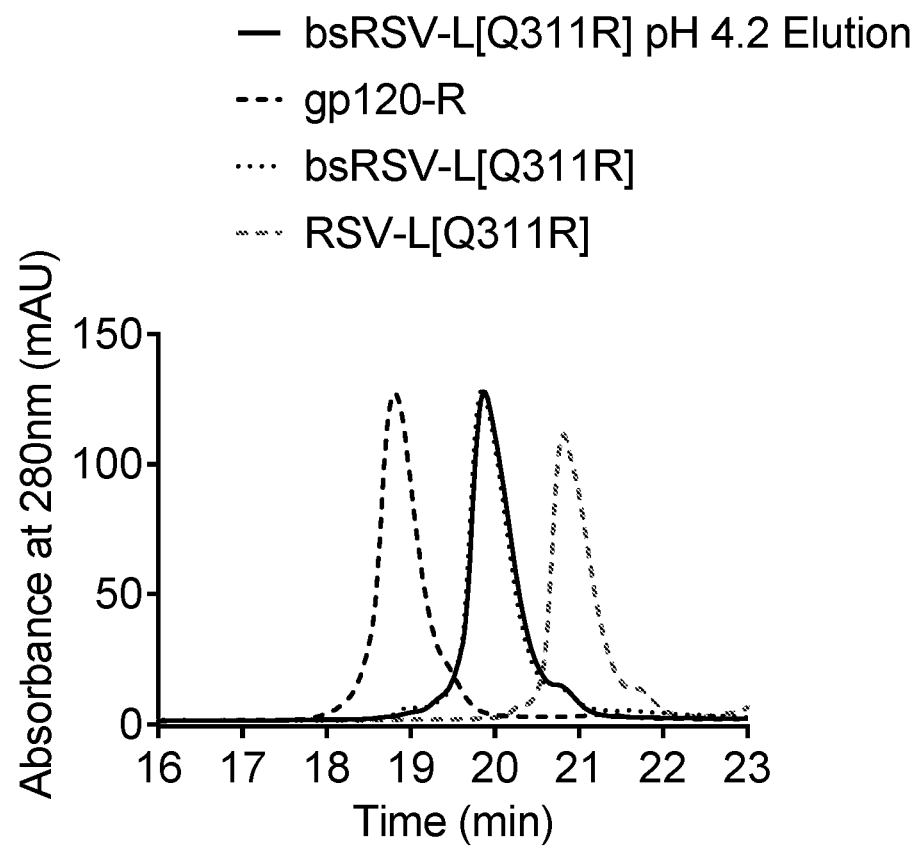
FIG. 6C shows HIC analyses of protein A affinity column pH 4.2 eluates of a sample from in-supernatant Fab arm exchanged bsRSV-L[Q311R].

FIG. 4A shows that both parental and the bispecific mAb could be separated using HIC chromatograph using developed conditions. FIG. 4B shows HIC chromatograph of the equimolar mixture of the antibodies injected into protein A column. FIG. 4C shows the elution profile of the antibody mixture from protein A resin, which resulted in three distinct elution peaks at pH 4.7, pH 4.2, and pH 3.4, consistent with the presence of two parental antibodies and the bispecific antibody. FIG. 4D shows the HIC analyses of the protein A elution peaks. Analyses of the elution peaks by HIC demonstrated that the high pH elution (pH 4.8) contained mostly the parental RSV-L[TLQ] mAb while the pH 3.4 elution contained mostly the gp120-R parental mAb. The intermediate pH elution (pH 4.2) contained about 94% pure bispecific bsRSV-L[TLQ] mAb. Table 12 shows the elution purity of bsRSV-L[TLQ] from differential protein A purification.

TABLE 12

| Elution pH | % RSV-L[TLQ] | % bsRSV-L[TLQ] | % gp120-R |
|---|---|---|---|
| 4.6 | >99 | N.D.* | N.D. |
| 4.2 | N.D. | 94 | 6 |
| 3.4 | N.D. | 3 | 97 |

*N.D. = not detected

Methods

The parental antibodies RSV-L[TLQ] and gp120-R and the bispecific bsRSV-L[TLQ] mAb were used in the study.

RSV-L[TLQ] was purified using protein G affinity chromatograph and dialyzed into 1×PBS. gp120-R was purified by protein A affinity chromatography and dialyzed into 1×PBS. The two parental mAbs were then subjected to Fab arm exchange at 1 mg/mL. Briefly, 5 mg of each parental antibody were mixed in buffer containing 1×PBS, 75 mM 2-mercaptoethylamine and incubated at 31° C. for 5 hr followed by extensive dialysis against 1×PBS. The resulting material, which contained >95% BsAb, was then mixed in a 1:1:1 molar ratio with the two purified parental mAbs and the mixture was used in differential protein A purification experiments.

Differential protein A purification was carried out using a 1 mL mAbSelect Sure column (GE Healthcare). The mixture was eluted in 3 steps using buffers containing 50 mM citrate pH 4.7, pH 4.2 or pH 3.4. Elution fractions were collected and concentrated to >1 mg/mL prior to analysis.

Analysis of the elution peaks from the differential protein A purification was analyzed by hydrophobic interaction chromatography (HIC) using a butyl NPR column (Tosoh Biosciences). Approximately 30 ug of each sample were injected onto the column and eluted using a 0 to 100% gradient of buffers containing 100 mM sodium phosphate pH 6.0, 1.5 M (NH$_4$)2SO$_4$, or 100 mM sodium phosphate pH 6.0.

Example 6. Separation of Bispecific Antibodies from Parental Monospecific mAbs after in Vitro Fab Arm Exchange in Crude Supernatants by Elution from Protein a Resin Introduction of asymmetric Q311R or T307P/L309Q/Q311R into bispecific antibodies generated from in-supernatant crossed material facilitated the purification of the generated bispecific antibodies from parental antibodies.

The DuoBody® technology to generate bispecific antibodies require parental mAbs to be individually purified prior to Fab arm exchange. However, cFAE reactions often have residual amounts of bivalent parental mAb which can lead to the requirement for additional downstream polishing steps. Thus, the use of the differential Protein A chromatography using pH gradients can simplify the purification of the bispecific antibodies. Another method to decrease the number of purification steps is to perform Fab arm exchange protocols using culture supernatants. In this method, parental mAb titers are precisely determined such that parental mAbs are mixed in a 1:1 molar ratio. By conducting the controlled Fab arm exchange with culture supernatants, the cost of generating bispecific antibodies can be reduced since there is one less Protein A purification step and time saving of having to conduct not having to run two parental antibody purification and characterizations.

bsRSV-L[TLQ] and bsFSV-L[Q311R] were generated using Fab arm exchange in cell culture supernatants containing equivalent quantities of parental antibodies RSV-L [TLQ] and gp120-R and the resulting samples subject to protein A affinity column FIG. 5A shows protein A chromatogram of a sample of in-supernatant Fab arm exchanged bsRSV-L[TLQ] showing three distinct peaks eluting at pH 4.7, 4.2 and 3.4.

FIG. 5B shows HIC analyses of protein A affinity column pH 4.7 eluates of a sample from in-supernatant Fab arm exchanged bsRSV-L[TLQ].

FIG. 5C shows HIC analyses of protein A affinity column pH 4.2 eluates of a sample from in-supernatant Fab arm exchanged bsRSV-L[TLQ].

FIG. 5D shows HIC analyses of protein A affinity column pH 3.4 eluates of a sample from in-supernatant Fab arm exchanged bsRSV-L[TLQ].

FIG. 6A shows protein A chromatogram of a sample of in-supernatant Fab arm exchanged bsRSV-L[Q311R] showing three distinct peaks eluting at pH 4.7, 4.2 and 3.4.

FIG. 6B shows HIC analyses of protein A affinity column pH 4.7 eluates of a sample from in-supernatant Fab arm exchanged bsRSV-L[Q311R].

FIG. 6C shows HIC analyses of protein A affinity column pH 4.2 eluates of a sample from in-supernatant Fab arm exchanged bsRSV-L[Q311R].

FIG. 6D shows HIC analyses of protein A affinity column pH 3.4 eluates of a sample from in-supernatant Fab arm exchanged bsRSV-L[Q311R].

For the in-supernatant Fab arm exchange producing bsRSV-L[TLQ], remaining parental RSV-L[TLQ] was removed by elution at pH 4.7 (FIG. 5B) and remaining parental gp120-R was removed by elution at pH 3.4 (FIG. 5D). Solely bsRSV-L[TLQ] eluted at pH 4.2 (FIG. 5C). Some bsRSV-L[TLQ] eluted at pH 3.4 (FIG. 5D) and at pH 4.7 (FIG. 5B) which resulted in a decreased final yield of purified bsRSV-L[TLQ]. Table 13 shows the purity of the eluates from differential protein A purification of in-supernatant Fab arm exchange generated bsRSV-L[TLQ]. bsRSV-L[TLQ] was isolated to over 95% purity.

TABLE 13

| Elution pH | % RSV-L[TLQ] | % bsRSV-L[TLQ] | % gp120-R |
|---|---|---|---|
| 4.7 | 21.4 | 78.6 | N.D. |
| 4.2 | N.D. | >99 | N.D. |
| 3.4 | N.D. | 21.2 | 78.8 |

*N.D. = not detected

For the in-supernatant Fab arm exchange producing bsRSV-L[Q311R], remaining parental RSV-L[Q311R] was removed by elution at pH 4.6 (FIG. 6B) and remaining parental gp120-R was removed by elution at pH 3.4 (FIG. 6D). Efficient elution of parental RSV-L[Q311R] required a slightly more acidic pH due to the single mutation binding protein A stronger than the triple mutant T307P/L309Q/Q311R. Solely BsAb eluted at pH 4.2 (FIG. 6C). Some bsRSV-L[Q311R] eluted at pH 3.4 (FIG. 6D) and at pH 4.6 (FIG. 6B), resulting in a decreased final yield of purified BsAb.

Table 14 shows the purity of the eluates from differential protein A purification of in-supernatant Fab arm exchange generated bsRSV-L[Q311R]. bsRSV-L[Q311R] was purified to over 95% purity.

TABLE 14

| Elution pH | % RSV-L[Q311R] | % bsRSV-L[Q311R] | % gp120-R |
|---|---|---|---|
| 4.6 | 14.5 | 85.5 | N.D. |
| 4.2 | N.D. | >99 | N.D. |
| 3.4 | N.D. | 17.1 | 82.9 |

*N.D. = not detected

In conclusion, this experiment demonstrated the utility of Q311R and T307P/L309Q/Q311R mutations for efficient separation of bispecific antibodies generated by in-supernatant Fab arm exchange.

Methods

Parental mAbs RSV-L[Q311R] or RSV-L[TLQ] and gp120-R were expressed in Expi293 cells and antibody titers were determined (Octet, ForteBio). To produce bispecific antibodies bsRSV-L[Q311R] and bsRSV-L[TLQ], culture supernatants containing equivalent milligram quantities of RSV-L[Q311R] and gp120-R or RSV-L[TLQ] and gp120-R were combined and Fab arm exchange reactions were performed at a final protein concentration of 0.2 mg/mL by the addition of 2-mercaptoethylamine to a final concentration of 75 mM followed by incubation at 31° C. for 5 hours and extensive dialysis into 1×DPBS pH 7.4 (Labrijn Aran F, Meesters Joyce I et al. 2014). Following dialysis proteins were applied to a 1 mL mAbSelect Sure column (GE) and eluted using a pH step gradient.

Prior to purification, control mixes containing equivalent 1 mg quantities of purified parental mAbs and bispecific antibodies were separated on a 1 mL mAbSelect Sure column (GE) to determine optimal elution conditions. A purified protein mix containing RSV-L[Q311R], gp120-R and bsRSV-L[Q311R] showed optimal separation of parental mAbs from BsAb by eluting with 50 mM citrate pH 4.6 for 30 column volume (CV) followed by 50 mM citrate pH 4.2 for 30 CV followed by 50 mM citrate pH 3.4 for 20 CV. A purified protein mix containing RSV-L[TLQ], gp120-R and bsRSV-L[TLQ] showed optimal separation of parental mAbs from the bispecific mAb by eluting with 50 mM citrate pH 4.7 for 30 CV followed by 50 mM citrate pH 4.2 for 30 CV followed by 50 mM citrate pH 3.4 for 20 CV.

Therefore, bsRSV-L[Q311R] produced from in-supernatant crossed parental mAbs was eluted with 50 mM citrate pH 4.6 for 30 CV followed by 50 mM citrate pH 4.2 for 30 CV followed by 50 mM citrate pH 3.4 for 20 CV in subsequent experiments. bsRSV-L[TLQ] produced from in-supernatant crossed parental mAbs was eluted with 50 mM citrate pH 4.7 for 30 CV followed by 50 mM citrate pH 4.2 for 30 CV followed by 50 mM citrate pH 3.4 for 20 CV in subsequent experiments. The optimal elution conditions for each bispecific antibody pair were used in subsequent experiments.

Efficiency of separation was assessed using hydrophobic interaction chromatography. Elution fractions from each pH step were pooled, neutralized with Tris pH 7.5, and concentrated for analysis. Samples were prepared at equivalent protein concentrations, diluted 1:2 into binding buffer (0.1M NaHPO$_4$ pH 6.5, 1.5M (NH$_4$)$_2$SO$_4$), applied to a 4.6 mm×10 cm TSKgel® Butyl-NPR column (Tosoh Bioscience, LLC) equilibrated in 0.1 M NaHPO$_4$ pH 6.5, 1.5 M (NH$_4$)$_2$SO$_4$ and eluted at 0.5 mL/min using a gradient to 0.1 M NaHPO$_4$ pH 6.5 over 25 min.

Example 7. Separation of Bispecific Antibodies from Parental Monospecific mAbs after in Vitro Fab Arm Exchange Starting from Co-Transfected Material Applicability of utilizing Q311R or T307P/L309Q/Q311R mutations to purify bispecific antibodies generated utilizing common light chain technology instead of Fab arm exchange was evaluated.

Generated bispecific antibodies bsTNF-[TLQ] and bsTNF-[Q311R] were isolated to over 95% purity using the 3 pH step elution methods described in previous examples. bsTNF-[TLQ] and bsTNF-[Q311R] eluted at pH 4.2. Additionally, the parental TNF-[TLQ] and TNF-[Q311R] eluted efficiently at the pH 4.7, with no mAb being detected in other eluates. The purity of bsTNF-[TLQ] and bsTNF-[Q311R] isolated from pH 4.2 elution was high, however the yields of the bispecific antibodies were slightly lower when compared to bispecific antibodies generated using Fab arm exchange, due to the significantly different expression levels of the two parental mAbs when co-transfected (~300 mg/L for TNF-[TLQ] parental vs ~35 mg/L for aVb5). Despite the ~10-fold difference in expression levels of parental mAbs, introduction of T307P/L309Q/Q311R mutations facilitated isolation of over 95% pure bsTNF-[TLQ], which accounted for only ~10% of the total antibody population in the initial sample). Table 15 shows the purity of the eluates from differential protein A purification of the bsTNF-[TLQ] generated using common light chain technology. Table 16 shows the purity of the eluates from differential protein A purification of i bsTNF-[Q311R] generated using common light chain technology.

Figure 7A:
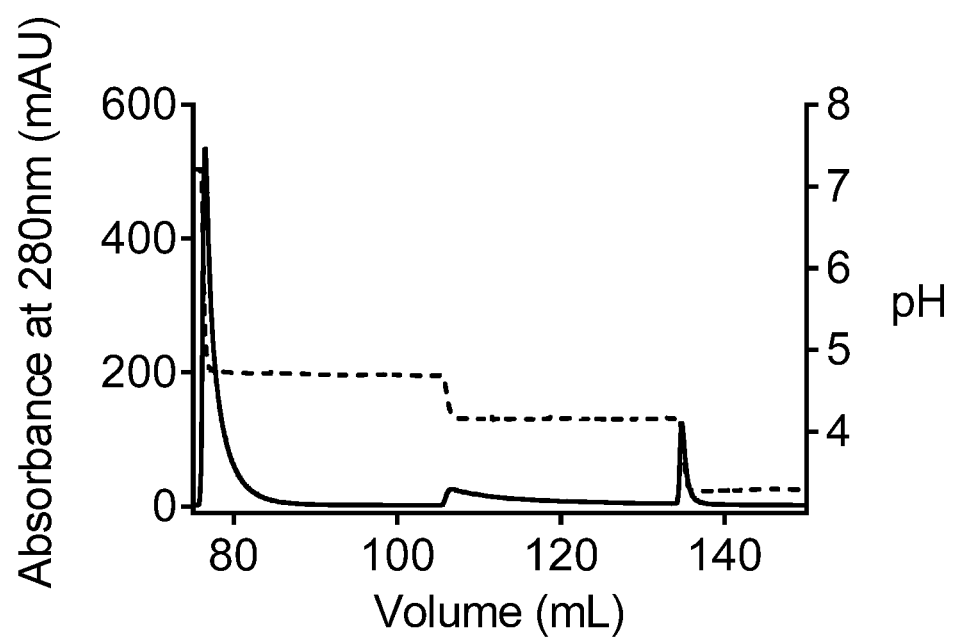
FIG. 7A shows protein A chromatogram of a sample of bsTNF-[TLQ] generated using common light chain technology.

FIG. 7A shows protein A chromatogram of a sample of bsTNF-[TLQ] generated using common light chain technology showing three distinct peaks eluting at pH 4.7, 4.2 and 3.4.

Figure 7B:
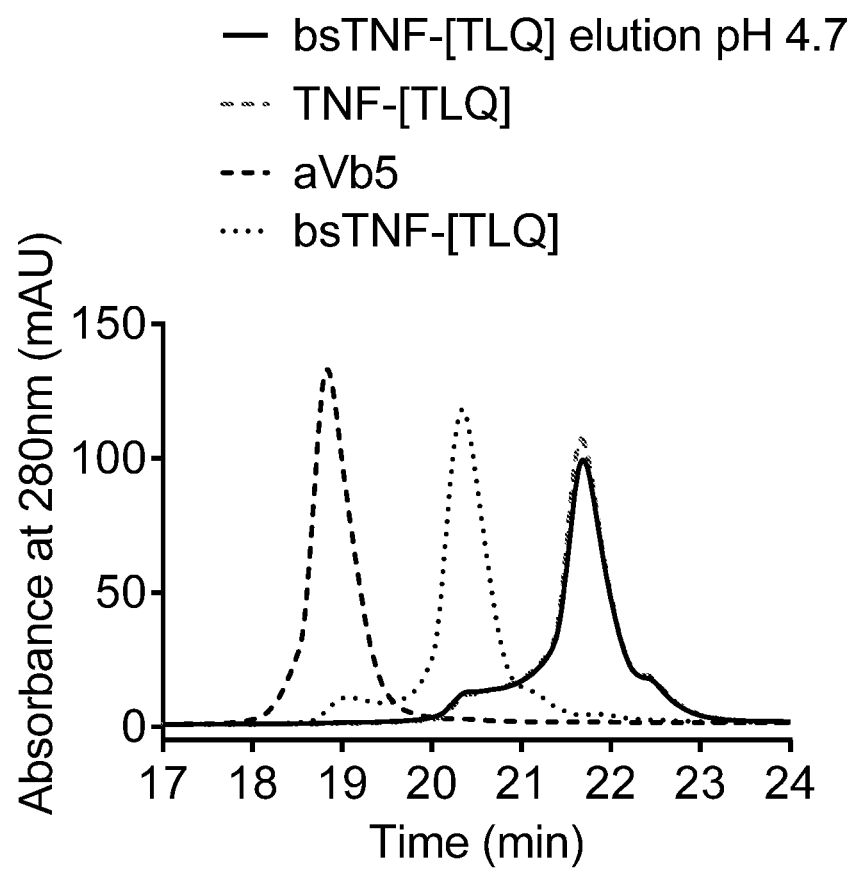
FIG. 7B shows HIC analyses of protein A affinity column pH 4.7 eluates of a sample of bsTNF-[TLQ] generated using common light chain technology.

FIG. 7B shows HIC analyses of protein A affinity column pH 4.7 eluates of a sample of bsTNF-[TLQ] generated using common light chain technology.

Figure 7C:
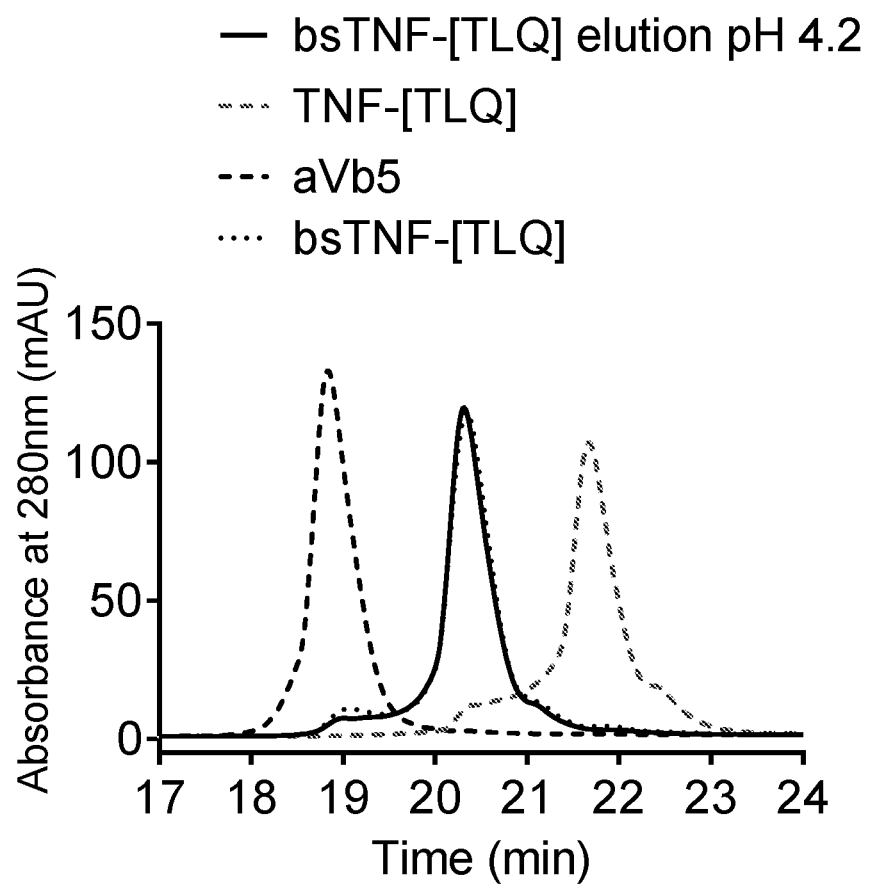
FIG. 7C shows HIC analyses of protein A affinity column pH 4.2 eluates of a sample of bsTNF-[TLQ] generated using common light chain technology.

FIG. 7C shows HIC analyses of protein A affinity column pH 4.2 eluates of a sample of bsTNF-[TLQ] generated using common light chain technology.

Figure 7D:
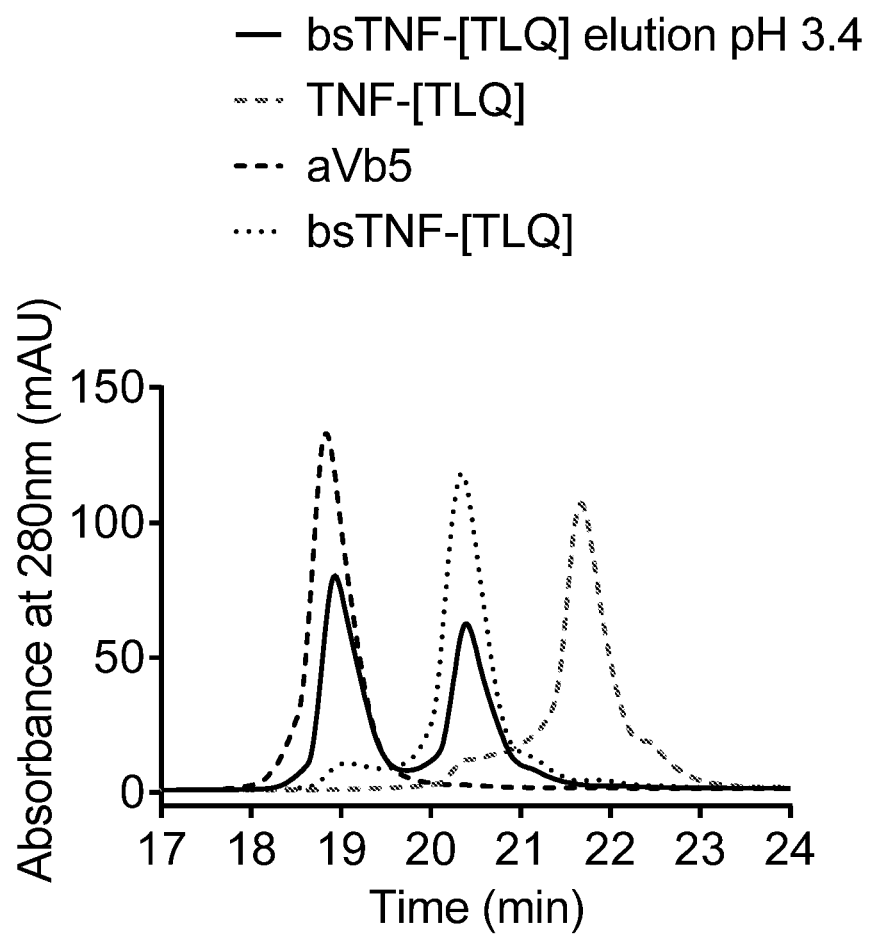
FIG. 7D shows HIC analyses of protein A affinity column pH 3.4 eluates of a sample of bsTNF-[TLQ] generated using common light chain technology.

FIG. 7D shows HIC analyses of protein A affinity column pH 3.4 eluates of a sample of bsTNF-[TLQ] generated using common light chain technology.

Similar chromatograms were obtained from samples of bsTNF-[Q311R] generated using common light chain technology.

TABLE 15

| Elution pH | % TNF-[TLQ] | % bsTNF-[TLQ] | % aVb5 |
|---|---|---|---|
| 4.7 | 2.9 | 89.6 | 7.4 |
| 4.2 | 1.3 | 96.8 | 1.9 |
| 3.4 | N.D. | 47.6 | 52.4 |

*N.D. = not detected

TABLE 16

| Elution pH | % TNF-[Q311R] | % bsTNF-[Q311R] | % aVb5 |
|---|---|---|---|
| 4.6 | 100 (73.3) | N.D. | N.D. |
| 4.2 | 1.9 (0.3) | 97.0 (15.8) | 1.1 (0.18) |
| 3.4 | N.D. | 51.4 (5.3) | 48.6 (5.1) |

*N.D. = not detected

Methods

Parental antibodies TNF-[Q311R], TNF-[TLQ] and aVb5 (see Table 8) were used in the experiments. The parental anti-TNF and anti-αVβV antibodies share a common light chain, and therefore the mAbs were used in the experiments to minimize the mAb species which could be generated by light chain mispairing.

Co-transfections of TNF-[Q311R] and aVb5 or TNF-[TLQ] and aVb5 were carried out in Expi293 cells according to the manufacturer's protocol using a molar ratio of 0.5: 0.5:3.0 of plasmid for TNF-[Q311R] or TNF-[TLQ] heavy chain:aVb5 heavy chain:light chain. To determine the approximate relative expression levels, separate transfections of parental mAbs were also performed using a 1.0:3.0 molar ratio of heavy chain:light chain plasmids and titers determined using Octet. Approximately 50 mL of each supernatant were applied to a 1 mL mAbSelect Sure column and eluted using a 3-step pH step gradient of 50 mM citrate pH 4.7 (or 4.6), 4.2, and 3.4 Fractions were collected, concentrated and buffer exchanged into 1×PBS prior to HIC analysis.

Example 8. Q311R or T307P/L309Q/Q311R Mutations have No Effect on Antibody Serum Half-Life Tg32 hemizygous mice were used to study PK properties of select antibodies. In these experiments, RSV-L had a half-life of ~7 days. Both the homodimeric parental Abs harboring either Q311R or T307P/L309Q/Q311R mutations (antibodies RSV-L[Q311R] and RSV-L[TLQ]) had half-lives at least as long as the wild-type mAb (~7 and 9 days, respectively). The mutations also had little effect on serum half-life when introduced asymmetrically into bispecific antibodies. bsRSV-L[Q311R] and bsRSV-L[TLQ] had serum half-lives of 11/1±3.6 and 4.8±2.0 days, respectively. RSV-L serum half-life was 7.0±3.9 days, RSV-L[TLQ] half-life was 9.0±4.0 days and RSV-L[Q311R] serum half-life was 6.7±3.4 days. I253D mutant Ab does not bind FcRn and was used as a control in the experiment.

FIG. 8 shows the results of the pharmacokinetic analysis of select variants. These results are consistent with the in vitro FcRn binding analysis (Example 3). The experimental results demonstrate that asymmetrically introduced Q311R or T307P/L309Q/Q311R mutations into bispecific antibodies generated using a spectrum of technologies result in antibodies which retain their normal serum half-life and allow differential protein A affinity purification of the bispecific antibodies from contaminating parental monospecific antibodies.

Methods

Tg32 hemizygous mice (Jackson Laboratories stock. #014565) were used for the antibody pharmacokinetic (PK) studies. These mice are transgenic for the human α-microglobulin subunit of FcRn and thus help to predict serum half-life in human. (Petkova et al., *Int Immunol* 18:1759-1769, 2006). Mice were injected with test Abs intravenously via tail vein at a dose of 2 mg/kg into 4 animals per group. Time points were taken at 1 h, 1 d, 3 d, 7 d, 14 d and 21 d. Serial retro-orbital bleeds were obtained from $CO_2$-anesthetized mice at the indicated time points and terminal bleeds were taken by cardiac puncture. After 30 min at room temperature, blood samples were centrifuged 3,000×g for 15 min and serum collected for analyses.

For detection of the test Abs in mouse sera, an electrochemiluminescent immunoassay was used. Streptavidin Gold multi-array 96-well plates (Meso Scale Discovery) were coated overnight with 50 μL/well of 3 μg/mL Biotin-F(ab')$_2$ fragment g anti-h IgG, Fc fragment specific (Jackson Immunoresearch cat. #109-066-008) in Starting Block™ (Thermo); then washed in Tris-buffered saline with Tween® 20 (TBST). Sera samples were diluted in 5% CD-1 mouse serum in Starting Block™ (1:20, then serial 2-fold dilutions), incubated on plates for 2 h and washed. Ru' labeled anti-h IgG F(ab')$_2$ (prepared from Jackson 109-006-097) in 1% BSA-TBST was added and incubated on plates for 1.5 h and washed. Two hundred microliters/well of Read Buffer with surfactant was added and plates were read in a MSD Sector Imager 6000 plate reader. Serum concentrations of the IgG2b Abs were determined from a standard curve using a 4-parameter non-linear regression program in Prism 6.01 software.

Terminal half-life ($t_{1/2}$) calculations of the elimination phase (β phase) for PK studies were determined using the 1-phase exponential decay model fitted by non-linear regression of natural log concentration versus time using Prism version 6.01 software. The least squares nonlinear decay model was weighted by the inverse of the fitted concentration. Half-life calculations of the elimination phase (β phase) were determined using the formula $t_{1/2}=\ln^2/\beta$, where β is the −slope of the line fitted by the least square regression analysis starting after first dose. The terminal half-life value for an Ab was determined by taking the average of the $t_{1/2}$ values calculated for each animal within the test group.

We claim:

1. A multimeric protein comprising a first polypeptide and a second polypeptide, wherein the first polypeptide comprises a first CH2-CH3 region comprising mutation Q311R, Q311K, T307P/L309Q, or T307P/L309Q/Q311R and the second polypeptide comprises a second CH2-CH3 region comprising a wild-type amino acid residue at positions 307, 309 and 311, wherein residue numbering is according to the EU Index, the multimeric protein further comprising asymmetric stabilizing mutations in the first CH2-CH3 region and in the second CH2-CH3 region, wherein the multimeric protein has reduced binding to protein A ligand as determined by differential protein A affinity chromatography using a pH gradient relative to a reference parental multimeric protein comprising a first reference polypeptide comprising a first reference CH2-CH3 region comprising a wild-type amino acid residue at positions 307, 309 and 311 and a second reference polypeptide comprising a second reference CH2-CH3 region comprising a wild-type amino acid residue at positions 307, 309 and 311.

2. The multimeric protein of claim 1, wherein the first CH2-CH3 region and the second CH2-CH3 region is an IgG1, an IgG2 or an IgG4 isotype.

3. The multimeric protein of claim 1, wherein the protein A ligand comprises Staphylococcal Protein A, Z-domain or Y-domain.

4. The multimeric protein of claim 3, wherein Z-domain comprises an amino acid sequence of SEQ ID NO: 1.

5. The multimeric protein of claim 1, wherein the asymmetric stabilizing mutations in the first CH2-CH3 region and in the second CH2-CH3 region or in the second CH2-CH3 region and in the first CH2-CH3 region are
   a) F405L and K409R, respectively;
   b) wild-type and F405L/R409K, respectively;
   c) T366W and T366S/L368A/Y407V, respectively;
   d) T366Y/F405A and T394W/Y407T, respectively;
   e) T366W/F405W and T394S/Y407A, respectively;
   f) F405W/Y407A and T366W/T394S, respectively;
   g) L351Y/F405A/Y407V and T394W, respectively;
   h) T366I/K392M/T394W and F405A/Y407V, respectively;
   i) T366L/K392M/T394W and F405A/Y407V, respectively;
   j) L351Y/Y407A and T366A/K409F, respectively;
   k) L351Y/Y407A and T366V/K409F, respectively;
   l) Y407A and T366A/K409F, respectively;
   m) D399K/E356K and K409D/K392D, respectively; or
   n) D399K/E356K/E357K and K409D/K392D/K370, respectively.

6. The multimeric protein of claim 5, wherein the first CH2-CH3 region and the second CH2-CH3 region comprise an amino acid sequence of
   a) SEQ ID NOs: 2, and 22, respectively;
   b) SEQ ID NOs: 3 and 22, respectively;
   c) SEQ ID NOs: 4 and 22, respectively;
   d) SEQ ID NOs: 5 and 22, respectively;
   e) SEQ ID NOs: 6 and 23, respectively;
   f) SEQ ID NOs: 7 and 23, respectively;
   g) SEQ ID NOs: 8 and 23, respectively;
   h) SEQ ID NOs: 9 and 23, respectively;
   i) SEQ ID NOs: 10 and 24, respectively;
   j) SEQ ID NOs: 11 and 24, respectively;
   k) SEQ ID NOs: 12 and 24, respectively;
   l) SEQ ID NOs: 13 and 24, respectively;
   m) SEQ ID NOs: 14 and 25, respectively;
   n) SEQ ID NOs: 15 and 25, respectively;
   o) SEQ ID NOs: 16 and 25, respectively;
   p) SEQ ID NOs: 17 and 25, respectively;
   q) SEQ ID NOs: 18 and 26, respectively;
   r) SEQ ID NOs: 19 and 26, respectively;
   s) SEQ ID NOs: 20 and 26, respectively;
   t) SEQ ID NOs: 21 and 26, respectively;
   u) SEQ ID NOs: 52 and 54, respectively; or
   v) SEQ ID NOs: 52 and 55, respectively.

7. The multimeric protein of claim 1, wherein the first CH2-CH3 region and/or the second CH2-CH3 region is coupled to a heterologous protein.

8. The multimeric protein of claim 7, wherein the heterologous protein is a peptide, an extracellular domain of a receptor, an extracellular domain of a ligand, a secreted protein, a scFv, a Fab, a heavy chain variable region (VH), a light chain variable region (VL), a fibronectin type III domain and/or a fynomer.

9. The multimeric protein of claim 8, wherein the heterologous protein is coupled to the N-terminus or to the C-terminus of the first CH2-CH3 region and/or the second CH2-CH3 region, optionally via a linker.

10. The multimeric protein of claim 9, wherein the linker comprises an amino acid sequence of SEQ ID NOs: 57, 58, 59, 60, 61, 62, 63, 64, 65, 66, 67, 92, 93, 94, 95, 96, 97 or 98.

11. The multimeric protein of claim 1, wherein the multimeric protein is an antibody.

12. The multimeric protein of claim 11, wherein the antibody is multispecific, bispecific or monospecific.

13. The multimeric protein of claim 12, wherein the antibody further comprises at least one mutation that modulates binding of the antibody to FcγR or FcRn.

14. The multimeric protein of claim 13, wherein the at least one mutation that modulates binding of the antibody to FcγR or FcRn is L234A, F234A, V234A, L235A, G237A, P238S, H268A, V309L, A330A, P331S, L234A/L235A, F234A/L235A, V234A/L235A, V234A/G237A/P238S/H268A/V309L/A330S/P331S, L234A/L235A/G237A/P238S/H268A/A330S/P331S, S239D/I332E, S298A/E333A/K334A, F243L/R292P/Y300L, F243L/R292P/Y300L/P396L, F243L/R292P/Y300L/V3051/P396L, G236A/S239D/I332E, S267E, S267E/L328F, S267E/I332E or M252Y/S254T/T256E.

15. The multimeric protein of claim 12, wherein the antibody comprises a first light chain and a second light chain.

16. The multimeric protein of claim 15, wherein the first light chain and the second light chain have identical amino acid sequences.

17. The multimeric protein of claim 12, wherein the antibody binds two or more antigens.

18. The multimeric protein of claim 17, wherein the two or more antigens are any two of PD1, CD27, CD28, NKP46, ICOS, GITR, OX40, CTLA4, LAG3, TIM3, KIR, CD73, CD39, IDO, BTLA, VISTA, TIGIT, CD96, CD30, HVEM, DNAM-1, LFA, tumor antigen, EGFR, cMet, FGFR, ROR1, CD123, IL1RAP, FGFR, mesothelin, CD3, T cell receptor, CD32b, CD32a, CD16a, CD16b, NKG2D, NKP46, CD28, CD47, DLL, CD8, CD89, HLA, B cell receptor or CD137.

19. A pharmaceutical composition comprising the multimeric protein of claim 1.

20. An isolated antibody comprising two heavy chains or fragments thereof having identical amino acid sequences and two light chains or fragments thereof, wherein the two heavy chains comprise a mutation Q311R, Q311K, T307P/L309Q, or T307P/L309Q/Q311R, wherein residue numbering is according to the EU Index.

21. The isolated antibody of claim 20, wherein the two heavy chains or fragments thereof further comprise a mutation F405L, K409R, F405L/R409K, T366W or T366S/L368A/Y407V.

22. The isolated antibody of claim of 20, wherein the antibody is an IgG1, an IgG2 or an IgG4 isotype.

23. The isolated antibody of claim 22, comprising a heavy chain CH2-CH3 region of SEQ ID Nos: 2, 3, 4, 5, 6, 7, 8, 9, 10, 11, 12, 13, 14, 15, 16, 17, 18, 19, 20, 21, 52.

24. An isolated polynucleotide
 a) comprising a polynucleotide encoding a first CH2-CH3 region comprising a mutation Q311R, Q311K, T307P/L309Q, or T307P/L309Q/Q311R;
 b) comprising the polynucleotide encoding the first CH2-CH3 region comprising a mutation Q311R, Q311K, T307P/L309Q, or T307P/L309Q/Q311R and the second CH2-CH3 region comprising a wild-type amino acid residue at positions 307, 309 and 311, wherein residue numbering is according to the EU Index;
 c) comprising the polynucleotide encoding the polypeptide comprising the first CH2-CH3 region of SEQ ID NOs: 2, 3, 4, 5, 6, 7, 8, 9, 10, 11, 12, 13, 14, 15, 16, 17, 18, 19, 20, 21, 52, 54 or 55; or
 d) comprising the polynucleotide sequence of SEQ ID NOs: 27, 28, 29, 30, 31, 32, 33, 34, 35, 36, 37, 38, 39, 40, 41, 42, 43, 44, 45, 46, 87, 89 or 90.

25. A vector comprising
 a) the polynucleotide encoding the first CH2-CH3 region comprising a mutation Q311R, Q311K, T307P/L309Q, or T307P/L309Q/Q311R;
 b) the polynucleotide encoding the polypeptide comprising the CH2-CH3 region of SEQ ID NOs: 2, 3, 4, 5, 6, 7, 8, 9, 10, 11, 12, 13, 14, 15, 16, 17, 18, 19, 20, 21, 52, 54 or 55;
 c) the polynucleotide comprising the polynucleotide sequence of SEQ ID NOs: 27, 28, 29, 30, 31, 32, 33, 34, 35, 36, 37, 38, 39, 40, 41, 42, 43, 44, 45, 46, 87, 89 or 90;
 d) the polynucleotide comprising the polynucleotide encoding the first CH2-CH3 region comprising a mutation Q311R, Q311K, T307P/L309Q, or T307P/L309Q/Q311R or and the second CH2-CH3 region comprising a wild-type amino acid residue at positions 307, 309 and 311; or
 e) the isolated polynucleotide comprising
  i) SEQ ID NOs: 27, and 47, respectively;
  ii) SEQ ID NOs:28 and 47, respectively;
  iii) SEQ ID NOs: 29 and 47, respectively;
  iv) SEQ ID NOs: 30 and 47, respectively;
  v) SEQ ID NOs: 31 and 48, respectively;
  vi) SEQ ID NOs: 32 and 48, respectively;
  vii) SEQ ID NOs: 33 and 48, respectively;
  viii) SEQ ID NOs: 34 and 48, respectively;
  ix) SEQ ID NOs: 35 and 49, respectively;
  x) SEQ ID NOs: 36 and 49, respectively;
  xi) SEQ ID NOs: 37 and 49, respectively;
  xii) SEQ ID NOs: 38 and 49, respectively;
  xiii) SEQ ID NOs: 39 and 50, respectively;
  xiv) SEQ ID NOs: 40 and 50, respectively;
  xv) SEQ ID NOs: 41 and 50, respectively;
  xvi) SEQ ID NOs: 42 and 50, respectively;
  xvii) SEQ ID NOs: 43 and 51, respectively;
  xviii) SEQ ID NOs: 44 and 51, respectively;
  xix) SEQ ID NOs: 45 and 51, respectively;
  xx) SEQ ID NOs: 46 and 51, respectively;
  xxi) SEQ ID Nos: 87 and 89, respectively;
  xxii) SEQ ID Nos: 87 and 90, respectively;
  xxv) SEQ ID NOs: 92 and 89, respectively; or
  xxvi) SEQ ID Nos: 92 and 90, respectively.

26. A host cell comprising the vector of claim 25.

27. The host cell of claim 26, wherein the host cell is a hybridoma, a myeloma, SP2/0, NS0, U266, CHO, CHO-K1SV, CHO-K1, DG44 or Hek293.

28. A method of making the multimeric protein of claim 3, comprising
 a) culturing the host cell of claim 26 under conditions that the multimeric protein is expressed; and
 b) purifying the multimeric protein using protein A ligand affinity chromatography.

29. A method of making an isolated multispecific antibody comprising a first heavy chain or fragment thereof comprising a mutation Q311R, Q311K, T307P/L309Q, or T307P/L309Q/Q311R and a second heavy chain or fragment thereof comprising wild-type amino acid residue at positions 307, 309 and 311, comprising
 a) providing a first parental antibody comprising the first heavy chain or fragment thereof comprising the mutation Q311R, Q311K, T307P/L309Q, or T307P/L309Q/Q311R and a first light chain;
 b) providing a second parental antibody comprising the second heavy chain or fragment thereof comprising wild-type amino acid residue at positions 307, 309 and 311 and a second light chain;
 c) contacting the first parental antibody and the second parental antibody in a sample;
 d) incubating the sample; and
 e) purifying the multispecific antibody using protein A ligand affinity chromatography.

30. The method of claim 29, wherein the isolated multispecific antibody further comprises asymmetric stabilizing mutations in the first heavy chain or fragment thereof and in the second heavy chain or fragment thereof.

31. The method of claim 30, wherein the asymmetric stabilizing mutations in the first heavy chain or fragment thereof and in the second heavy chain or fragment thereof or in the second heavy chain or fragment thereof and in the first heavy chain or fragment thereof are
 a) F405L and K409R, respectively;
 b) wild-type and F405L/R409K, respectively;
 c) T366W and T366S/L368A/Y407V, respectively;
 d) T366Y/F405A and T394W/Y407T, respectively;

e) T366W/F405W and T394S/Y407A, respectively;
f) F405W/Y407A and T366W/T394S, respectively;
g) L351Y/F405A/Y407V and T394W, respectively;
h) T366I/K392M/T394W and F405A/Y407V, respectively;
i) T366L/K392M/T394W and F405A/Y407V, respectively;
j) L351Y/Y407A and T366A/K409F, respectively;
k) L351Y/Y407A and T366V/K409F, respectively;
l) Y407A and T366A/K409F, respectively;
m) D399K/E356K and K409D/K392D, respectively; or
n) D399K/E356K/E357K and K409D/K392D/K370, respectively.

32. The method of claim 29, wherein the isolated multi-specific antibody is an IgG1, an IgG2 or an IgG4 isotype.

33. The method of claim 29, wherein a reducing agent is added during step d).

34. The method of claim 33, wherein the reducing agent is 2-mercaptoethylamine (2-MEA), dithiothreitol (DTT), dithioerythritol (DTE), glutathione, tris(2-carboxyethyl) phosphine (TCEP), L-cysteine or beta-mercaptoethanol.

35. The method of claim 34, wherein 2-MEA is present at a concentration of
a) about 10 mM to about 100 mM; or
b) about 25 mM to about 75 mM.

36. The method of claim 29, wherein step d) is performed at a temperature of about 20° C. to about 37° C. about ninety minutes to about six hours.

37. The method of claim 29, wherein protein A ligand affinity chromatography employs a pH gradient.

38. The method of claim 37, wherein the pH gradient is
a) from about pH 7.0 to about pH 3.0; or
b) from about pH 4.6 to about pH 3.4.

39. The method of claim 38, wherein the multimeric antibody elutes between about pH 4.4 to about pH 4.1.

40. The method of claim 37, wherein protein A ligand affinity chromatography employs a citrate buffer.

41. The method of claim 29, wherein the multi specific antibody is a bispecific antibody.

* * * * *